(12) United States Patent
He et al.

(10) Patent No.: US 12,359,242 B2
(45) Date of Patent: Jul. 15, 2025

(54) CHEMICAL PLATFORM ASSISTED PROXIMITY CAPTURE (CAP-C)

(71) Applicant: The University of Chicago, Chicago, IL (US)

(72) Inventors: Chuan He, Chicago, IL (US); Qiancheng You, Chicago, IL (US)

(73) Assignee: The University of Chicago, Chicago, IL (US)

( * ) Notice: Subject to any disclaimer, the term of this patent is extended or adjusted under 35 U.S.C. 154(b) by 1287 days.

(21) Appl. No.: 17/250,024

(22) PCT Filed: May 8, 2019

(86) PCT No.: PCT/US2019/031309
§ 371 (c)(1),
(2) Date: Nov. 6, 2020

(87) PCT Pub. No.: WO2019/217549
PCT Pub. Date: Nov. 14, 2019

(65) Prior Publication Data
US 2021/0317506 A1   Oct. 14, 2021

Related U.S. Application Data

(60) Provisional application No. 62/668,994, filed on May 9, 2018, provisional application No. 62/668,543, filed on May 8, 2018.

(51) Int. Cl.
| | |
|---|---|
| *C12Q 1/6806* | (2018.01) |
| *C07C 69/003* | (2006.01) |
| *C12N 15/11* | (2006.01) |

(52) U.S. Cl.
CPC .......... *C12Q 1/6806* (2013.01); *C07C 69/003* (2013.01); *C12N 15/11* (2013.01); *C12N 2830/46* (2013.01); *C12Q 2565/518* (2013.01)

(58) Field of Classification Search
CPC ............ C12Q 1/6806; C12Q 2565/518; C07C 69/003; C12N 15/11; C12N 2830/46
(Continued)

(56) References Cited

U.S. PATENT DOCUMENTS

| | | |
|---|---|---|
| 2014/0308730 A1 | 10/2014 | Nikiforov et al. |
| 2014/0378316 A1 | 12/2014 | Darnell et al. |

FOREIGN PATENT DOCUMENTS

| | | |
|---|---|---|
| WO | WO 2017/147279 | 8/2017 |
| WO | WO 2018/045137 | 3/2018 |

OTHER PUBLICATIONS

Widmer et al. Analysis of the psoralen-crosslinking pattern in chromatin DNA by exonuclease digestion. Nucleic Acids Research. 16, 1988, 7013-7024. (Year: 1988).*

(Continued)

*Primary Examiner* — Aaron A Priest
*Assistant Examiner* — Randi Lynn Beil
(74) *Attorney, Agent, or Firm* — Norton Rose Fulbright US LLP

(57) ABSTRACT

Certain embodiments are directed to compositions and methods for capture of elements in physical proximity. In certain aspects the methods comprise (a) contacting a target with a functionalized scaffold or capture agent that comprises activatable cross-linking moieties to form a target/scaffold mixture; (b) exposing the target/scaffold mixture to an activator to activate the cross-linking moieties of the dendrimer and form a cross-linked target/scaffold complex; (c) isolating the target/scaffold complexes; and (d) identify portions of the target or targets that are cross linked with the scaffold.

25 Claims, 55 Drawing Sheets

Specification includes a Sequence Listing.

(58) Field of Classification Search
USPC .......................................................... 506/4
See application file for complete search history.

(56) References Cited

OTHER PUBLICATIONS

Benters et al., "DNA microarrays with PAMAM dendritic linker systems" *Nucleic Acids Research*, 2002, vol. 30, No. 2: e10, 7 pages.
Extended European Search Report issued in Corresponding European Application No. 19799707.5, dated Jan. 19, 2022.
Lin et al ., "Digestion-ligation-only Hi-C is an efficient and cost-effective method for chromosome conformation capture" *Nature Genetics* 2018, 50, 754-763.
Wang et al., "Time-resolved Proteomic Visualization of Dendrimer Cellular Entry and Trafficking" *J Am Chem Soc.* 2015, 137(40): 12772-12775.
Astruc et al., "Dendrimers Designed for Functions: From Physical, Photophysical, and Supramolecular Properties to Applications in Sensing, Catalysis, Molecular Electronics, Photonics, and Nanomedicine" *Chemical Reviews* 2010, 110, 1857-1959.
Bonev et al., "Multiscale 3D Genome Rewiring during Mouse Neural Development" *Cell* 2017, 171, 557-72.e524.
Dekker et al., "Capturing Chromosome Conformation" *Science* 2002, 295, 1306-11.
Dixon et al., "Topological domains in mammalian genomes identified by analysis of chromatin interactions" *Nature* 2012, 485, 376-80.
Dostie et al., "Chromosome Conformation Capture Carbon Copy (5C): A massively parallel solution for mapping interactions between genomic elements" *Genome Research* 2006, 16, 1299-1309.
Dowen et al., "Control of Cell Identity Genes Occurs in Insulated Neighborhoods in Mammalian Chromosomes" *Cell* 2014, 159, 374-87.
Ernst, Jason and Manolis Kellis, "Chromatin state discovery and genome annotation with ChromHMM" *Nature Protocols* 2017, 12(12), 2478-2492.
Fudenberg et al., "Formation of Chromosomal Domains by Loop Extrusion" *Cell Reports* 2016, 15, 2038-49.
Hsieh et al., "Mapping Nucleosome Resolution Chromosome Folding in Yeast by Micro-C" *Cell* 2015, 162, 108-19.
Hsieh et al., "Micro-C XL: assaying chromosome conformation from the nucleosome to the entire genome" *Nat. Methods* 2016, 13, 1009-11.
International Search Report and Written Opinion issued in Corresponding PCT Application No. PCT/US2019/031309, dated Jul. 24, 2019.
Lau et al., "Elucidating combinatorial histone modifications and crosstalks by coupling histone-modifying enzyme with biotin ligase activity." *Nucleic Acids Research* 2012, 41(3), e49, 10 pages.
Lieberman-Aiden et al., "Comprehensive Mapping of Long-Range Interactions Reveals Folding Principles of the Human Genome" *Science* 2009, 326, 289-93.
Ma et al., "Fine-scale chromatin interaction maps reveal the cis-regulatory landscape of human lincRNA genes" *Nat. Methods* 2015, 12, 71-78.
Phillips-Cremins et al., "Architectural Protein Subclasses Shape 3D Organization of Genomes during Lineage Commitment" *Cell* 2013, 153, 1281-95.
Rao et al., "A 3D Map of the Human Genome at Kilobase Resolution Reveals Principles of Chromatin Looping" *Cell* 2014, 159, 1665-80.
Zhao et al., "Circular chromosome conformation capture (4C) uncovers extensive networks of epigenetically regulated intra- and interchromosomal interactions" *Nat. Genet.* 2006, 38, 1341-47.
Zhou et al., "Cross-platform detection of epigenetic modifications from extracted chromatin in leucocytes from blood" *Analytical Chemistry Research* 2015, 4, 39-44.

* cited by examiner

A.

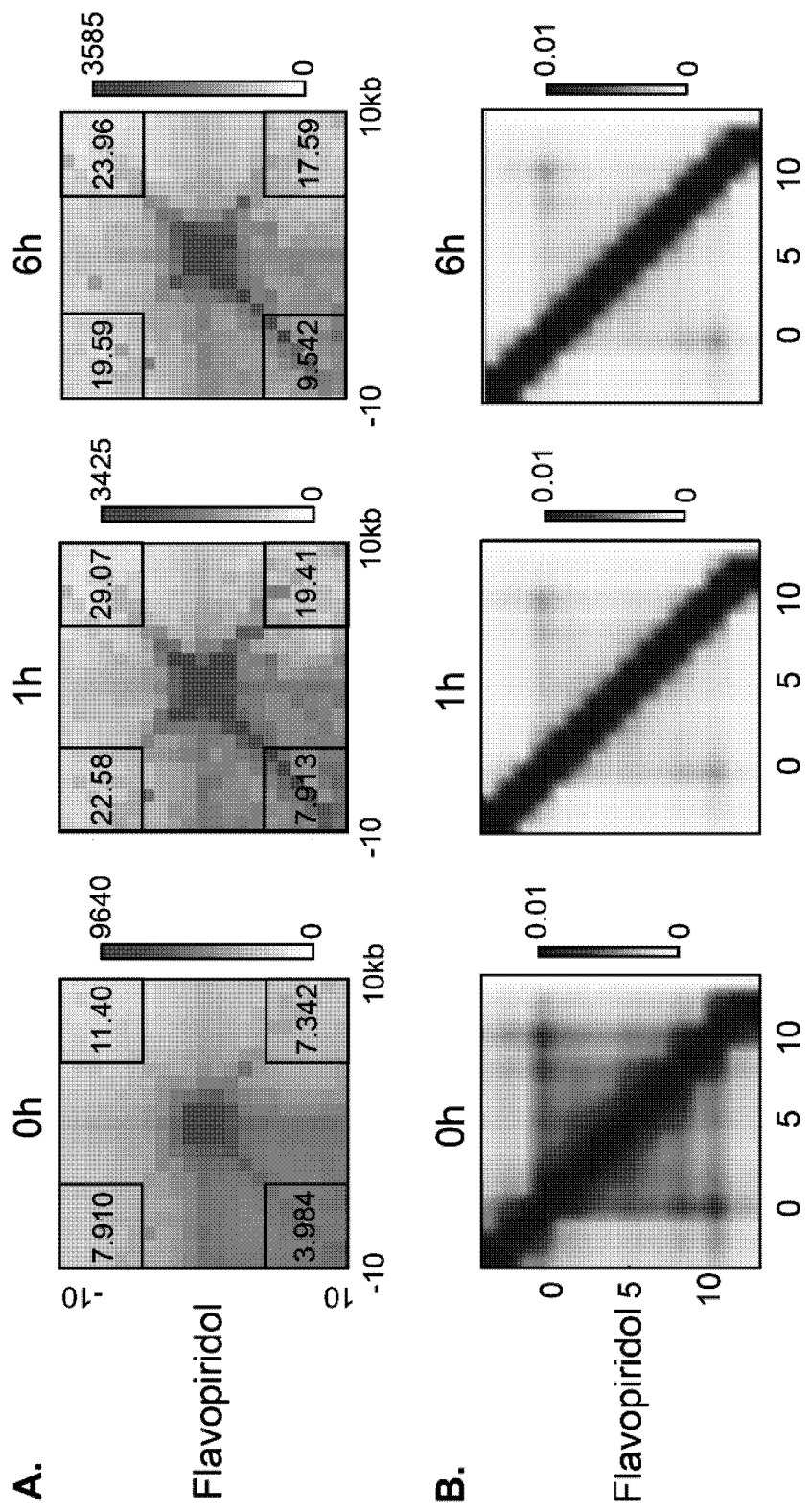
FIG. 19A-B

CHEMICAL PLATFORM ASSISTED PROXIMITY CAPTURE (CAP-C)

CROSS REFERENCE TO RELATED APPLICATIONS

This application is a national phase application under 35 U.S.C. § 371 of International Application No. PCT/US2019/031309 filed May 8, 2019, which claims the benefit of priority to U.S. Provisional Patent Application No. 62/668,543 filed May 8, 2018 and U.S. Provisional Patent Application No. 62/668,994 filed May 9, 2018, all of which are incorporated herein by reference in their entirety.

STATEMENT REGARDING FEDERALLY FUNDED RESEARCH

This invention was made with government support under R35GM124998, U54CA193419, and P01NS097206 awarded by the National Institutes of Health. The government has certain rights in the invention.

BACKGROUND OF THE INVENTION

A. Field of the Invention

The invention relates generally to the field of biochemistry and molecular biology. In particular, the compositions and methods are related to methods and compositions for capturing all or part of various molecules that are in the same physical proximity (proximity capture).

B. Background

Chromatin is one example of a biological complex targeted by current capture methodologies. In eukaryotes, DNA exists as compact, knot-free chromosomes in the nucleus. How chromosomes organize in the nucleus can influence transcription, DNA replication and other nuclear processes (Sexton et al., Cell 160:1049-59, 2015; Pombo and Dillon, Nat. Rev. Mol. Cell Biol. 16:245-57, 2015). Chromosome conformation capture (3C) approaches (such as 3C and its high-throughput derivative (Hi-C)) (Dekker et al., Science 295, 1306-11, 2002; Zhao et al., Nat. Genet. 38, 1341-47, 2006; Dostie et al., Genome research 16, 1299-1309, 2006; Lieberman-Aiden et al., Science 326, 289-93, 2009) have been widely used to study chromatin organization in different species and cell types. These methods and their variations employ formaldehyde-mediated crosslinking followed by in-situ enzymatic digestion and proximity ligation to infer spatial relationships between genomic loci. They have been instrumental in elucidating the principles of chromatin folding. Studies using these techniques have confirmed the existence of multiple layers of genome organization such as chromosome territories, compartments (Lieberman-Aiden et al., Science 326, 289-93, 2009), topologically associating domains (TADs) (Dixon et al., Nature 485, 376-80, 2012), sub-TADs (Phillips-Cremins et al., Cell 153, 1281-95, 2013), insulated neighborhoods (Dowen et al., Cell 159, 374-87, 2014), and chromatin loops (Rao et al., Cell 159, 1665-80, 2014).

Some of these chromatin features are strongly dependent on the resolution of the current 3C technologies. The sub-megabase scale chromosomal domains termed TADs (median: 880 Kb) identified in previous low-resolution Hi-C maps of mammalian cells (Dixon et al., Nature 485, 376-80, 2012), are in stark contrast to the contact domains (median: 185 Kb) obtained from high-resolution Hi-C maps (Rao et al., Cell 159, 1665-80, 2014). It is still unclear whether all domains form hierarchies with nested domains that are subsequently revealed as map-resolution increases, or whether a series of small domains with irreducible length identified in a high-resolution map co-aggregate and establish a large domain in low-resolution maps. Currently, only a handful of high resolution Hi-C datasets for mammalian mouse and human genomes (Rao et al., Cell 159, 1665-80, 2014; Bonev et al., Cell 171, 557-72.e524), with map resolutions around 1 Kb, are available to address these questions. Mechanisms leading to domain formation are only just starting to be elucidated (Rowley et al., Mol. Cell 67, 837-52, 2017; Hug et al., Cell 169, 216-28, 2017; Bonev et al., Cell 171, 557-72, 2017; Fudenberg et al., Cell reports 15, 2038-49, 2016). Hence, there has been a concerted effort to push past the 1 Kb resolution limit, such as by fragmenting the genome into smaller uniform units (Hsieh et al., Nat. Methods 13, 1009-11, 2016; Hsieh et al., Cell 162, 108-19, 2015; Ma et al., Nat. Methods 12, 71-78, 2015). However, a recurring limitation of 3C type approaches is partial digestion. All current 3C methods rely on formaldehyde-mediated crosslinking, which creates extensive covalent linkages of protein-protein and protein-DNA in chromatin. These crosslinks can mask certain restriction sites and prevent their full digestion. The ligation of partially digested fragments leads to an imprecise inference of their actual genomic proximity. New crosslinking strategies, which can ideally expose all potential restriction sites, are required to ubiquitously capture proximal contacts at all length scales.

Furthermore, although general principles describing the spatial conformation of mammalian chromosomes are emerging, critical gaps in the understanding of chromatin structure remain, especially regarding how domains form. An appealing model of loop extrusion was proposed based on numerous results obtained by applying 3C methods, which showed that Ctcf and cohesin loops help to bring distant DNA loci into proximity (Fudenberg et al., Cell reports 15, 2038-49, 2016). However, this model only explains some of the observations given that a large proportion of domains at high resolution do not form loops at their boundaries (Rao et al., Cell 159, 1665-80, 2014). In addition, recent studies investigating the consequences of acute cohesin loss (Schwarzer et al., Nature 551, 51-56, 2017; Rao et al., Cell 171, 305-20, 2017) indicated that two independent mechanisms compact chromatin: (i) a cohesin-dependent loop extrusion mechanism compacts chromatin locally and (ii) a cohesin-independent mechanism spatially segregates the genome into active and inactive compartments at a smaller scale than previously appreciated. These results strongly implicate an alternative mechanism that correlates the chromatin structure with transcription, which might play an important role in shaping the chromatin landscape.

There remains a need for additional compositions and methods for identifying and evaluating the physical proximity and structure of various molecular complexes and entities.

SUMMARY OF THE INVENTION

Chromatin conformation capture (3C) technologies have revolutionized the understanding of chromatin architecture, uncovering the principles of genome organization at varying length-scales. These methods rely on formaldehyde-mediated crosslinking followed by in-situ enzymatic digestion and proximity ligation to infer spatial relationships between genomic loci. The compositions and methods described here introduce Chemical-crosslinking Assisted Proximity Capture (CAP-C), a method that can directly assess spatial distances between nuclear genomic sequences with the use of different chemical cross-linkers of defined character and lengths. Compared to standard 3C-based methods, CAP-C can reveal finer details of promoter-enhancer interactions and chromatin domains at high resolution due to the design of the capture agent and the defined character of the cross-linking.

Certain embodiments are directed to methods for capture of elements in physical proximity using a capture agent. In certain aspects the methods comprise (a) contacting a "target biomolecule(s)," also referred to herein as a "target," with a functionalized scaffold or capture agent that comprises activatable cross-linking moieties to form a target/scaffold mixture; (b) exposing the target/scaffold mixture to an activator to activate the cross-linking moieties associated with the target/scaffold forming a cross-linked target/scaffold complex; (c) isolating the cross-linked target/scaffold complexes; and (d) identify portions of the target or targets that are cross-linked with the scaffold. The term "target biomolecule(s)" or "target" as used herein includes molecules in general which may be synthesized, metabolized or accumulated in vivo and may be associated with one or more other biomolecule(s) in a biomolecular complex (e.g., chromatin, RNA interactome, protein complexes, protein/nucleic acid complexes, etc.). Examples of such biomolecules include nucleic acids such as DNA and RNA; peptides; proteins; lipid-protein complexes; and various molecular complexes containing one or more biomolecule. In addition, for example, the biomolecule may exist on the surface of a cell membrane; may exist inside the cell; or may exist in both inside and outside the cell by penetrating the cell membrane, like a receptor. The term "proximity" or "physical proximity" refers to two elements having a certain spatial distance between elements (e.g., nucleic acids), distance can be determined in three-dimensional space between the two target elements. For example, DNA sequence elements in a chromosome that are close (e.g., within about 10, 50, 100, 150, 200, or 250 bp or more) in primary sequence are always in close proximity to each other in a linear context. In some cases, DNA sequence elements that are distant in primary sequence in a chromosome (e.g., separated by more than about 300, 400, 500, 1000, 1500, 2000, 5000, 10,000, 25,000, 50,000, 100,000, 250,000, 500,000, or 1,000,000 bp) can be in close proximity to each other due to the tertiary or quaternary structure of the chromosome(s). In some cases, targets that lie on different chromosomes can be in close proximity to each other due to the quaternary structure of the chromosomes. In certain aspects physical proximity as used herein refers to distance of 1, 10, 20, 30, 40, 50, 60, 70, 80, 90, 100 110, 120, 130, 140, 150, 200, 250, 300, 350, 400 nanometer (nm) or less. A target for capture can be all or part of a molecular complex comprising one or more nucleic acids, one or more polypeptides, or one or more nucleic acids and one or more polypeptides.

In certain aspects the functionalized scaffold or capture agent is an entity of defined size having at least or at most 2, 3, 4, 5, 6, 7, 8, 9, 10 or more functional groups that can be coupled to an arm or linker. Functional groups include reactive groups and cross-linkers. Functional groups include, but are not limited to maleimide groups, thiol reactive groups, amino groups such as primary and secondary amines, carboxyl groups, hydroxyl groups, aldehyde groups, alkyne groups, azide groups, carbonyls, haloacetyl (e.g., iodoacetyl) groups, imidoester groups, N-hydroxysuccinimide esters, sulfhydryl groups, pyridyl disulfide groups, and the like. It is specifically contemplated that one or more of these functional groups may be excluded in particular embodiments set forth herein. The arm or linker coupled to the functional group can be about, at least or at most about 0.5, 1, 10, 20, 30, 40, 50, 60, 70, 80, 90, 100, 150, 200 pm (or any range derivable therein). In particular aspects the scaffold or capture agent is a dendrimer or a nanoparticle. A nanoparticle can be a silicon nanoparticle, a silicon dioxide nanoparticle, metallic (e.g., gold) nanoparticle, or quantum dot. In certain aspects the scaffold or capture agent has an effective diameter or a maximal distance between functional groups of about 1, 5, 10, 50, 100, 200, 250, 300, 350, 400, to about 450 nm (and any range derivable therein). An effective diameter is the length between functional groups that is indicative of the physical distance between two targets that are capable of reacting or interacting with the capture agent. In certain aspects the arm/functional group is positioned on the capture agent at an angle of 0.5 to 180 degrees relative to each other respective to the center point or center of mass of a capture agent, including all angles there between. The capture agent does not need to be spherical or circular, but in some instances are substantially spherical or circular.

In certain aspects the functionalized scaffold or capture agent can further comprise at least two of the same functional groups, or at least a first functional group and at least a second, third, fourth or more functional group(s). A functional group can be a cross-linking moiety, a label, a tag, or a second crosslinking moiety. A label can be enzyme labels, such as, glucose oxidase; radioisotopes, such as iodine ($^{131}$I, $^{125}$I, $^{123}$I, $^{121}$I) ($^{14}$C), sulfur ($^{35}$S), tritium ($^{3}$H), indium ($^{115m}$In, $^{113m}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$SC, $^{186}$Re, $^{188}$Re, $^{142}$Pr, $^{105}$Rh, $^{97}$Ru; luminol; and fluorescent labels, such as fluorescein and rhodamine, and biotin or other affinity labels. In certain aspects the label is an imaging agent. The cross-linking moiety can be a protein cross-linking moiety, an RNA cross-linking moiety, or a DNA cross-linking moiety, or combinations thereof. In certain aspects the functionalized scaffold or capture agent is coupled to one or more CRISPR sequences or antibodies.

In certain instances, a cross-linker activator is light, temperature, pH or other condition. The light can be or includes ultraviolet light. In particular aspects, the light has a wavelength of about 350 to 375 nm, more particularly the light can comprise a wavelength of 365 nm. In certain aspects the cross-linking activator is temperature change, e.g., functional groups are not sufficiently active at room temperature but are activated at higher temperatures, for example, above 37° C. In other aspects the cross-linking activator is pH, e.g., a cross-linker may not be effective at a basic or neutral pH but is activated at an acidic pH.

In certain aspects isolating the target/scaffold or capture agent complexes further comprises exposing the target/scaffold or capture agent complex to a proteinase, a nuclease, a biotin-protein ligase enzyme, or other enzyme or condition forming a treated target/scaffold or capture agent complex. In certain aspects the treated target/scaffold or capture agent complex can be a fragment or subpart of a larger complex or structure. The method can further comprise precipitating or isolating the treated target/scaffold or capture agent complexes forming an isolated target/scaffold or capture agent complex. In certain aspects precipitating or isolating further comprises contacting the treated target/ scaffold or capture agent complex with an affinity agent or an affinity agent ligand. The affinity agent or affinity agent ligand can be an antigen, an antibody, an oligonucleotide probe, or an oligonucleotide primer. Isolating the target/scaffold or capture agent complexes can further comprise fragmenting the target associated with a treated target scaffold or capture agent complex, and ligating or modifying the resulting fragments.

Fragmenting a target or a treated target/scaffold or capture agent complex can include nuclease digestion. In certain aspects the nuclease is an endonuclease or exonuclease. In certain aspects the exonuclease is micrococcal nuclease (MNase). In other aspects the endonuclease can be a restriction endonuclease. In certain instances, the endonuclease is MboI, Sau3AI, DpnII, BfuCI, MluCI, HpyCH4IV, AluI, FatI, NlaIII, CviAII, AciI, HpaII, MspI, MnlI, or BstUI. The method can include modifying the resulting fragments (e.g., nucleic acids, peptides, etc.) comprises conjugating a fragment to a probe, primer, or other label. In certain aspects isolating the target/scaffold or capture agent complexes further comprises fragmenting the target and ligating a bivalent linker or an affinity tag to the target fragment crosslinked to the scaffold. Isolating the target/scaffold or capture agent complexes can also include contacting the target/scaffold or capture agent complex with an affinity agent that specifically binds a component or portion of the target.

Particular embodiments are directed to capture of DNA-DNA or chromatin containing complexes. In certain aspects the target comprises DNA or is chromatin. In particular aspects the chromatin is in situ. The chromatin can be in a cell or a cell nucleus. The cell can be a diseased or pathologic cell. In certain aspects cell is a cancer cell. The method can further comprise fixing the cell prior to contacting the cell with functionalized scaffolds or capture agents. The cell can be fixed with formaldehyde or other appropriate cell fixative. In certain aspects the method can further comprise unfixing the cell after formation of target/scaffold or capture agent complexes. A cell of the invention may be derived from a biological sample. As used herein, the term "biological sample" refers to a sample obtained from a subject. Any biological sample containing a cell is suitable. Numerous types of biological samples are known and may include, but are not limited to, tissue samples or bodily fluids. In some embodiments, the biological sample is a tissue sample such as a tissue biopsy. The tissue biopsy may be a biopsy of a known or suspected tumor. The biological sample may also be primary and/or transformed cell cultures derived from tissue from the subject. Non-limiting examples of suitable bodily fluids include blood, plasma, serum, and urine. Identifying a nucleic acid target can include sequencing a DNA target(s) isolated from target/scaffold or capture agent complexes.

Other embodiments are directed to the capture of RNA-DNA/RNA/protein targets. In certain aspects the target comprises RNA. RNA can be labeled with a nucleotide specific agent. In certain aspects the nucleotide specific is a modified kethoxal bearing a functional tag such as azide. The nucleotide specific agent can be further modified with a crosslinking moiety, such as azide. The functionalized scaffold or capture agent can contain photoactivatable crosslinking groups that crosslink to azide-modified kethoxal upon activation. The target can further comprise DNA and/or protein. In particular aspects the target is an RNA interactome.

Certain embodiments are directed to the capture of protein target(s). In certain aspects a target comprises a polypeptide.

The method can include identifying a polypeptide target or a fragment thereof by immunoblotting the targets or fragments thereof from the isolated target/scaffold or capture agent complexes.

Other embodiments are directed to chromatin assessment. A chromatin mapping or assessment method can include (a) contacting a chromatin target with a functionalized scaffold or capture agent to form a chromatin/scaffold or capture agent mixture; (b) exposing the chromatin/scaffold or capture agent mixture to light of an appropriate wavelength or other activation condition to activate the cross-linking moieties of the scaffold or capture agent and form a cross-linked chromatin/scaffold complex; (c) isolating the chromatin/scaffold complexes; and (d) identifying chromatin loci from the isolated chromatin/scaffold or capture agent complexes. In certain aspects the scaffold or capture agent is a dendrimer or nanoparticle. The scaffold or capture agent can have a diameter of 1, 10, 20, 30, 40, 50, 60, 70, 80, 90, 100, 150, 200, 250, 300, 350 to 400 nm, including values and ranges there between. In certain aspects the target is a chromatin associated molecular complex comprising one or more nucleic acids, one or more polypeptides, or one or more nucleic acids and one or more polypeptides. In certain aspects the chromatin is in situ. In particular aspects the chromatin is in a cell or a cell nucleus. The method can further comprise fixing the cell or cell nucleus prior to contacting the cell or cell nucleus with functionalized scaffold or capture agent. In certain aspects the cell or cell nucleus is fixed with formaldehyde or through other fixing approaches. The method can further comprise reverse-crosslinking the cell after formation of target/scaffold or capture agent complexes. In other aspects activating light is ultraviolet light. The light can have a wavelength of about 350 to 375 nm, in particular the light comprises a wavelength of 365 nm. In certain aspects isolating the target/scaffold or capture agent complexes further comprises exposing the target/scaffold or capture agent complex to a proteinase, a nuclease, or other enzyme forming a treated target/scaffold or capture agent complex. The method can further comprise precipitating or isolating the treated target/scaffold or capture agent complexes forming an isolated target/scaffold or capture agent complex. Isolating the target/scaffold or capture agent complex can further comprise fragmenting the target and conducting proximal ligation or modification of the resulting fragment(s). In certain aspects fragmenting the DNA target is by endonuclease or exonuclease digestion. In certain aspects isolating the target/scaffold or capture agent complexes further comprises fragmenting the target and ligating a bivalent linker to the target fragment that is crosslinked or bound to the scaffold or capture agent. Isolating the target/scaffold or capture agent complexes can further comprise contacting the target/scaffold or capture agent complex with an affinity agent that specifically binds a component or portion of the target. In certain aspects the affinity agent is a nucleic acid probe. DNA target(s) can be identified by sequencing the targets from the isolated target/scaffold or capture agent complexes. In certain aspects a polypeptide or fragment thereof in the target can be identified by immunoblotting or other peptide identification or sequencing methods.

Certain embodiments are directed to chromatin immunoprecipitation (ChIP) DNA sequencing to analyze protein interactions with DNA (ChIP-seq methods). In certain aspects a ChIP-seq method comprises (a) contacting a chromatin target with a functionalized scaffold or capture agent comprising activatable cross-linking moieties to form a chromatin target/scaffold or capture agent mixture, wherein the scaffold or capture agent is also coupled to an avidity tag; (b) exposing the chromatin target/scaffold or capture agent mixture to an activator to activate the cross-linking moieties of the scaffold or capture agent and form a cross-linked target/scaffold or capture agent complex forming a chromatin target complex; (c) contacting the chromatin target complex with an affinity agent that binds a chromatin associated protein, wherein the affinity agent is coupled to an avidity tag modification agent, wherein the avidity tag modification agent when brought in proximity to an avidity tag modifies the avidity tag forming an isolatable chromatin/scaffold or capture agent complex; (d) isolating the chromatin target/scaffold or capture agent complexes via the avidity tag; and (e) identify portions of nucleic acid associated coupled or linked with the isolatable chromatin/scaffold or capture agent complex. In certain aspects the avidity tag is a biotinylated substrate and the avidity tag modification agent is a biotin-protein ligase. In certain aspects a DNA crosslinking reagent can be used to associate DNA components. In certain embodiments multiple dendrimers carrying DNA (or RNA) crosslinkers are coupled to a specific antibody that recognizes a protein or histone marker of interest. The dendrimer can also be labeled or coupled to a tag or label, such as biotin. The cell is formaldehyde crosslinked, crosslinking DNA or RNA with proteins. The crosslinked cell lysate decorated with the antibodies coupled to the functional dendrimers, which are then subjected to a crosslinking activator. The antibody will recognize the protein in vitro and the dendrimers coupled to the antibody will crosslink to DNA or RNA bound by the protein (fixed by formaldehyde).

Certain embodiments are directed to chromatin crosslinking followed by DNA sequencing to analyze protein interactions with RNA (CLIP-seq methods). In certain aspects the method comprises (a) contacting a RNA-binding target or protein target in proximity to RNA with a functionalized scaffold or capture agent comprising activatable cross-linking moieties to form a target/scaffold or capture agent mixture, wherein the scaffold or capture agent is also coupled to an avidity tag; (b) exposing the target/scaffold or capture agent mixture to an activator to activate the cross-linking moieties of the scaffold or capture agent and form a cross-linked target/scaffold or capture agent complex; (c) contacting the target with an affinity agent that binds a RNA-binding protein or protein target in proximity to RNA, wherein the affinity agent is coupled to an avidity tag modification agent, wherein the avidity tag modification agent when brought proximity to an avidity tag modifies the avidity tag forming an isolatable chromatin/scaffold complex; (d) isolating the target/scaffold or capture agent complexes via the avidity tag; and (e) identify portions of the RNAs that are associated linked with the isolatable target/scaffold or capture agent complex. In certain aspects the avidity tag is a biotinylated substrate and the avidity tag modification agent is a biotin-protein ligase.

The terms "restriction endonuclease" or "restriction enzyme" refer to enzymes that cut DNA at or near specific recognition nucleotide sequences known as "restriction sites" or "restriction recognition sites." Restriction endonuclease includes both enzymes that are able to recognize and cut methylated DNA and enzymes that only recognize un-methylated DNA. Methylated DNA includes dam methylation, dcm methylation and CpG methylation. Restriction endonucleases may recognize four, six, or eight nucleotide long restriction sites. These types of restriction endonucleases are referred to a 4-cutters, 6-cutters, and 8-cutters respectively. In some embodiments, a restriction endonuclease can be one of the following: AclI, HindIII, SspI, MluCI, PciI, AgeI, BspMI, BfuAI, SexAI, MluI, BceAI, HpyCH4IV, HpyCH4III, BaeI, BsaXI, AflIII, SpeI, BsrI, BmrI, BglII, AfeI, AluI, StuI, ScaI, ClaI, BspDI, PI-SceI, NsiI, AseI, SwaI, CspCI, MfeI, Nb.BssSI, BssSaI, BmgBI, PmlI, DraIII, AleI, EcoP15I, PvuII, AlwNI, BtsIMutI, NdeI, FatI, NlaIII, CviAII, MslI, FspEI, XcmI, BstXI, PflMI, BccI, NcoI, BseYI, FauI, XmaI, TspMI, SmaI, Nt.CviPII, LpnPI, AciI, SacII, BsrBI, HpaII, MspI, ScrFI, StyD4I, BsaJI, BslI, BtgI, NeiI, AvrII, MnlI, Nb.BbvCI, BbvCI, Nt.BbvCI, SbfI, Bpu10I, Bsu36I, EcoNI, HpyAV, BstNI, PspGI, StyI, BegI, PvuI, BstUI, EagI, RsrII, BsiEI, BsiWI, BsmBI, Hpy99I, MspA1I, MspJI, SgrAI, BfaI, BspCNI, PaeR7I, XhoI, EarI, AcuI, PstI, BpmI, DdeI, SfcI, AflII, BpuEI, SmlI, BsoBI, AvaI, MboII, BbsI, XmnI, Nb.BsmI, BsmI, EcoRI, HgaI, ZraI, AatII, PflFI, Tth111I, PshAI, AhdI, DrdI, Eco53kI, SacI, BseRI, MlyI, PleI, Nt.BstNBI, HinfI, EcoRV, MboI, Sau3AI, DpnII, BfuCI, DpnI, BsaBI, TfiI, BsrDI, Nb.BsrDI, BbvI, BtsaI, Nb.BtsI, BstAPI, SfaNI, SphI, SrfI, NmeAIII, NaeI, NgoMIV, BglI, AsiSI, BtgZI, HinP1I, HhaI, BssHII, NotI, Fnu4HI, Cac8I, MwoI, BmtI, NheI, BspQI, SapI, Nt.BspQI, BlpI, ApeKI, TseI, Bsp1286I, Nt.AlwI, AlwI, BamHI, BtsCI, FokI, HaeIII, FseI, SfiI, NarI, KasI, PluTI, SfoI, AscI, EciI, BsmFI, PspOMI, ApaI, Sau96I, NlaIV, Acc65I, KpnI, BsaI, HphI, BstEII, AvaII, BanI, BaeGI, BsaHI, BanII, RsaI, CviQI, BstZ17I, BciVI, SalI, BsmAI, BcoDI, Nt.BsmAI, ApaLI, BsgI, AccI, Hpy166II, Tsp45I, HpaI, PmeI, HincII, BsiHKAI, TspRI, ApoI, NspI, BsrFaI, BstYI, HaeII, CviKI-1, EcoO109I, PpuMI, I-CeuI, SnaBI, I-SceI, BspHI, BspEI, MmeI, TaqaI, NruI, Hpy188I, Hpy188III, XbaI, BclI, HpyCH4V, FspI, PI-PspI, MscI, BsrGI, MseI, PacI, PsiI, BstBI, DraI, PspXI, BsaWI, BsaAI, or EaeI.

The term "nucleic acid" as used herein can refer to the nucleic acid material itself and is not restricted to sequence information (i.e., the succession of letters chosen among the five base letters A, C, G, T, or U) that biochemically characterizes a specific nucleic acid, for example, a DNA or RNA molecule. Nucleic acids described herein are presented in a 5'→3' orientation unless otherwise indicated.

As used herein, the term "polynucleotide" refers to polymers of natural nucleotide monomers or analogs thereof, including double and single stranded deoxyribonucleotides, ribonucleotides, α-anomeric forms thereof, and the like. The terms "polynucleotide", "oligonucleotide" and "nucleic acid" are used interchangeably. Usually the nucleoside monomers are linked by internucleotide phosphodiester linkages, whereas used herein, the term "phosphodiester linkage" refers to phosphodiester bonds or bonds including phosphate analogs thereof, and include associated counterions, including but not limited to H+, NH4+, NR4+, Na+, if such counterions are present. A polynucleotide may be composed entirely of deoxyribonucleotides, entirely of ribonucleotides or a mixture thereof.

"RNA" refers to ribonucleic acid and is a polymeric molecule implicated in various biological roles in coding, decoding, regulation, and expression of genes. RNA plays an active role within cells by catalyzing biological reactions, controlling gene expression, or sensing and communicating responses to cellular signals. Messenger RNA carries the information for the amino acid sequence of a protein to a ribosome, through which it is translated that the protein synthesized.

The term "click chemistry" refers to a chemical philosophy introduced by K. Barry Sharpless, describing chemistry tailored to generate covalent bonds quickly and reliably by joining small units comprising reactive groups together.

Click chemistry does not refer to a specific reaction, but to a concept including reactions that mimic reactions found in nature. In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. A distinct exothermic reaction makes a reactant "spring loaded". In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallization or distillation).

The term "click chemistry handle," as used herein, refers to a reactant, or a reactive group, that can partake in a click chemistry reaction. For example, an azide is a click chemistry handle. In general, click chemistry reactions require at least two molecules comprising complementary click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein. Other suitable click chemistry handles are known to those of skill in the art.

As used herein, the term "tag" or "affinity tag" refers to a moiety that can be attached to a compound, nucleotide, or nucleotide analog, and that is specifically bound by a partner moiety. The interaction of the affinity tag and its partner provides for the detection, isolation, etc. of molecules bearing the affinity tag. Examples include, but are not limited to biotin or iminobiotin and avidin or streptavidin. A sub-class of affinity tag is the "epitope tag," which refers to a tag that is recognized and specifically bound by an antibody or an antigen-binding fragment thereof. Examples of suitable tags include, but are not limited to, amino acids, peptides, proteins, nucleic acids, polynucleotides, sugars, carbohydrates, polymers, lipids, fatty acids, and small molecules. Other suitable tags will be apparent to those of skill in the art and the invention is not limited in this aspect. In some embodiments, a tag comprises a sequence useful for purifying, expressing, solubilizing, and/or detecting a target. In some embodiments, a tag can serve multiple functions. In some embodiments, a tag comprises an HA, TAP, Myc, 6×His, Flag, or GST tag, to name few examples. In some embodiments, a tag is cleavable, so that it can be removed. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

Other embodiments of the invention are discussed throughout this application. Any embodiment discussed with respect to one aspect applies to other aspects as well and vice versa. Each embodiment described herein is understood to be embodiments that are applicable to all aspects. It is contemplated that any embodiment discussed herein can be implemented with respect to any method or composition, and vice versa. Furthermore, compositions and kits can be used to achieve methods disclosed herein. Any method set forth herein may be recited in "use" format.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used according to its plain and ordinary meaning in the areas of biochemistry and material science to indicate that a value includes the standard deviation of error for the device or method being employed to determine the value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that embodiments described in the context of the term "comprising" may also be implemented in the context of the term "consisting of" or "consisting essentially of."

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the compositions and methods. Certain embodiments may be better understood by reference to one or more of these drawings in combination with the detailed description of the specification.

μg/ml α-amanitin for 6 h and 12 h; directionality indices (DI) as well as inhibitor-treated vs control delta maps also indicate the weakening of boundaries and loss of intra-domain interactions respectively. A representative example of a loop shows it being present but weakened over time as the domain is lost. (B) Domains were called by Arrowhead and loops were called by HiCCUPS. Bar chart shows that domains are totally disappeared while loops are reduced. (C) Aggregate peak analysis (APA) for control, 6 h and 12 h α-amanitin treated samples indicates the presence of loops. APA was performed using the set of confident peaks called from deep-sequenced CAP-C on the lower-resolution inhibitor maps. Values greater than 1 in the bottom-left box indicate the presence of loops. APA scores (Enrichment of mean signal at peak foci over the mean signal in the lower-left corner) are also greater in α-amanitin-treated samples over control, indicating that the loss of domains during transcription inhibition is greater than the attenuation of loops. (D) Meta-loop analysis shows the widespread loss of domains and the presence of weakened loops. Peaks called in both control and inhibitor maps were overlapped with domains in control to yield 103-263 loop-domains with a medium length of 170 Kb for meta-analysis. Mean map of α-amanitin-treated samples, with distances re-scaled into 10 bins, were shown as an example. (E) Contact probability of the mean maps quantifying results in (D) shows: (1) an increase of contacts at the diagonals and decrease of contacts in bins 2-7 between control and α-amanitin-treated samples; and (2) a corresponding increase in contacts of inhibitor-treated samples at the corners of all loop-domain. This is contrasted with a lack of increase at the corners of both non-loop domains and randomly permutated domains, suggesting the presence of an attenuated loop.

Figure 6A:
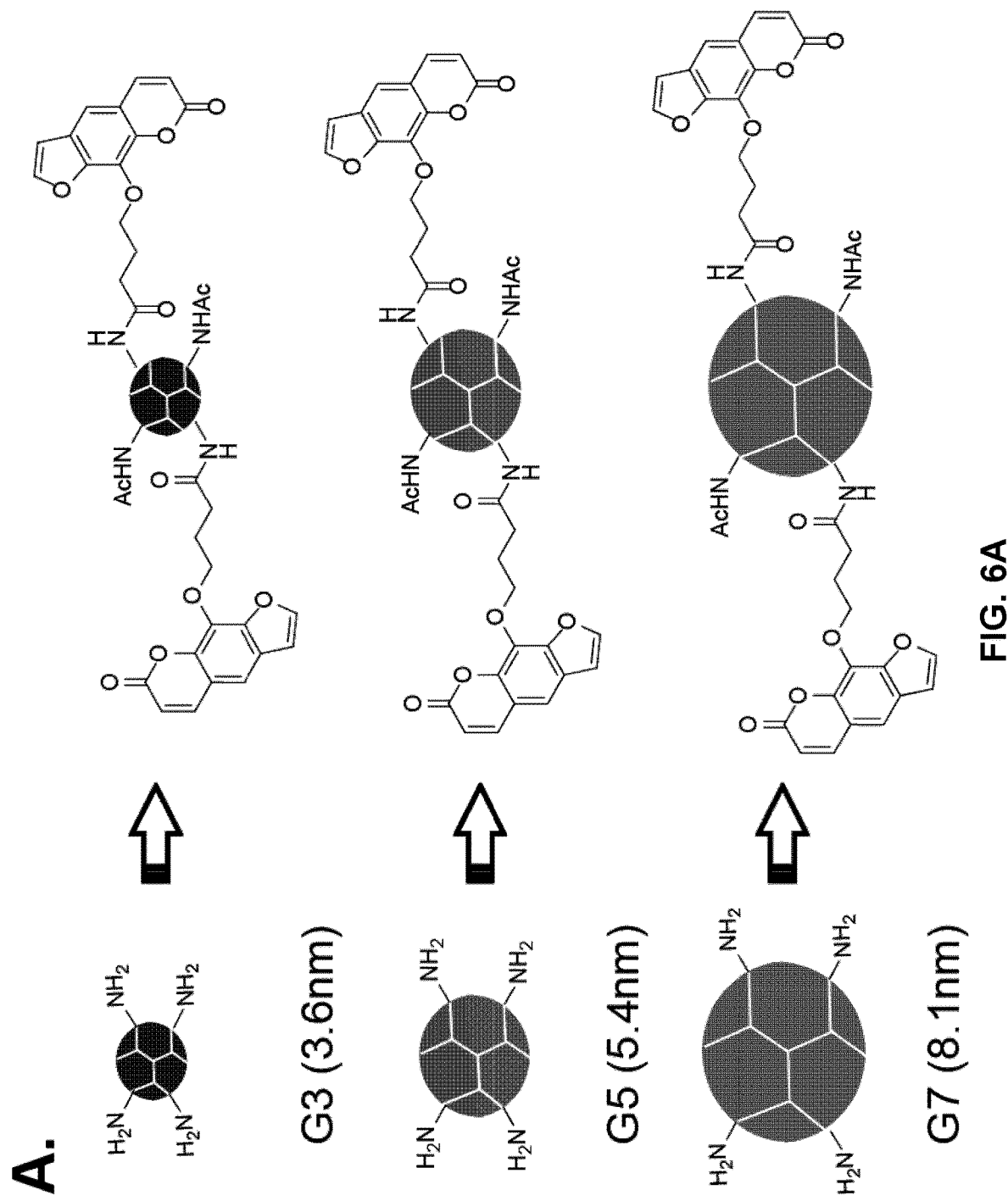
Figure 6B:
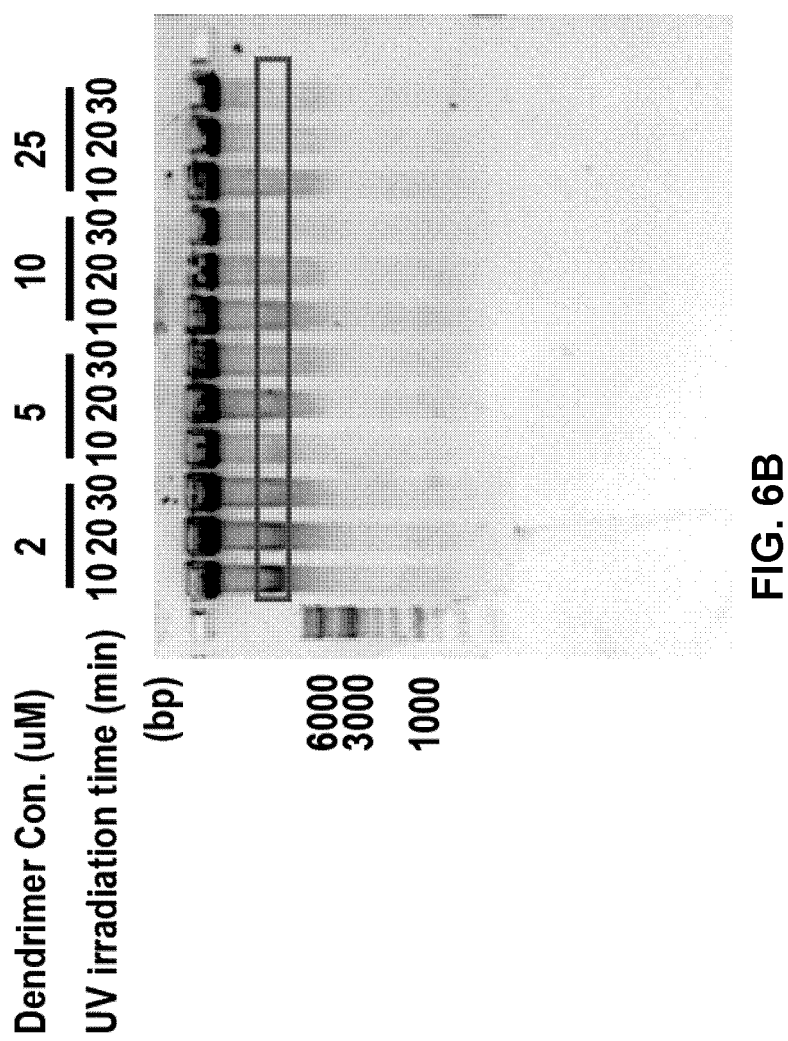

FIGS. 6A-B. Validation of photo-crosslinking between psoralen-modified PAMAM dendrimers and purified genomic DNA in vitro. (A) Generations of 3, 5 and 7 PAMAM dendrimers with surface amines were shown as balls in blue red and green, respectively. The diameters for each type of dendrimers are shown below. For each generation of dendrimers, half of the terminal amine branches are modified with psoralen while the rest are blocked with acetyl group. (B) Psoralen-functionalized dendrimer G3 was serial diluted to 25, 10, 5, 2 μM and mixed with 10 μg genomic DNA, respectively. Each mixture was exposed under UV irradiation 10, 20 or 30 minutes. The crosslinked complexes were analyzed on agarose gel. Red box indicates the position of genomic DNA. DNA-dendrimer complexes were characterized as a band shift to the top.

Figure 7A:
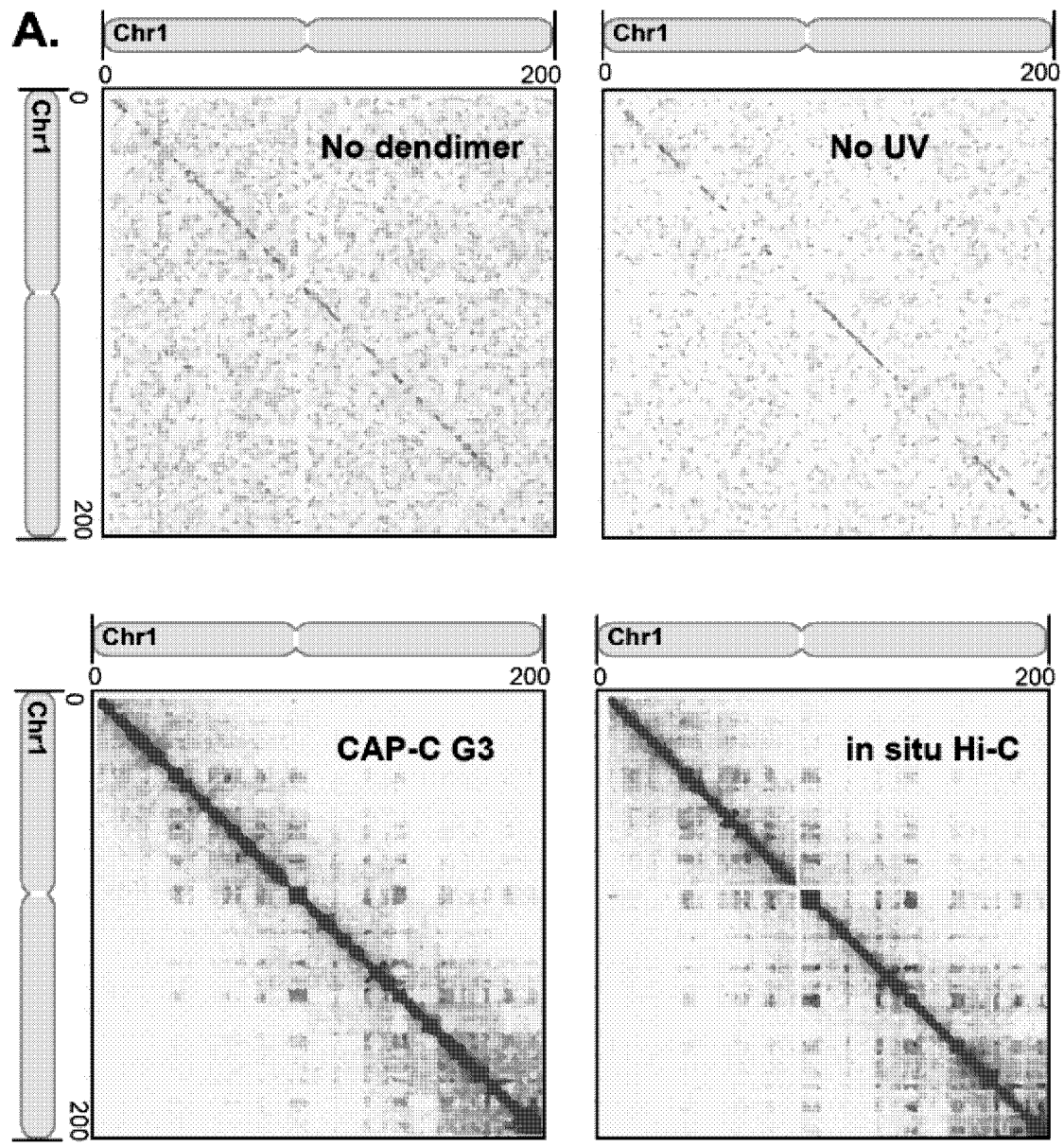
Figure 7B:
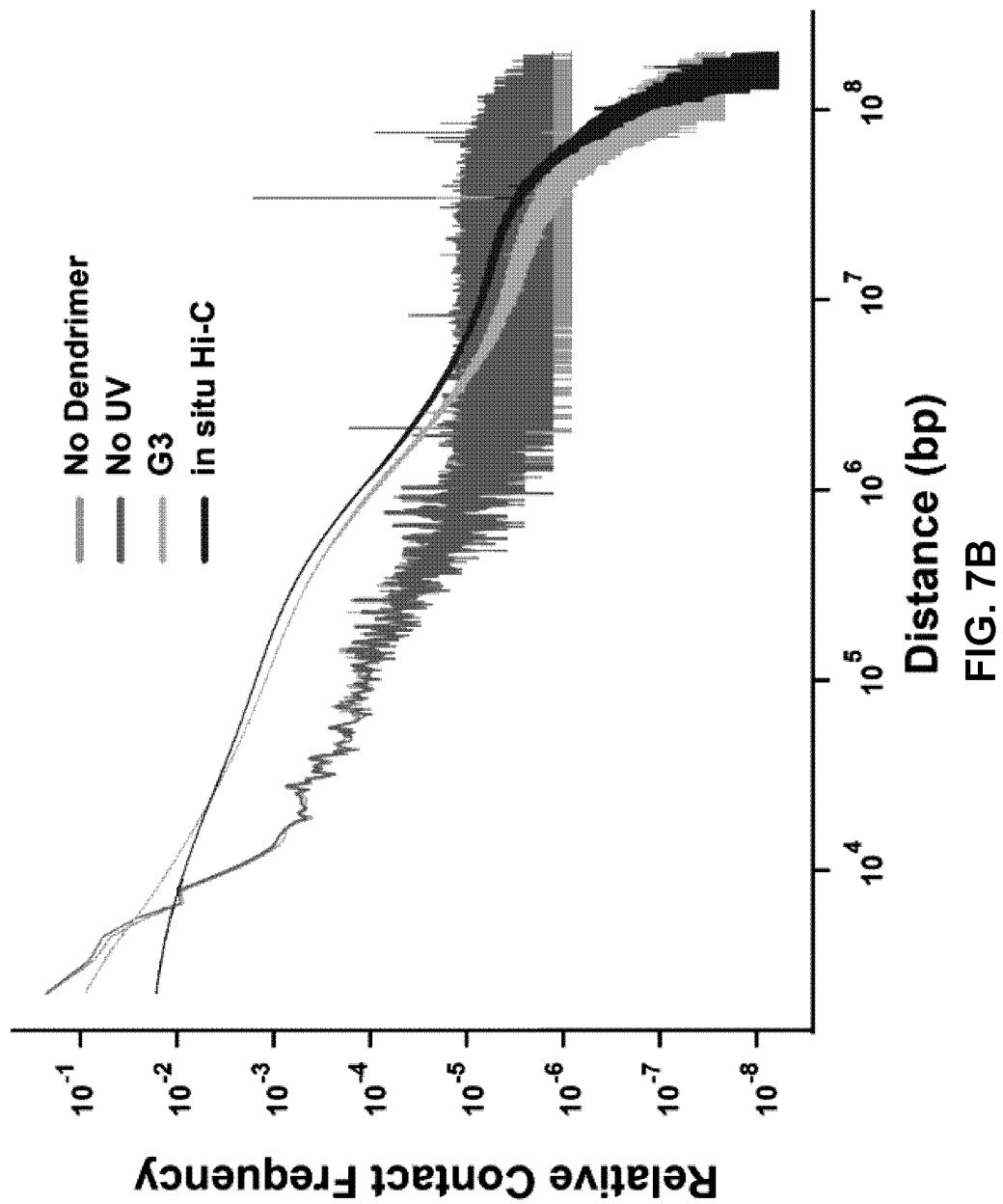

FIGS. 7A-B. Validation of the CAP-C method. Long-range contacts were lost without initiating the chemical-assisted UV crosslinking. (A) 500 Kb resolution contact maps of chromosome 1 are shown for in situ Hi-C under different conditions of "G3 CAP-C". No dendrimer: experiment was performed without introducing psoralen functionalized dendrimer; No UV: experiment was performed in the presence of psoralen-modified G3 dendrimer but without UV irradiation to crosslink chromatin; CAP-C G3: CAP-C was performed with addition of psoralen-modified G3 dendrimer; in situ Hi-C was performed as previously described. (B) Relative frequency vs genomic distance curve generated from low resolution maps show that "No dendrimer" and "No UV" conditions fail to crosslink chromatin at long-range genomic distances over 10 kB while "CAP-C G3" showed similar long-range patterns typically seen in in situ Hi-C.

Figure 8:
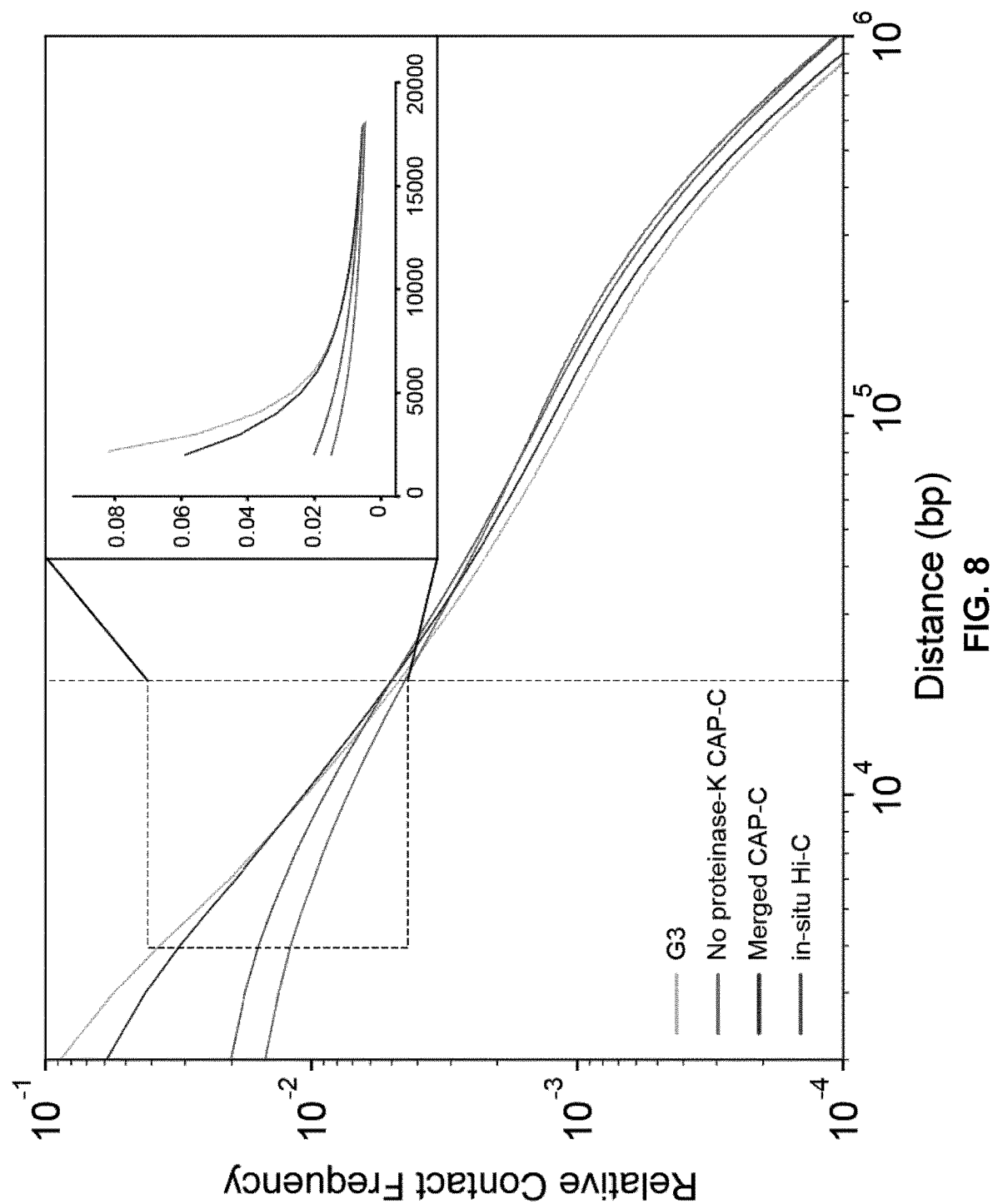

FIG. 8. Short length contacts could not be enriched in CAP-C without protease treatment. Relative contact frequency vs distance was plotted for 10 μM G3 CAP-C, 10 μM G3 CAP-C without proteinase K (no proteinase-K treated CAP-C), merged CAP-C, and in-situ Hi-C, respectively. The inventors observed that in the absence of proteinase-K treatment, G3 CAP-C (green vs yellow) did not exhibit an enrichment of short-range contacts, and was similar to the frequency-distance curve of in-situ Hi-C (green vs red), suggesting that short-range contacts could not be enriched without protease treatment.

Figure 9A:
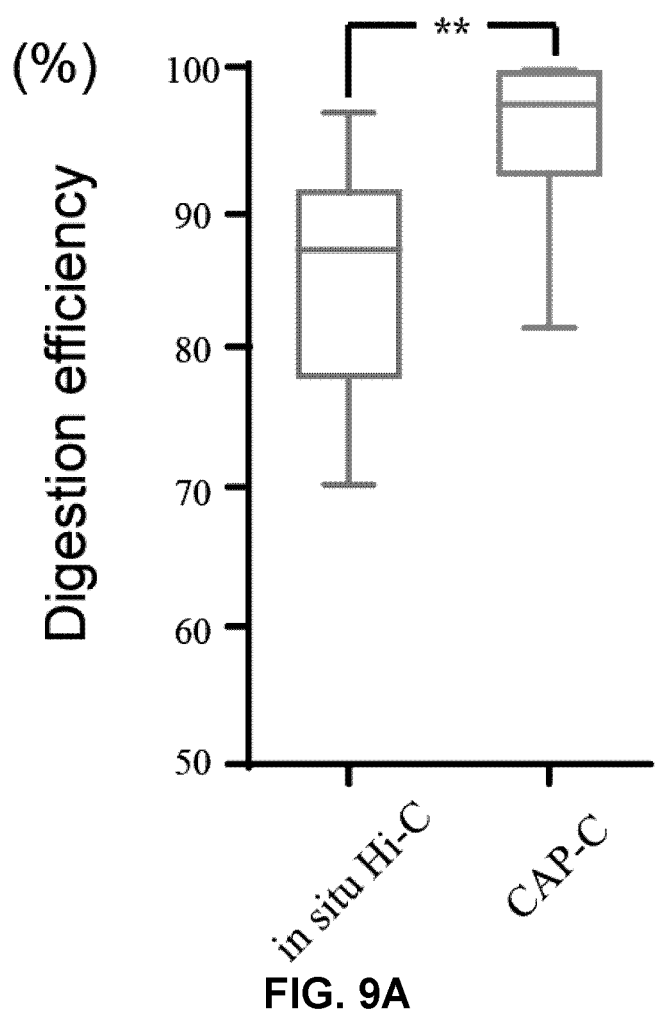
Figure 9B:
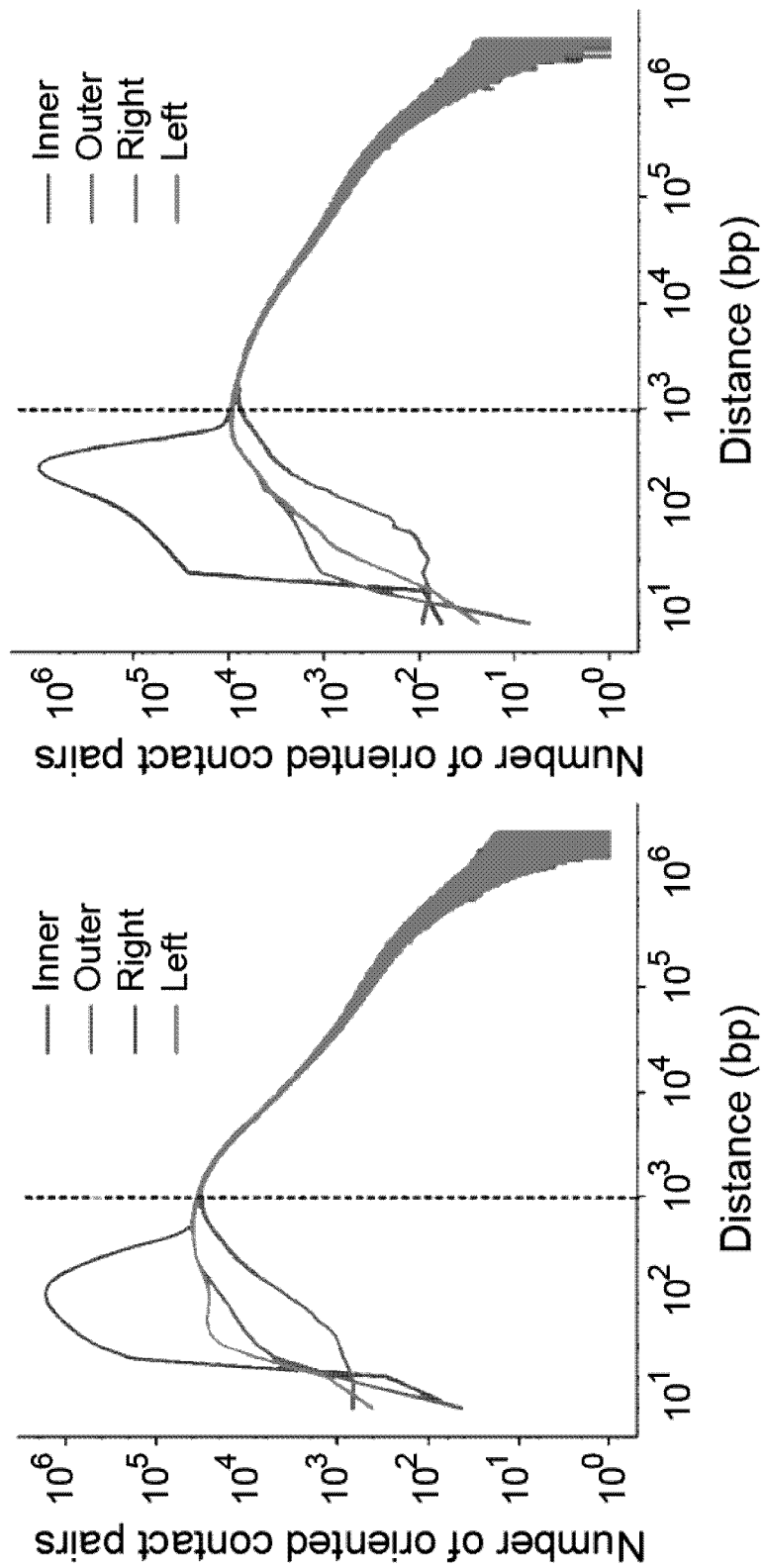

FIGS. 9A-B. Digestion efficiency and strand orientation analysis between CAP-C and in-situ Hi-C. (A) CAP-C shows higher MboI digestion efficiency over in situ Hi-C. Primers were designed by mapping to upstream and downstream MboI recognition sites within 200 bp. The digestion efficiency was analyzed by qPCR of MboI fragmented DNA which followed the standard protocol of CAP-C and in situ Hi-C. (B) Strand orientation analysis revealed that contacts above 1 Kb are legitimate ligation products in both merged CAP-C and in-situ Hi-C. "Inner": inward strand configuration; "Outer": outward strand configuration; "Right", "Left": same strand configuration.

Figure 10A:
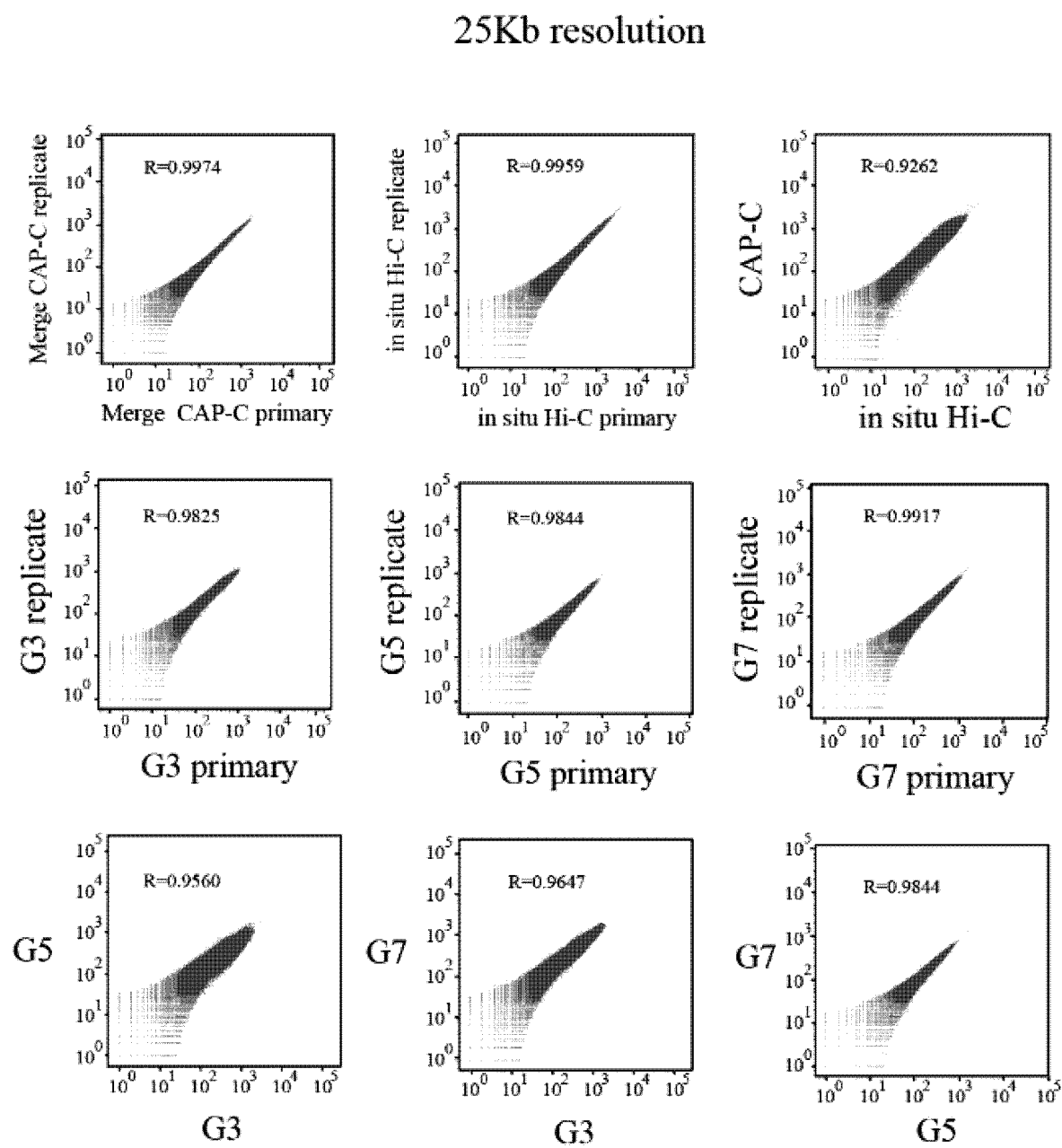
Figure 10B:
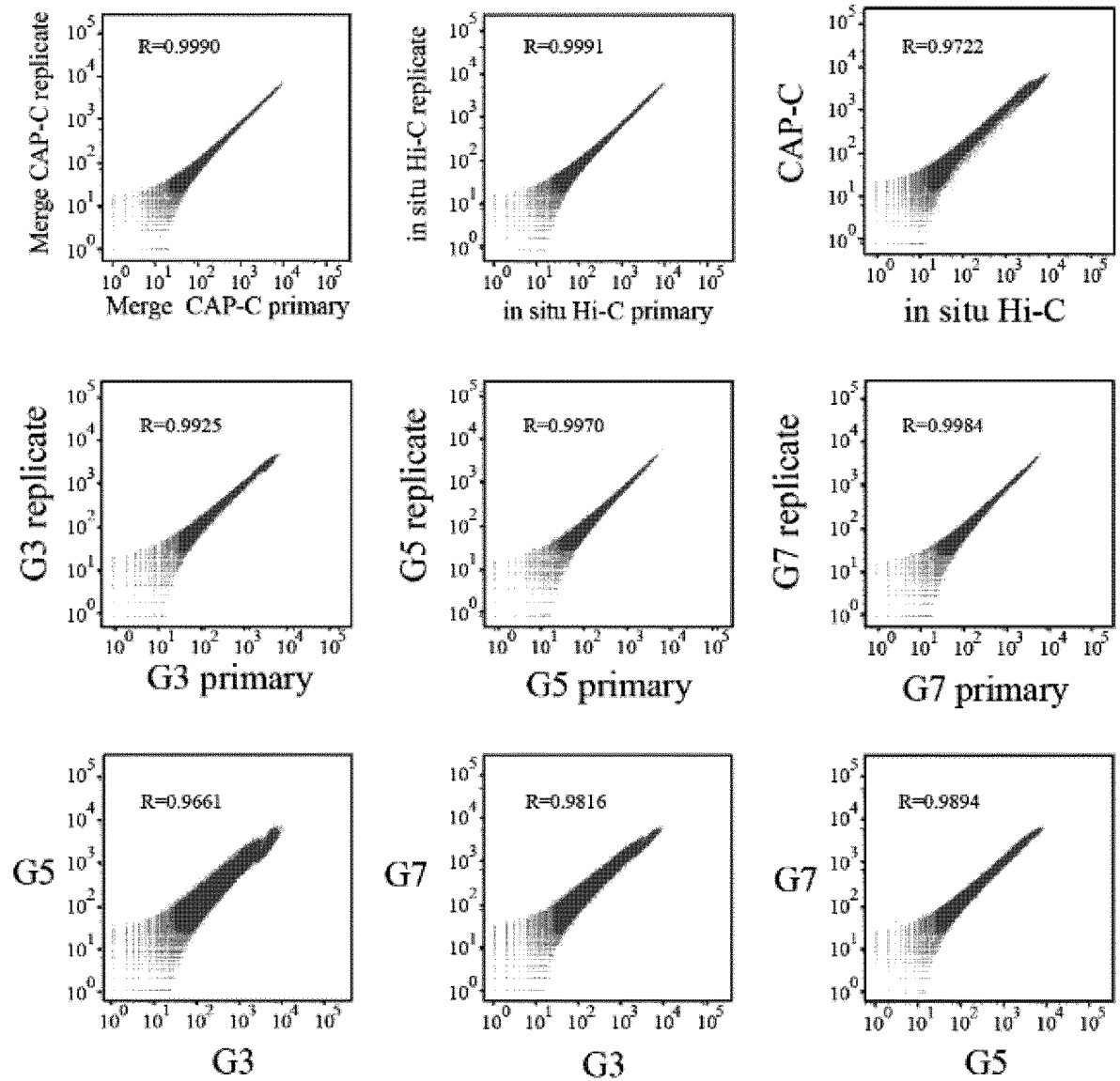

FIGS. 10A-B. Reproducibility of CAP-C and in-situ Hi-C experiments. Pearson's correlation analyses were performed for contact matrices binned at 25 Kb and 100 Kb resolution and visualized in log-scale. First row: Comparisons made between primary and biological replicate of merged CAP-C (column 1), in-situ Hi-C (column 2) followed by one between merged CAP-C and in-situ Hi-C (column 3). Second row: Comparisons made between primary and biological replicates of CAP-C G3 (column 1), G5 (column 2) and G7 (column 3). Third row: Cross comparisons between CAP-C experiments using different dendrimers.

Figure 11:
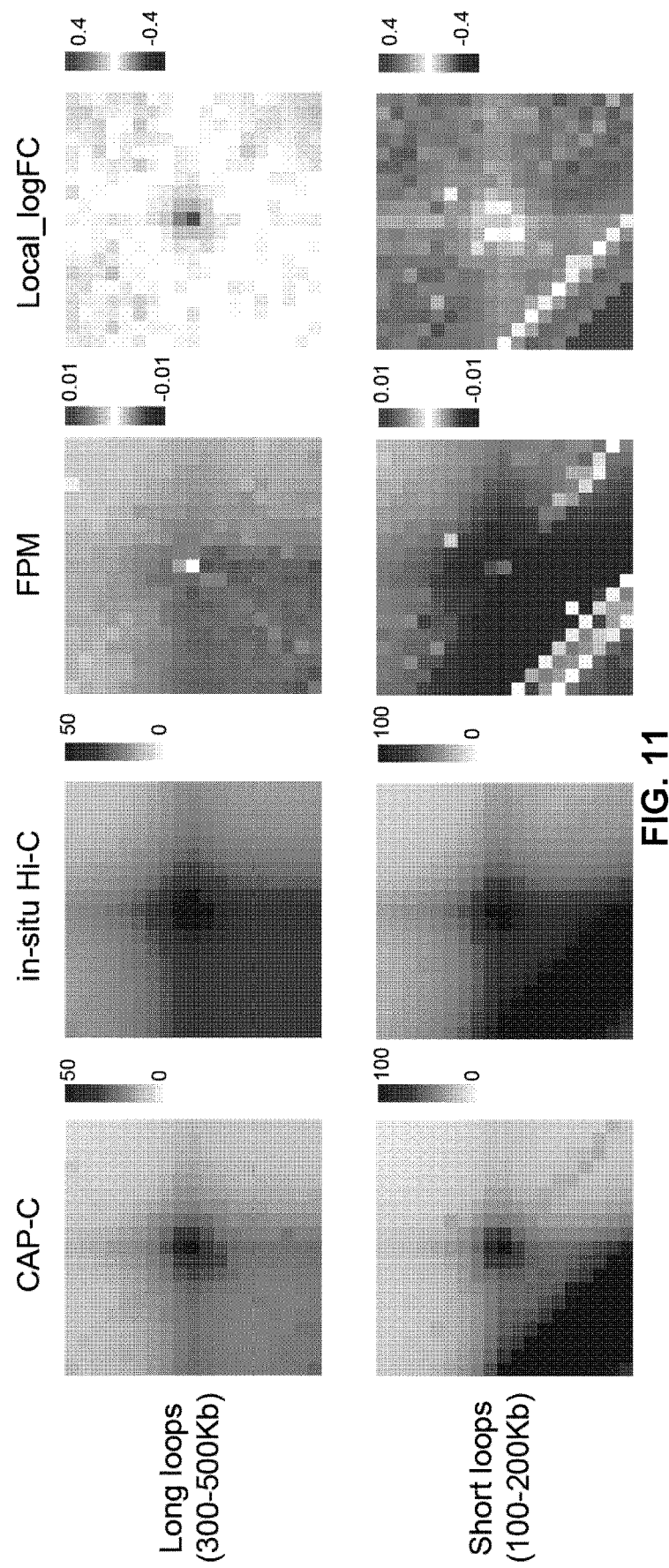

FIG. 11. CAP-C shows a higher signal to noise ratio around loop anchors over in-situ Hi-C. Meta-analysis of concordant peak calls was performed to explain why CAP-C shows a 3-fold increase in peak calls as well as an enrichment of peaks spanning short distances. When normalized for sequencing depth (FPM), the mean delta signal between the focal center of CAP-C and in-situ Hi-C maps is close to zero (column 3). However, normalizing the FPM value by the mean value of the local region, and comparing this local-normalized signal between maps (log FC) suggest a higher signal to background ratio around loop anchors in CAP-C than in-situ Hi-C (column 4). Peaks closer to the diagonal (bottom row), which are harder to call, also show higher enrichment when classified by the span of their genomic distance.

Figure 12:
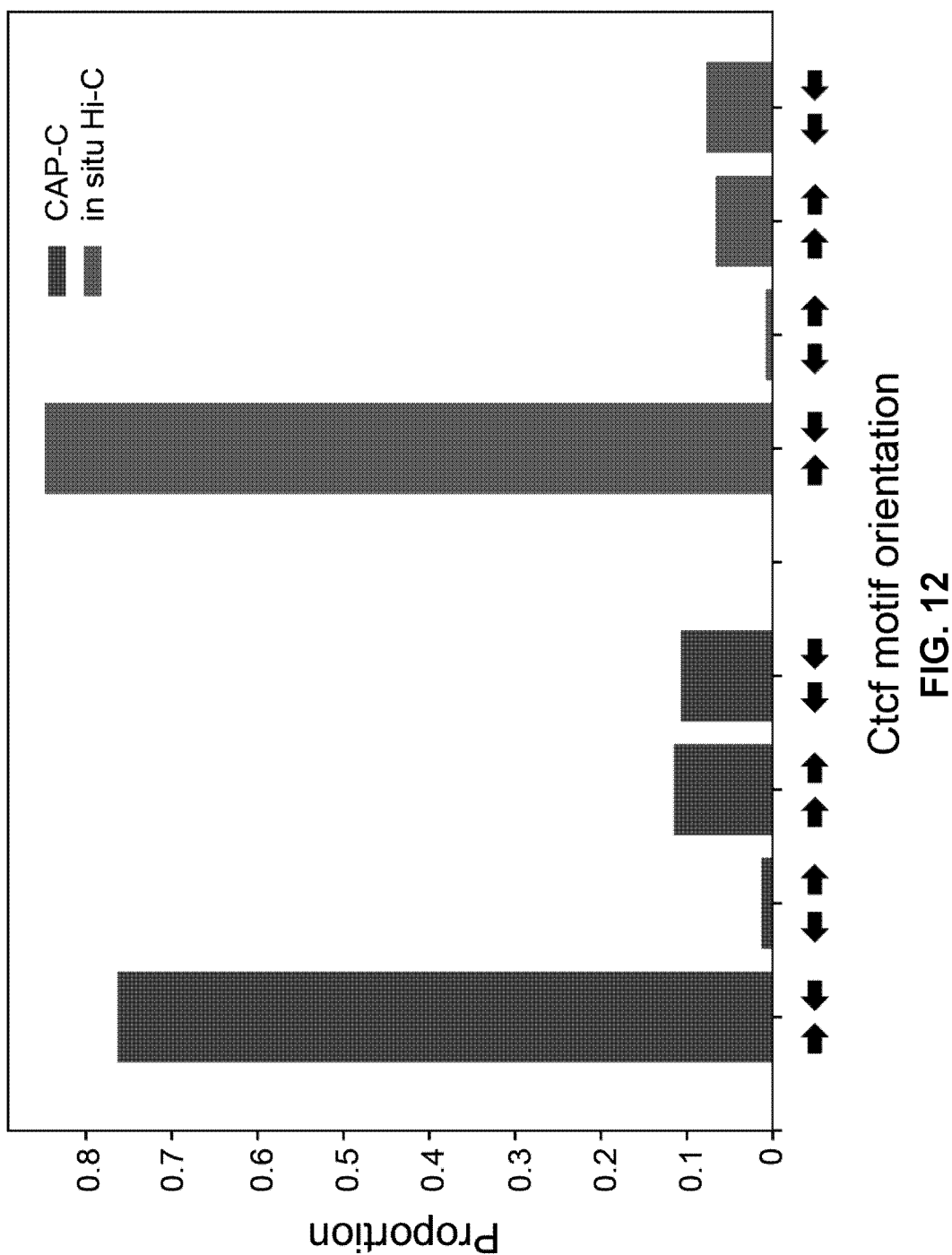
Figure 13A:
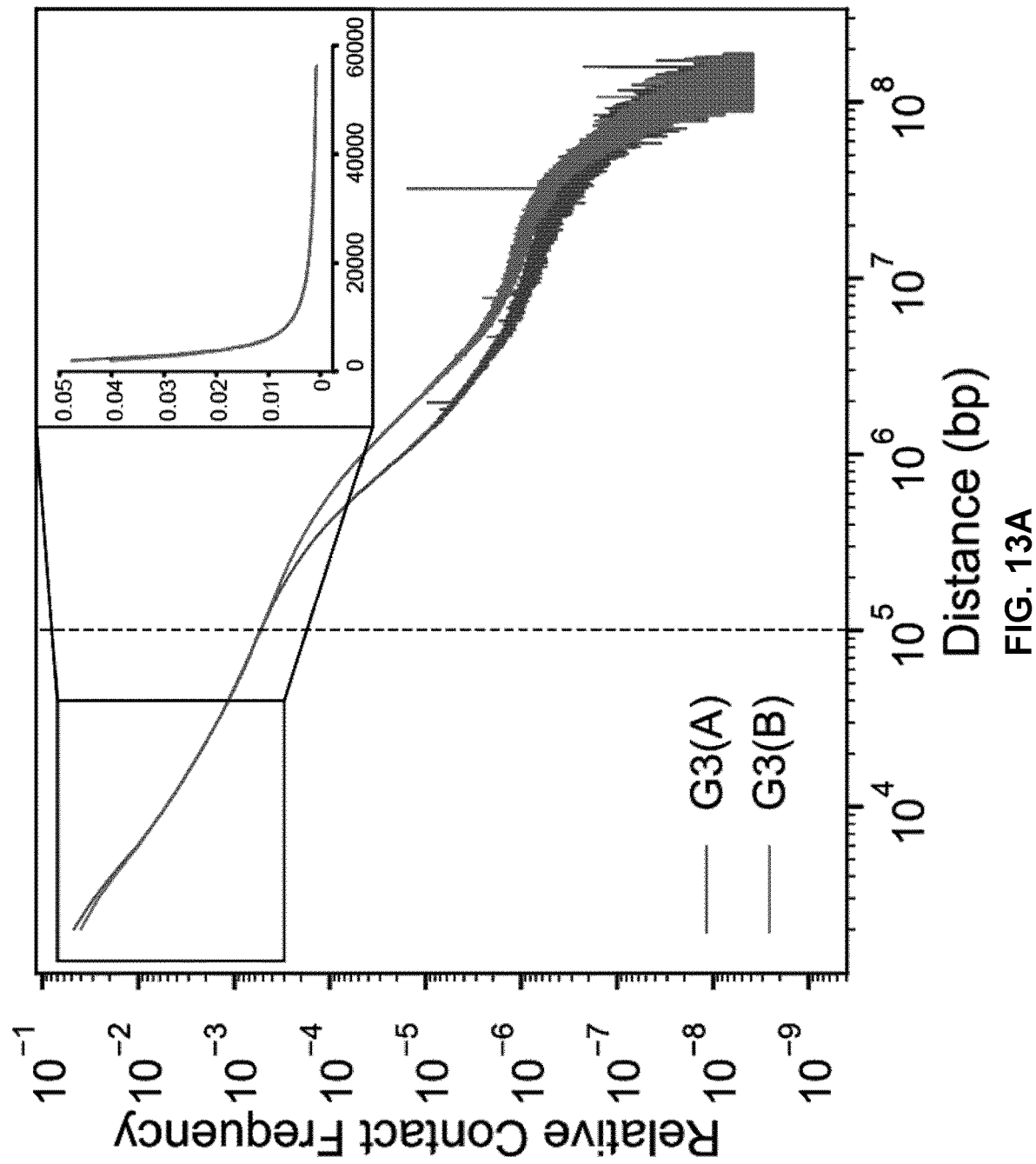
Figure 13B:
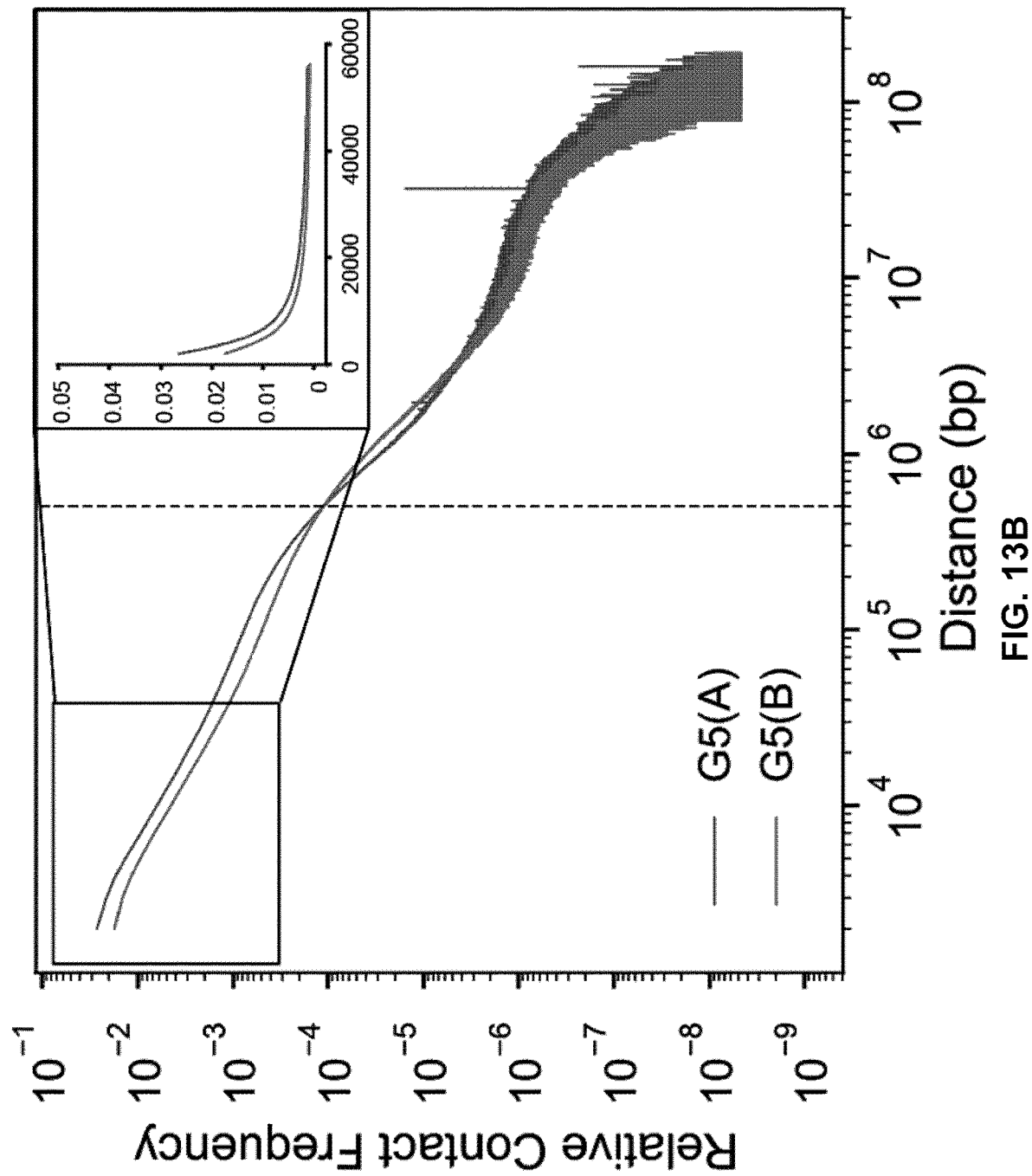
Figure 13C:
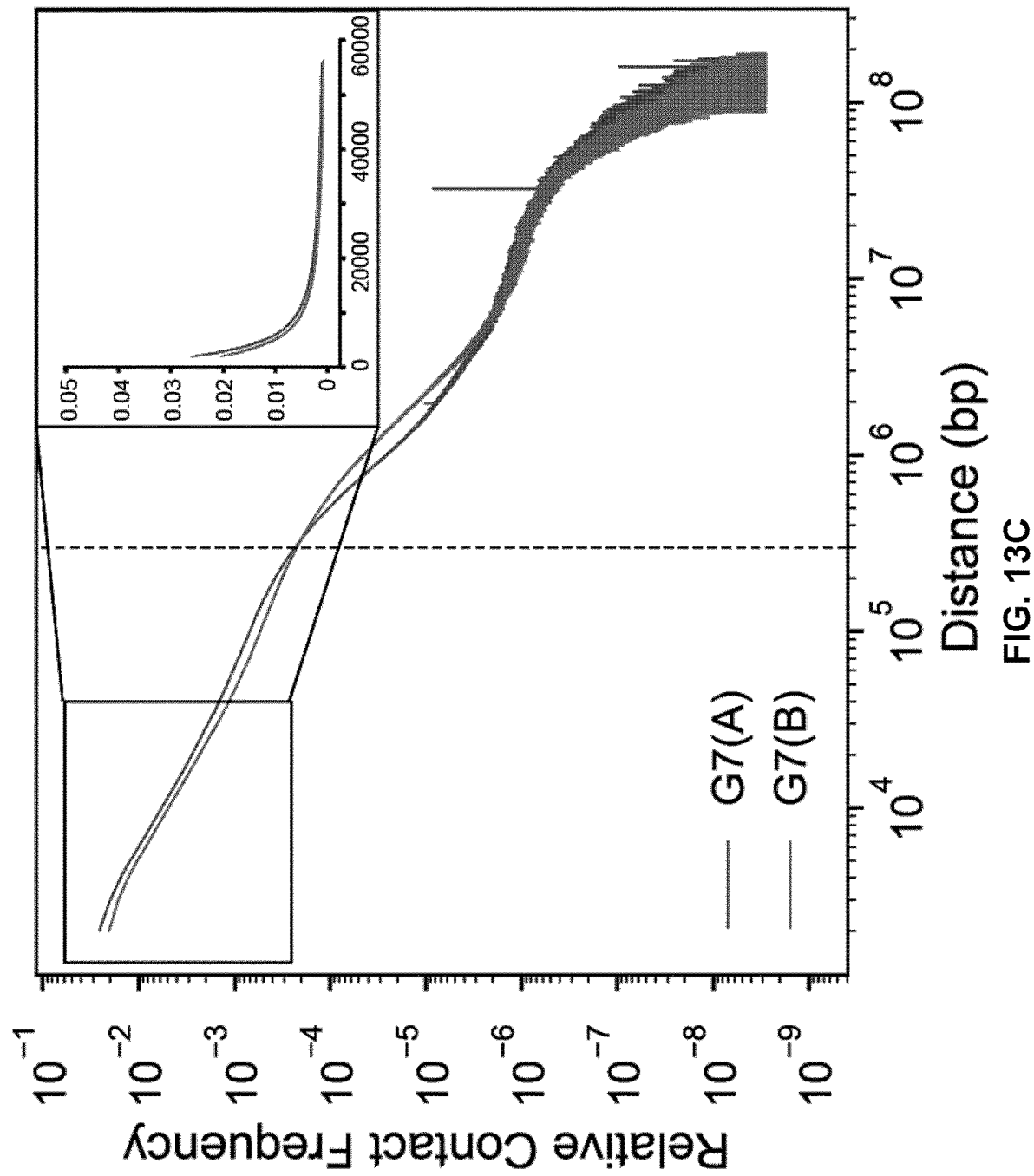
Figure 13D:
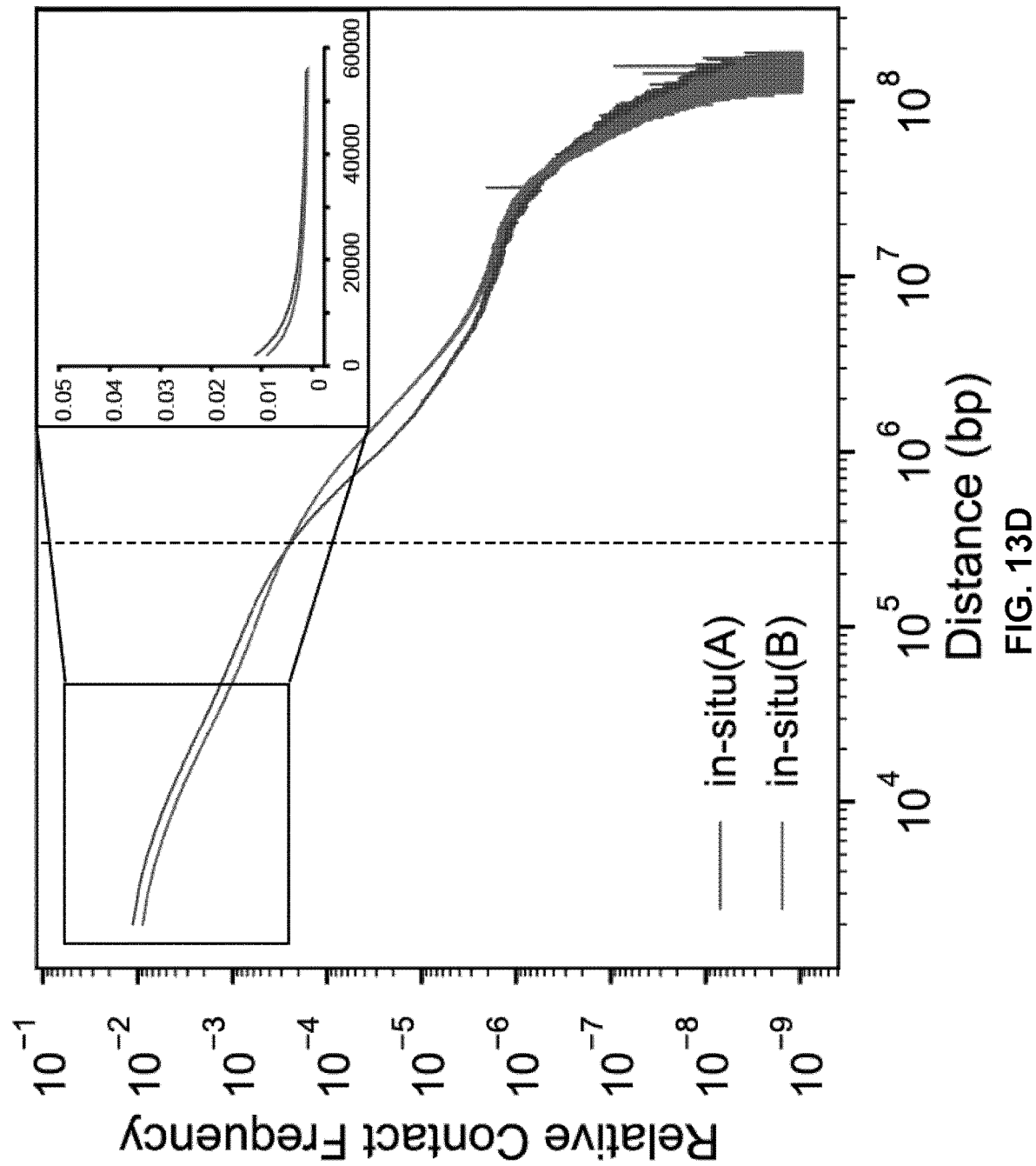

FIG. 12. Ctcf motif orientation analysis of loops in CAP-C and in-situ Hi-C. 76.3% and 84.8% of unique Ctcf motifs for CAP-C and in-situ Hi-C were in the convergent orientation, suggesting either a slightly higher false positive rate of CAP-C or that certain peaks, i.e. CTCF-cohesin independent ones, may not be conforming to the rules of the loop-extrusion model.

Figure 2A:
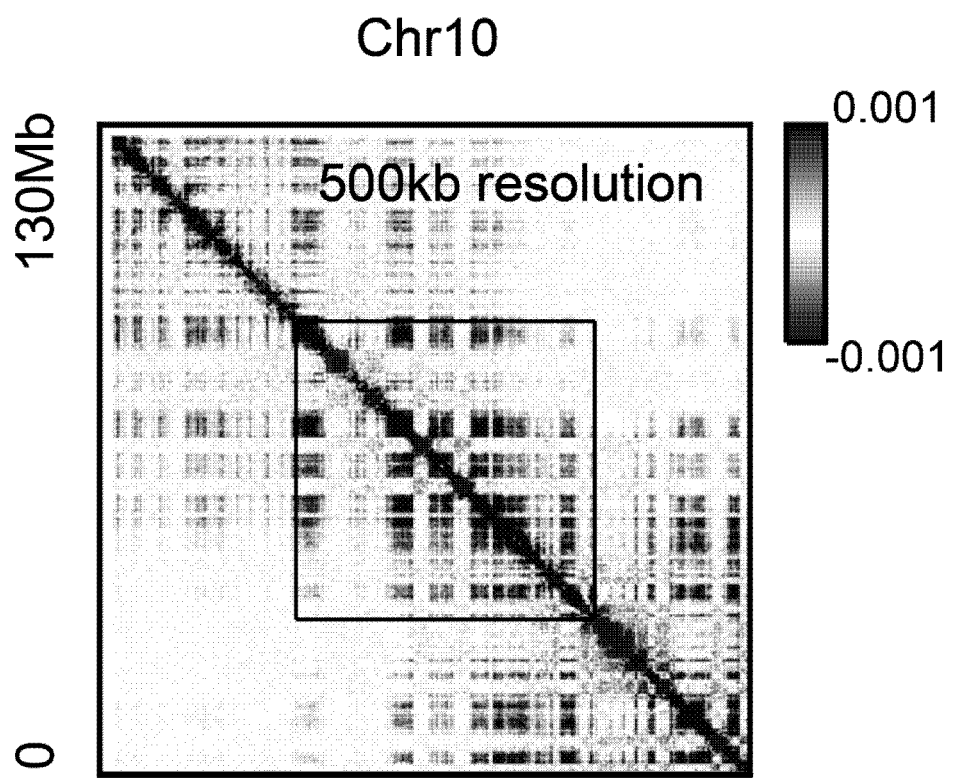
FIGS. 2A-E. Chromatin contacts detected by G5 and G7 dendrimers are enriched for compartment A whereas those detected by G3 dendrimers are enriched for compartment B. (A to D) The eigenvector with the highest eigenvalue (or a rescaled version commonly referred to as the proportion of explained variance ranges between 90 to 95%) calculated for a 3 by $N*(N+1)/2$ matrix (where N is the number of loci across a specified resolution) using principal component analysis yields a CAP-C map that shows a bifurcated separation that is similar to compartment intervals. Principal component loadings (bottom left arrow bars) suggest that G5 and G7 dendrimers contribute most to an open configuration while G3 dendrimer to a closed configuration. (A to C) In low-resolution maps, the inventors observed checkerboard patterns, usually associated with compartments, which are also associated with the enrichment of specific dendrimers. (D) A close-up (5 kb res) examination of the CAP-C map reveal a fine level of compartment detail. mESC TADs annotated in the lower-left triangle and Arrowhead contact domains annotated on the upper-right triangle reveals that the relationship between compartments intervals and domains (or domain boundaries) is complex. (E) A G3 versus G5 delta map shows the one-to-one relationship with eigenvector compartments. CAP-C eigenvectors computed using the row-sums instead of pixels in (A to D) gives increasing levels of high-resolution eigenvectors showing compartment intervals which are tens of kilobases in length, and missed in the low-resolution compartments calculated using the Pearson matrix. CAP-C eigenvectors were validated by matching it with the in-situ Hi-C O/E 25 Kb resolution map to show the co-localization of compartments.
Figure 2B:
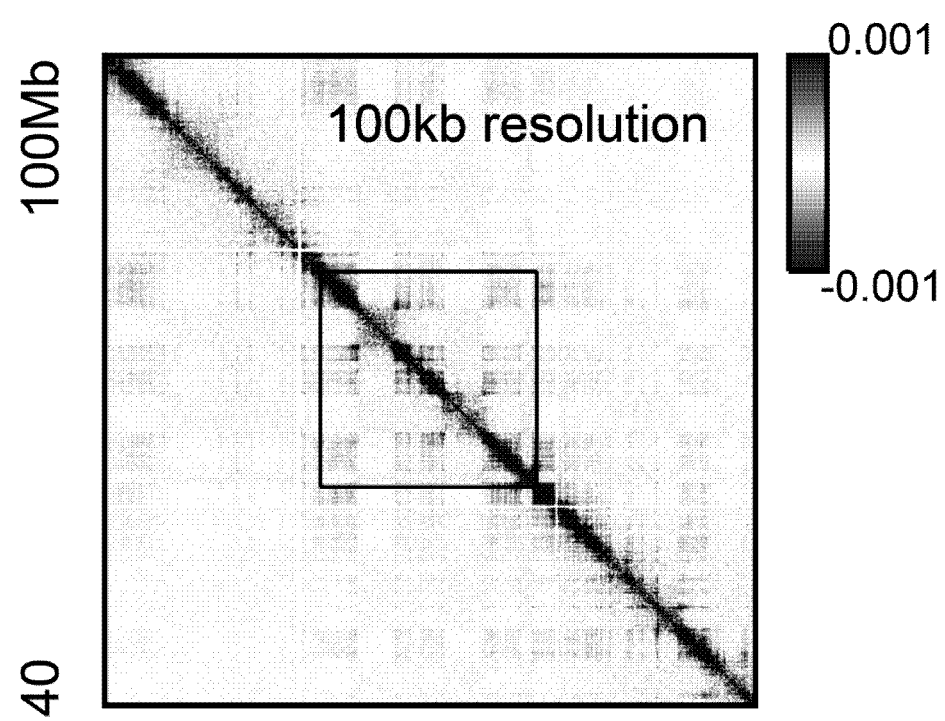
Figure 2C:
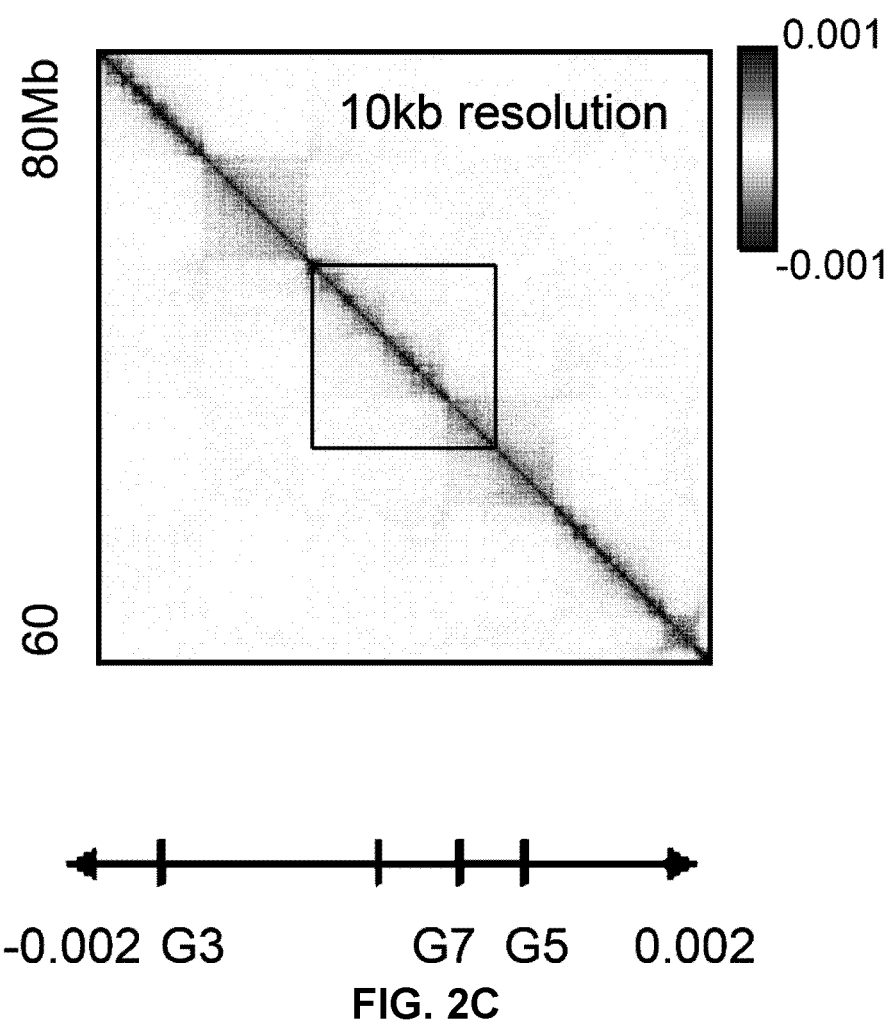

FIGS. 13A-D. Comparison of contact distributions in different compartments. Relative contact frequency of compartment A and B vs distance was plotted for G3; G5; G7 and in-situ Hi-C. As expected in FIG. 2B, there was a stronger enrichment of G3 contacts in compartment B after 100 Kb in distance, and a strong enrichment of G5 and G7 contacts in compartment A below 300 Kb in distance. This suggests that large regions of compartment B are in closer contact (G3) than compartment A while smaller regions in compartment A have a greater physical distance (more open) than compartment B.

Figure 14A:
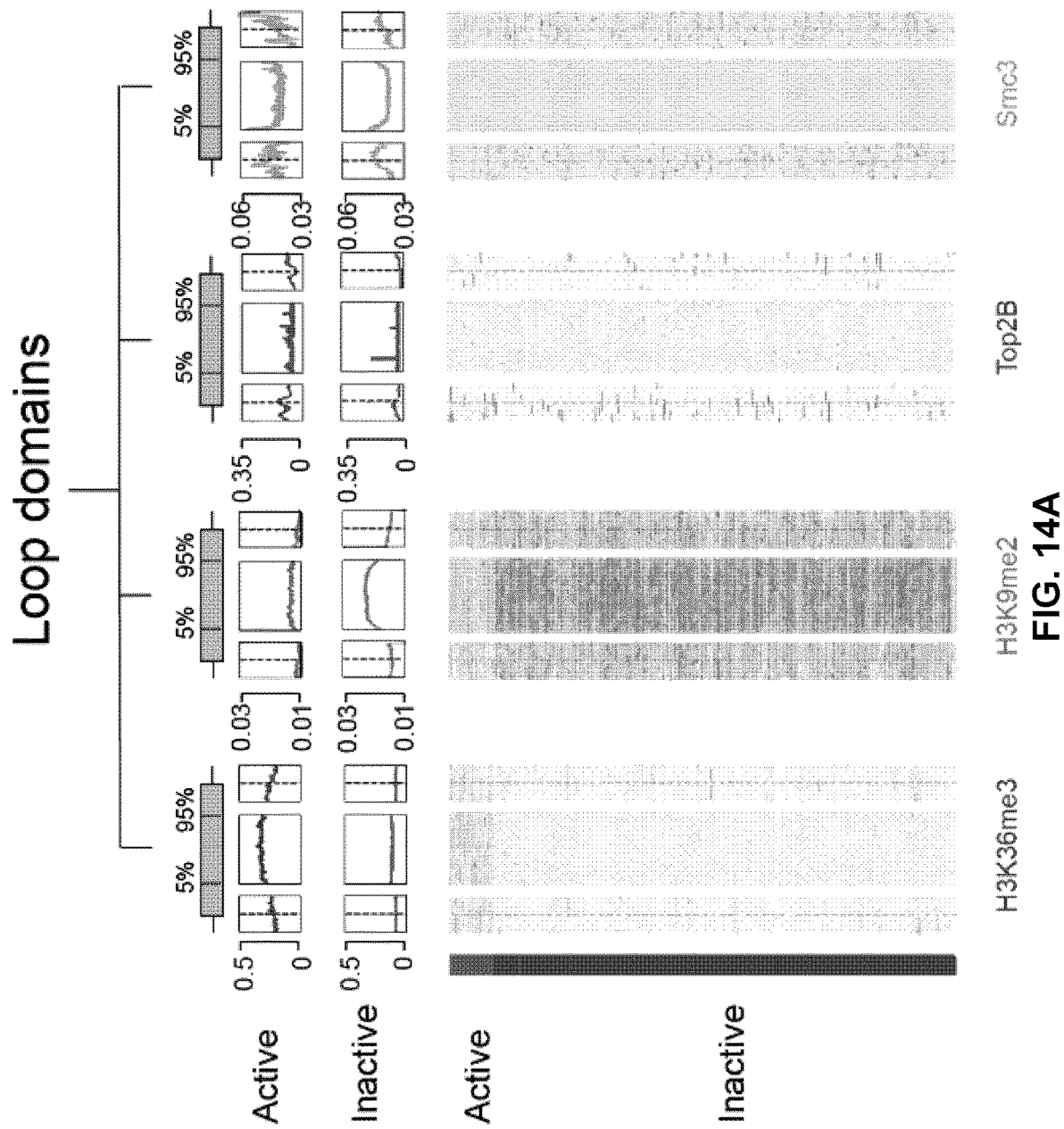
Figure 14B:
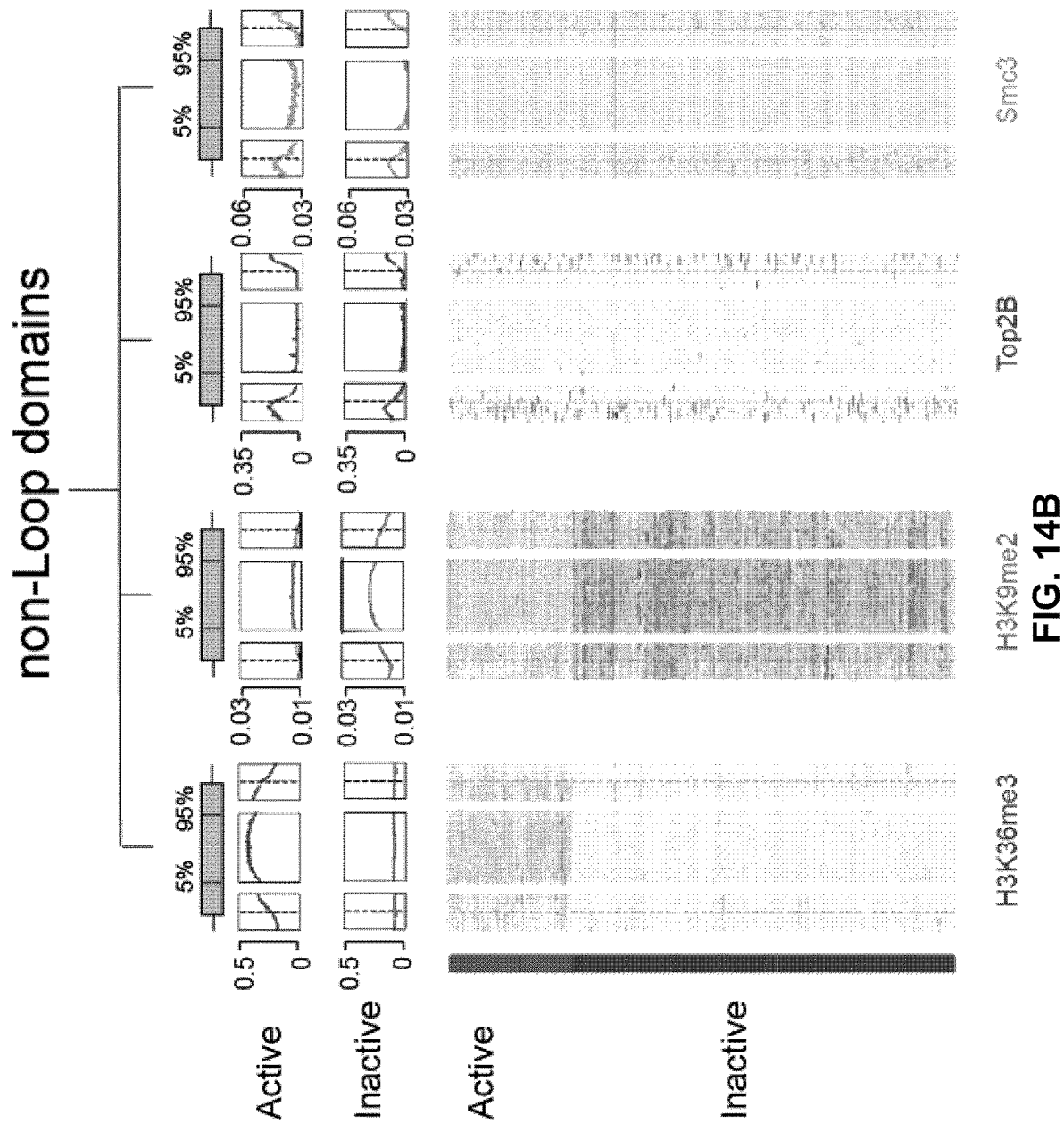

FIGS. 14A-B. Extended meta domain analysis. Meta-analysis of Top2b and Smc3 (cohesin) binding around boundaries (+/−2 Kb) of loop and non-loop domains suggest that boundaries of loop domains are enriched in Smc3 binding while boundaries of non-loop domains are enriched in Top2b binding.

Figure 15:
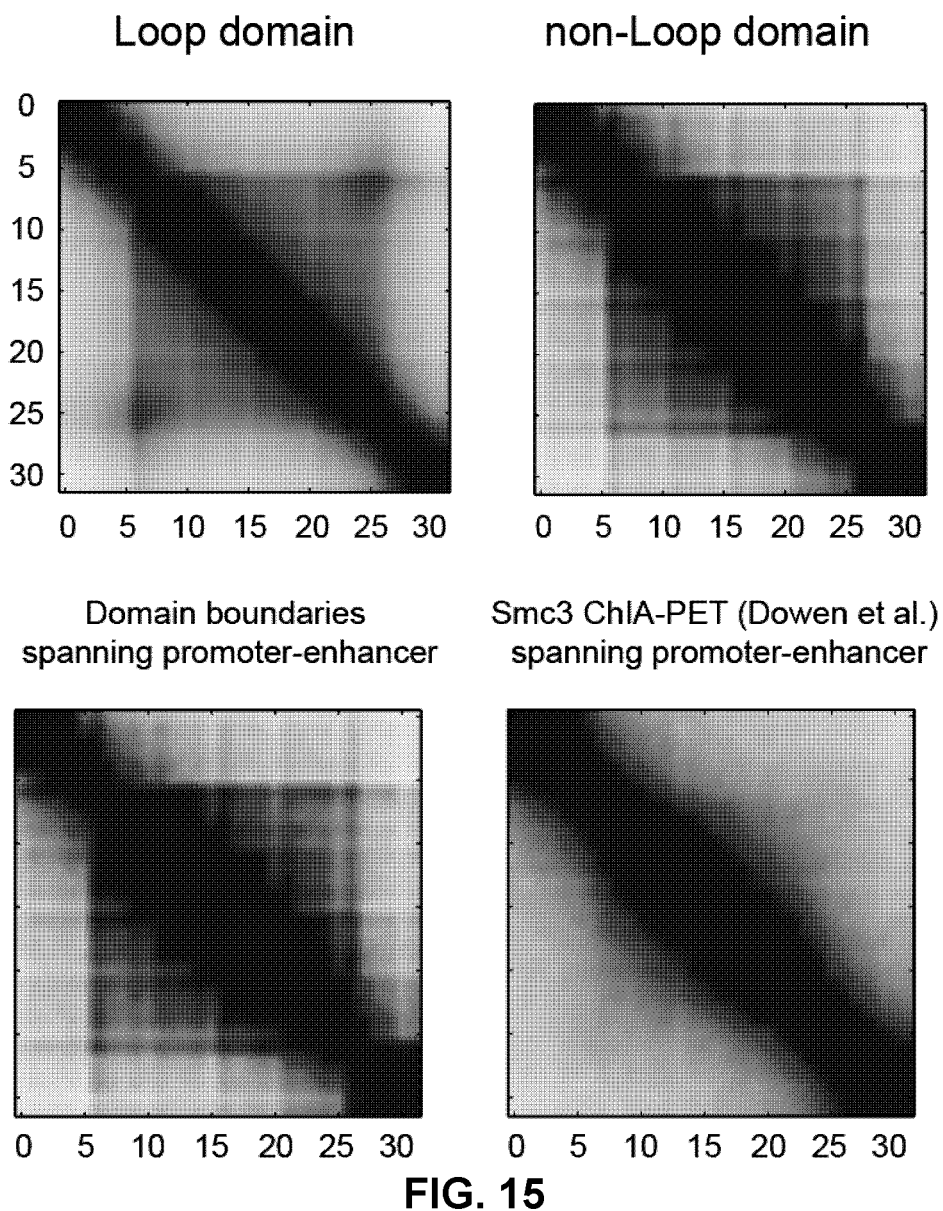

FIG. 15. Boundaries of domains spanning promoter and enhancers states do not show loops. Mean maps of domains with different characteristics were plotted. Boundaries of domaisn were extended by 30% in both direction, and re-scaled into+/−15 bins from the domain center. Here, loops at the corners of domains were a characteristic feature of loop-domains. Visualizing domains whose boundaries were marked by promoter and enhancer ChromHMM states suggest that these interactions do not show loops commonly characterized in Hi-C maps. Overlapping ChIA-PET Smc3 (8) interactions than span promoter and enhancer states on CAP-C maps also showed no such loops. This suggest that loops are probably extremely strong CTCF-cohesin binding.

Figure 16:
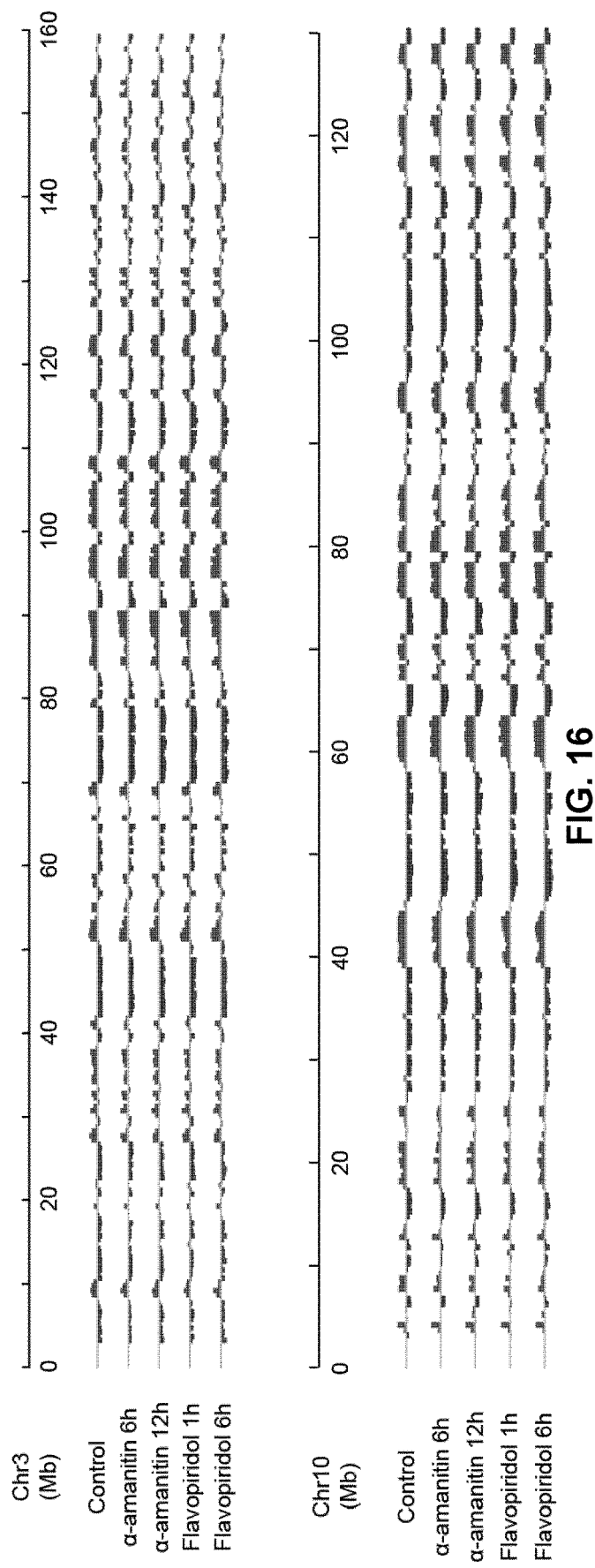

FIG. 16. Compartments remain unchanged upon transcription inhibition. Two examples of eigenvectors across full-length chromosomes, chr3: 0-160 Mb (top panel) and chr10: 0-130 Mb (bottom panel), before and after transcription inhibition. Compartment intervals remain unchanged for all inhibitor-treated samples. Compartment A intervals are colored green while compartment B intervals are colored red.

Figure 17A:
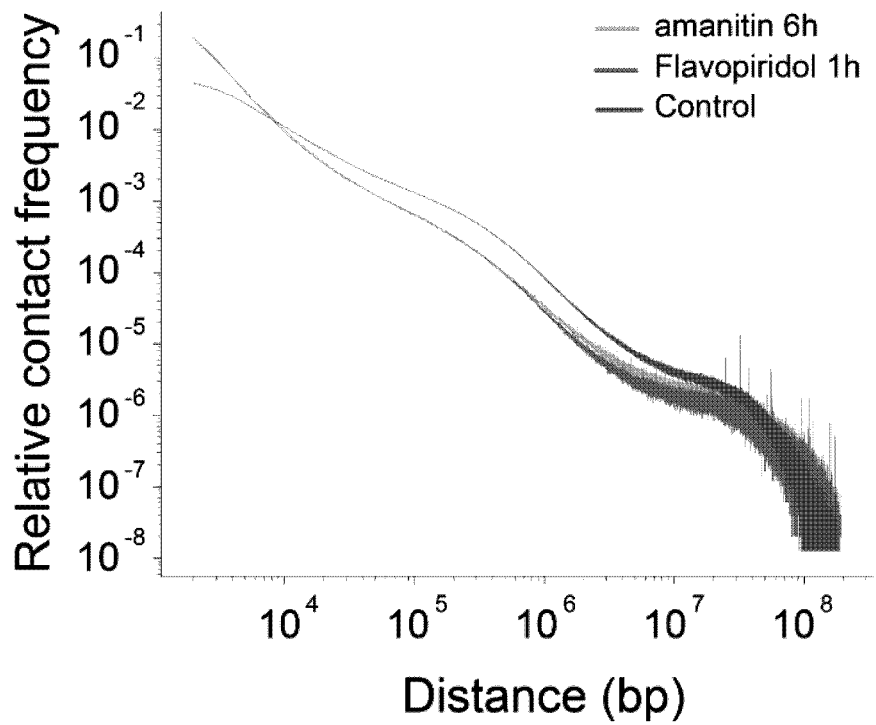
Figure 17B:
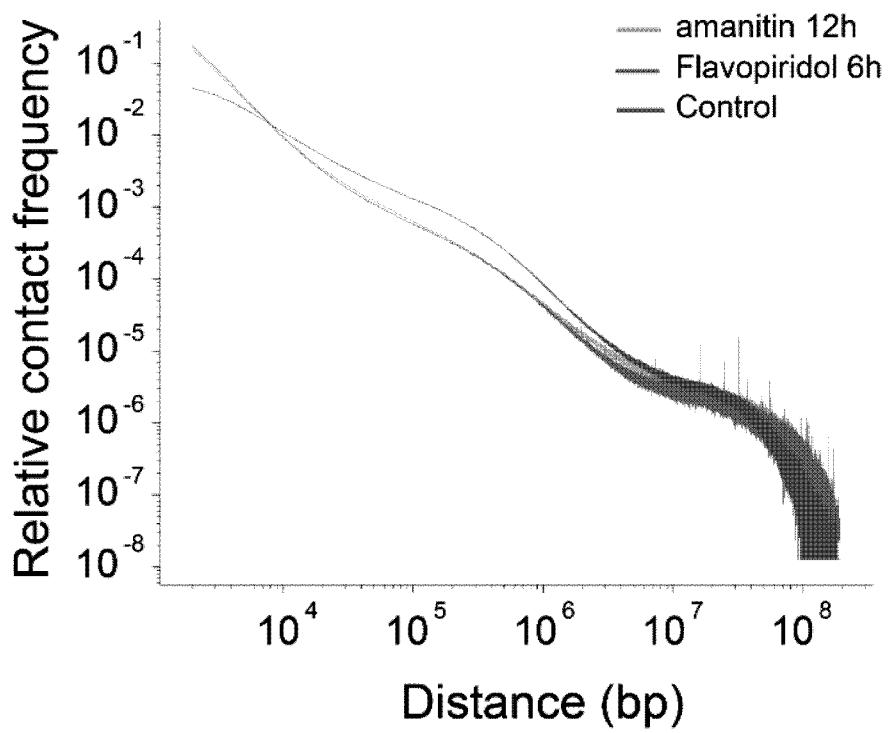

FIGS. 17A-B. Loss of long-range chromatin contacts are observed through transcription inactivation. Relative contact frequency vs distance curve generated from control and transcription inhibitor-treated samples reveal that a large portion of long-range chromatin contacts (over 10 Kb) are lost upon transcription inhibition. Flavopiridol showed a slightly strong depletion of contacts over 1 Mb.

Figure 18A:
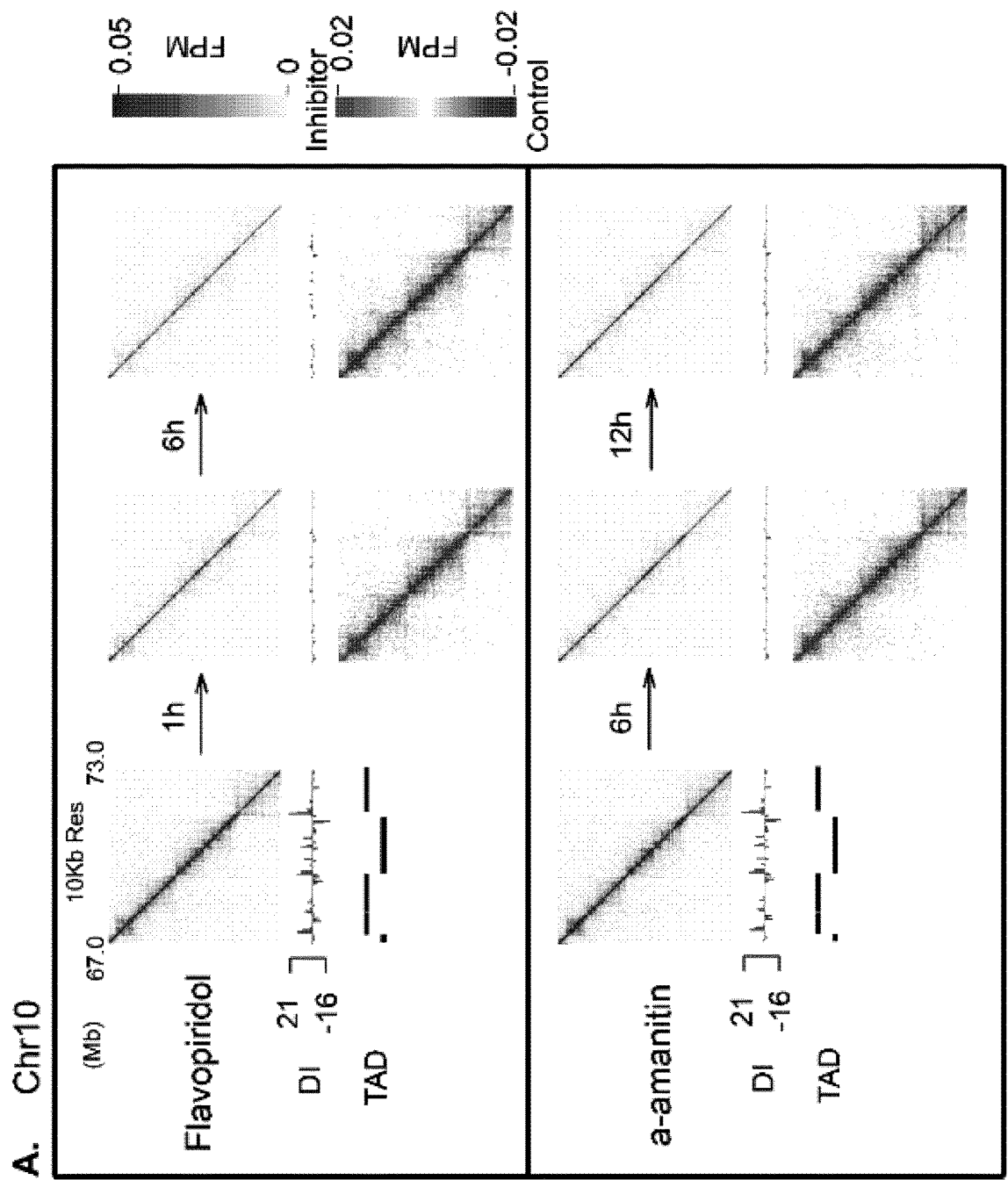
Figure 18B:
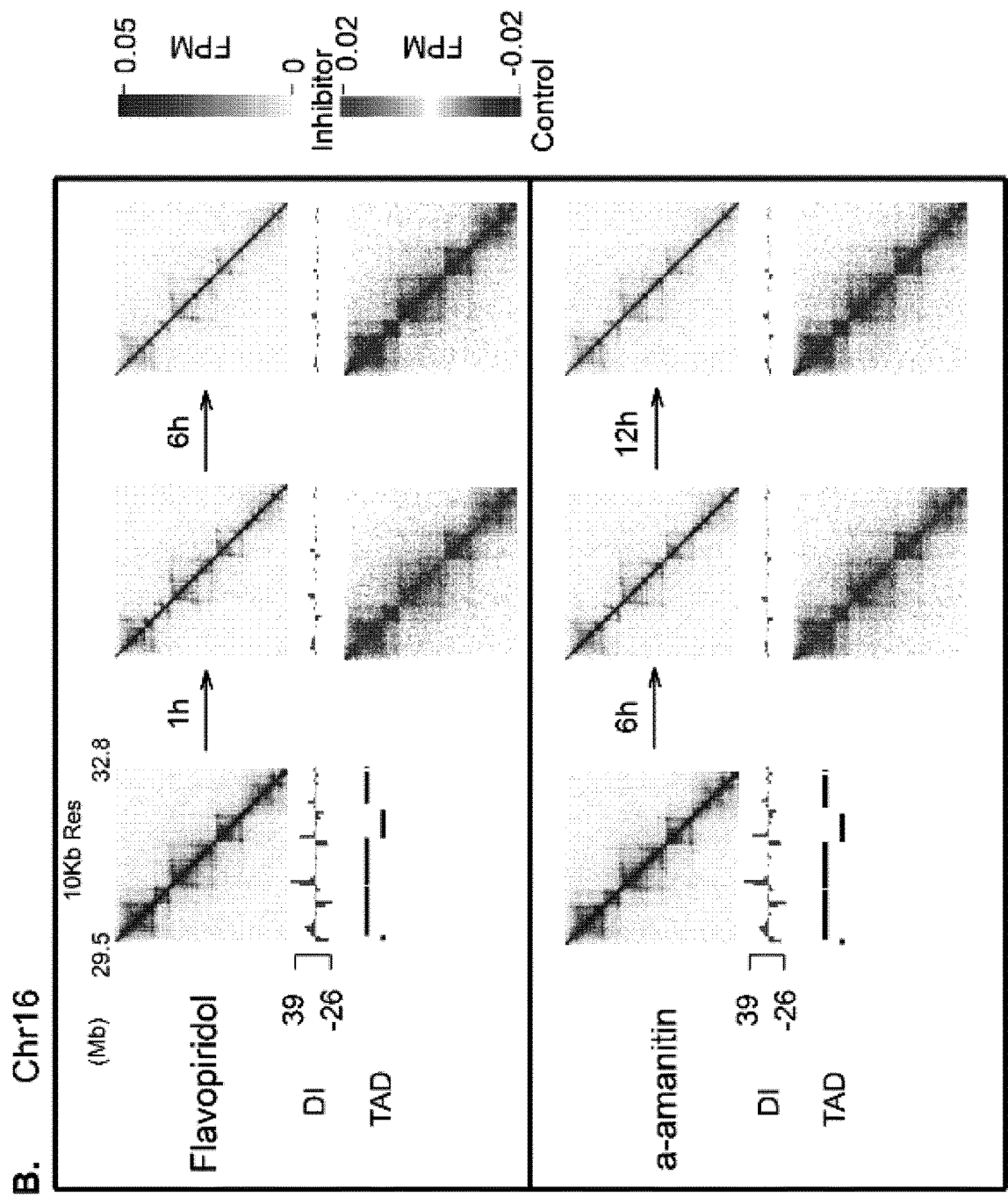

FIGS. 18A-B. Transcription inhibition causes widespread loss of domains. 10 Kb resolution contact maps shown here for chr10: 67.0-73.0 Mb (left panel) and chr16: 29.5-32.8 Mb (right panel). Reduction in directionality indices (DI) between inhibitor-treated vs control indicate the weakening of boundaries. Similarly, delta maps between inhibitor-treated vs control maps indicate the loss of intra-domain interactions.

Figure 19C:
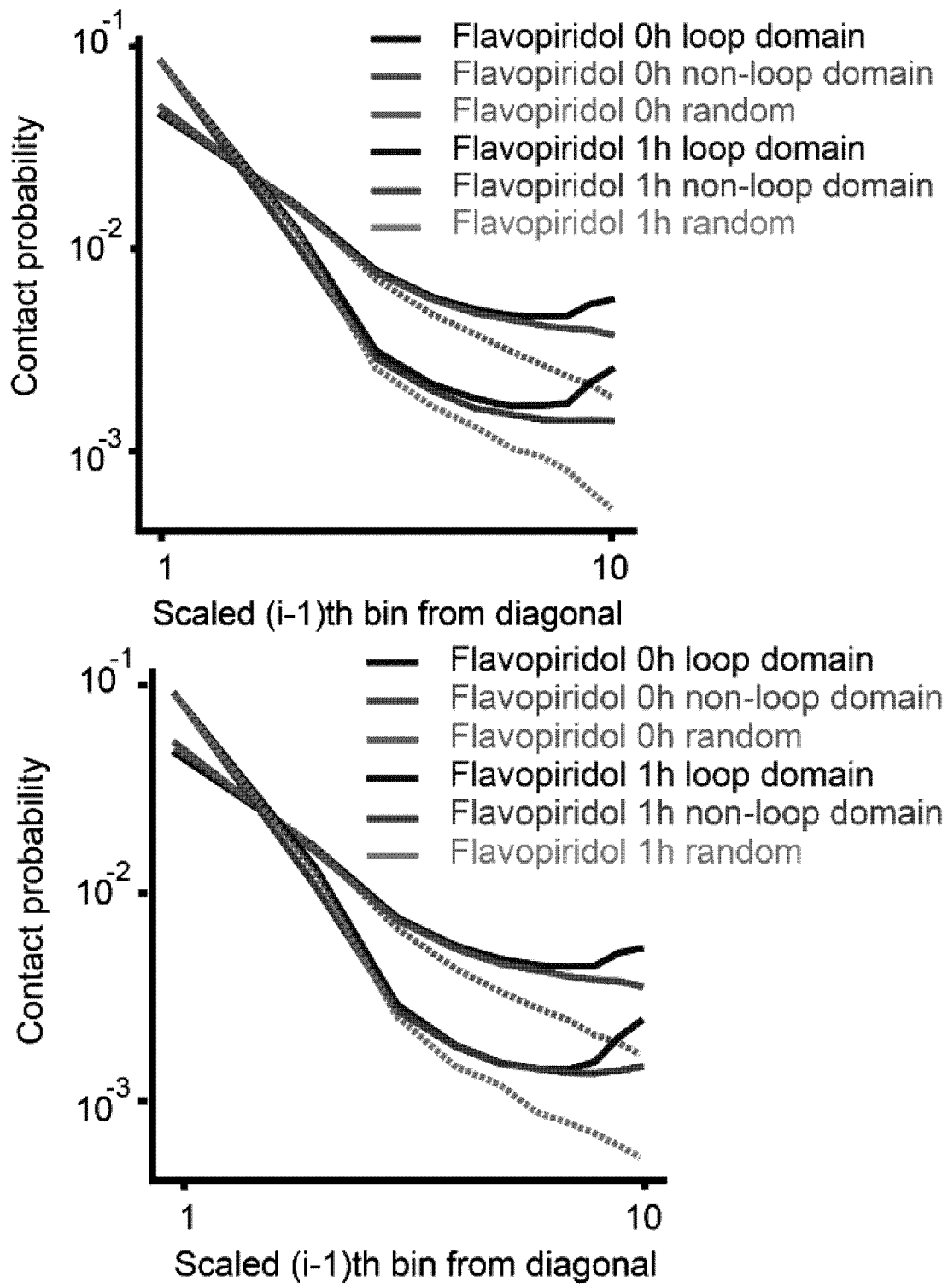

FIGS. 19A-C. Loops are attenuated but preserved in flavopiridol-treated samples. (A) APA analysis was performed on low-resolution maps using loops called in the high-resolution CAP-C map. Aggregated signals showed the presence of loops after flavopiridol treatment. (B) Similar meta-analyses of loops were performed (See FIG. 5) for flavopiridol-treated samples. (C) Mean maps were quantified as contact probability vs scaled distance and showed that loops are preserved but attenuated (bin 8 to 10).

Figure 20A:
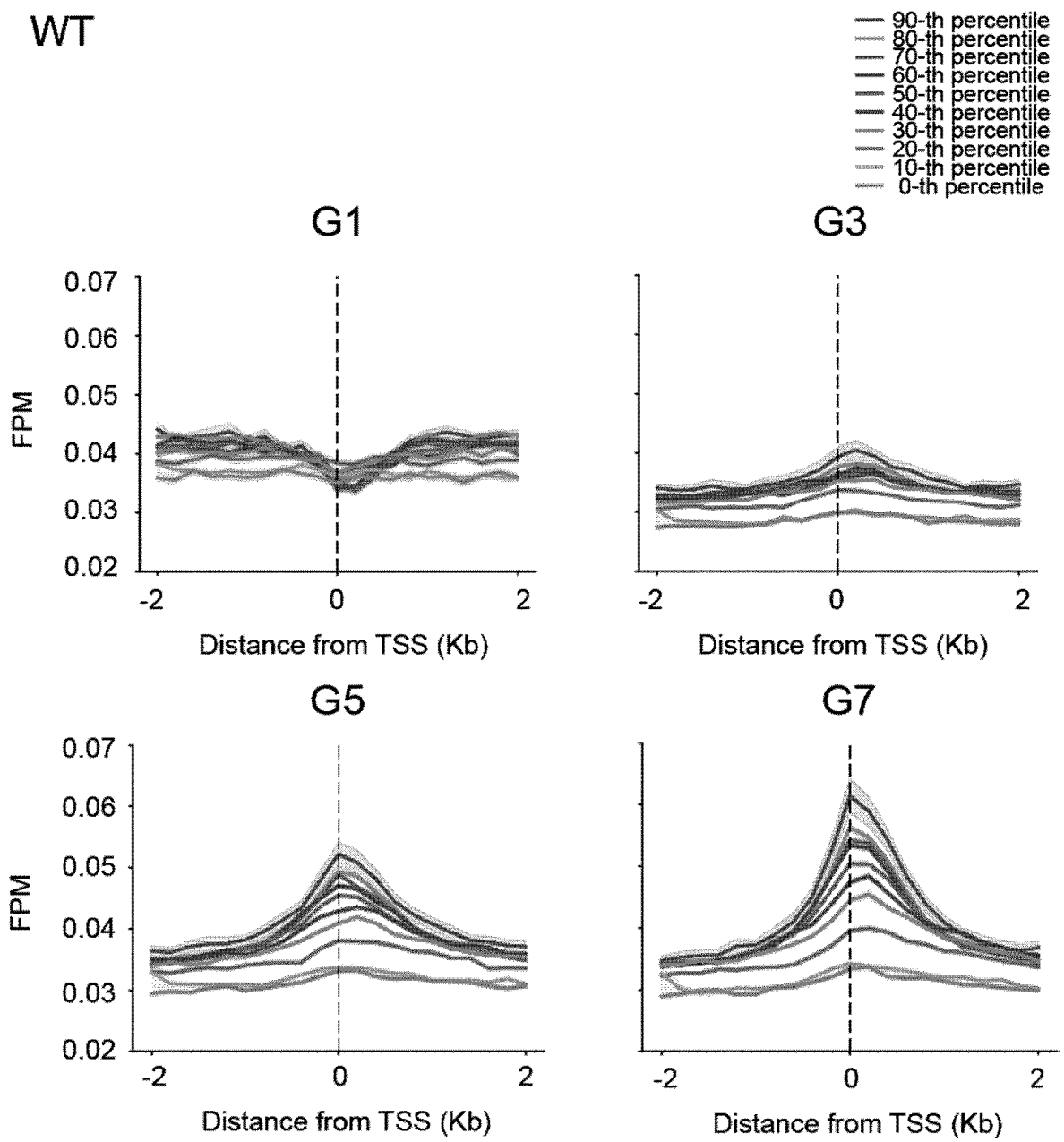
Figure 20B:
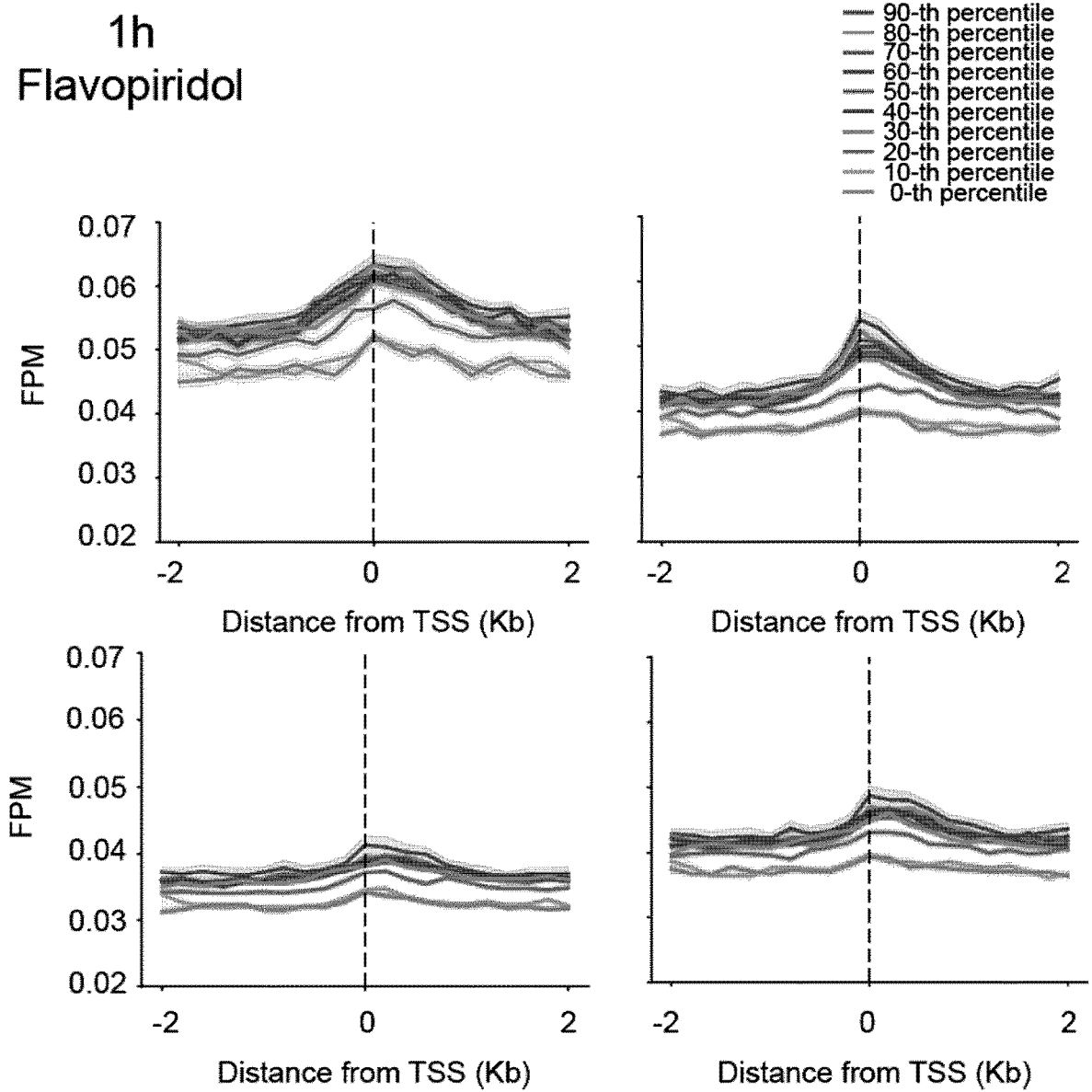

FIGS. 20A-B. Probing the openness of transcription starting sites (TSS) by biotinylated psoralen functionalized dendrimers. TSS are classified into 10 groups based on their transcription state. Each line represents the mean of the percentile of nascent gene expression at its TSS using Pro-seq signal. ($90^{th}$ percentile shows the highest nascent gene expression while $0^{th}$ exhibits the lowest) Normalized sequencing counts (FPM) are plotted+/−2 Kb around TSS for each percentile. (First row: experiment was performed on wild type cells; Second row: experiment was performed on cells treated with flavopiridol for 1 h).

Figure 21:
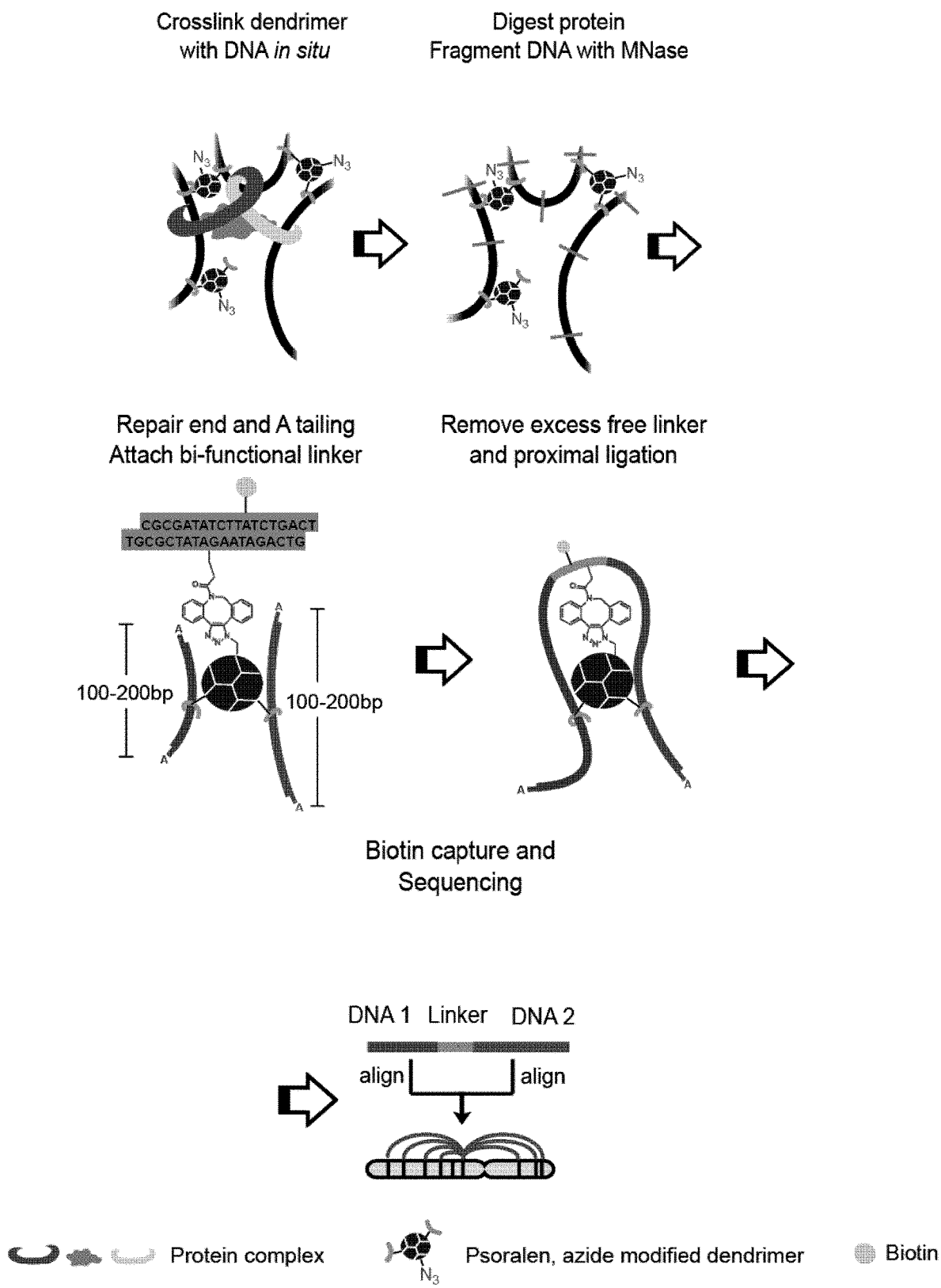

FIG. 21. General CAP-C scheme. Azide and psoralen-modified PAMAM dendrimers with fixed diameter (shown as balls) are diffused into nucleus of mouse embryonic stem cells (mESCs). DNA (black strings) in proximity are covalently crosslinked with dendrimers under 365 nm UV irradiation. Proteins are digested with protease and dendrimer-DNA complex are purified. The purified complexes are then subjected to MNase digestion and end polishing, bi-functional linkers (for example the linker can comprise annealed SEQ ID NO:33 and SEQ ID NO:34) bearing DBCO and biotin are attached to dendrimer-DNA complexes via "Click chemistry". Excess linkers are removed by size selection. Proximal DNA on the same dendrimer is ligated through bridge linker, followed by biotin capture and high throughput sequencing.

Figure 22:
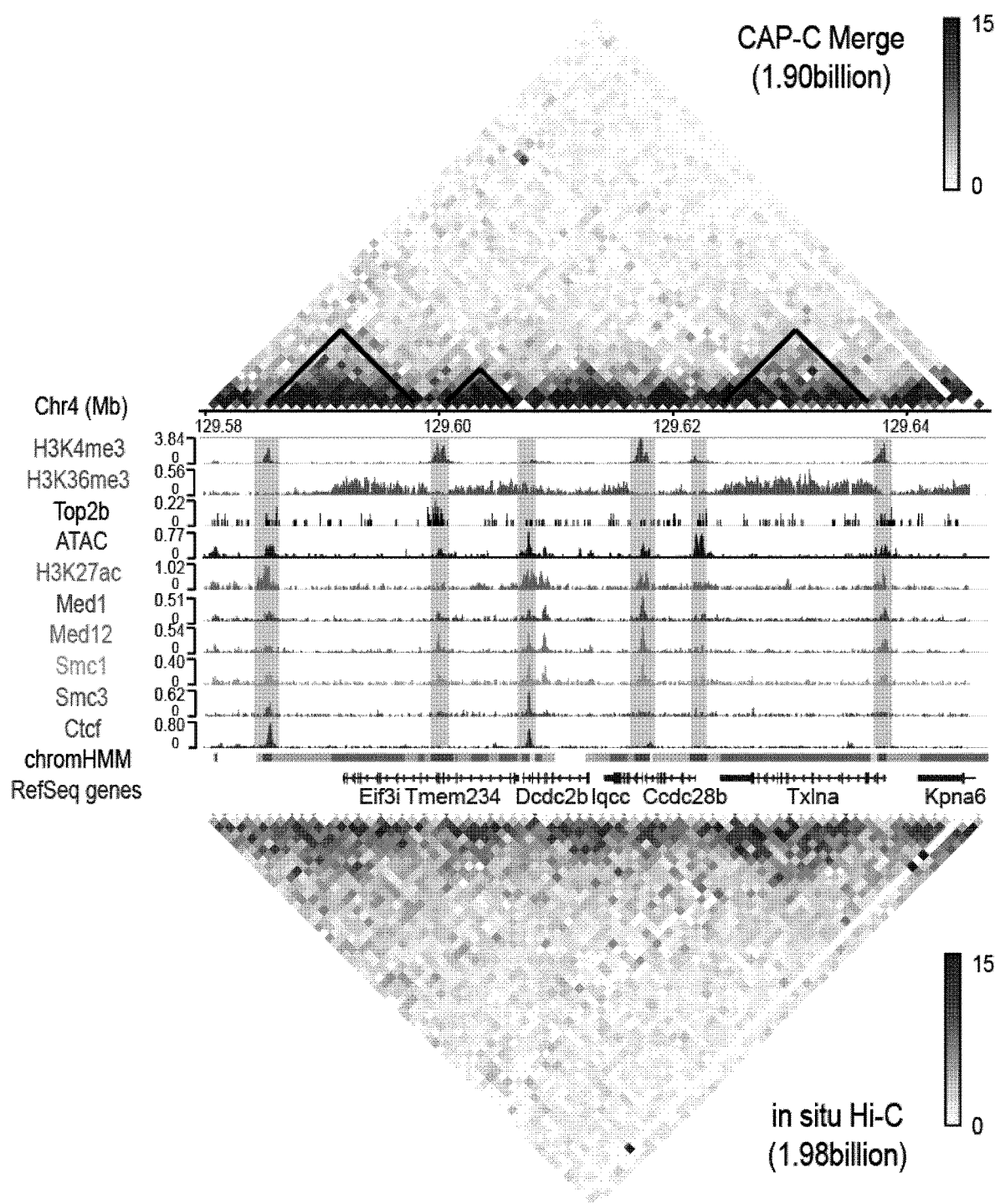

FIG. 22. CAP-C exhibit enhanced chromatin contact frequency at high resolution. 70 Kb-long regions of CAP-C (top) and in-situ Hi-C (bottom) 1 kb resolution contact matrixes are shown corresponding to Chr4: 129.58-129.65 Mb. Histone modification and ChTP profiles are shown in the middle. Arrowhead detected 3 domains (Black triangle) in CAP-C enveloping Eif3i, Tmem234 and Txlna, respectively. Domain boundaries are highly enriched for active promoters, mediators and enhancers. No domains were detected for in-situ Hi-C at this resolution.

Figure 23A:
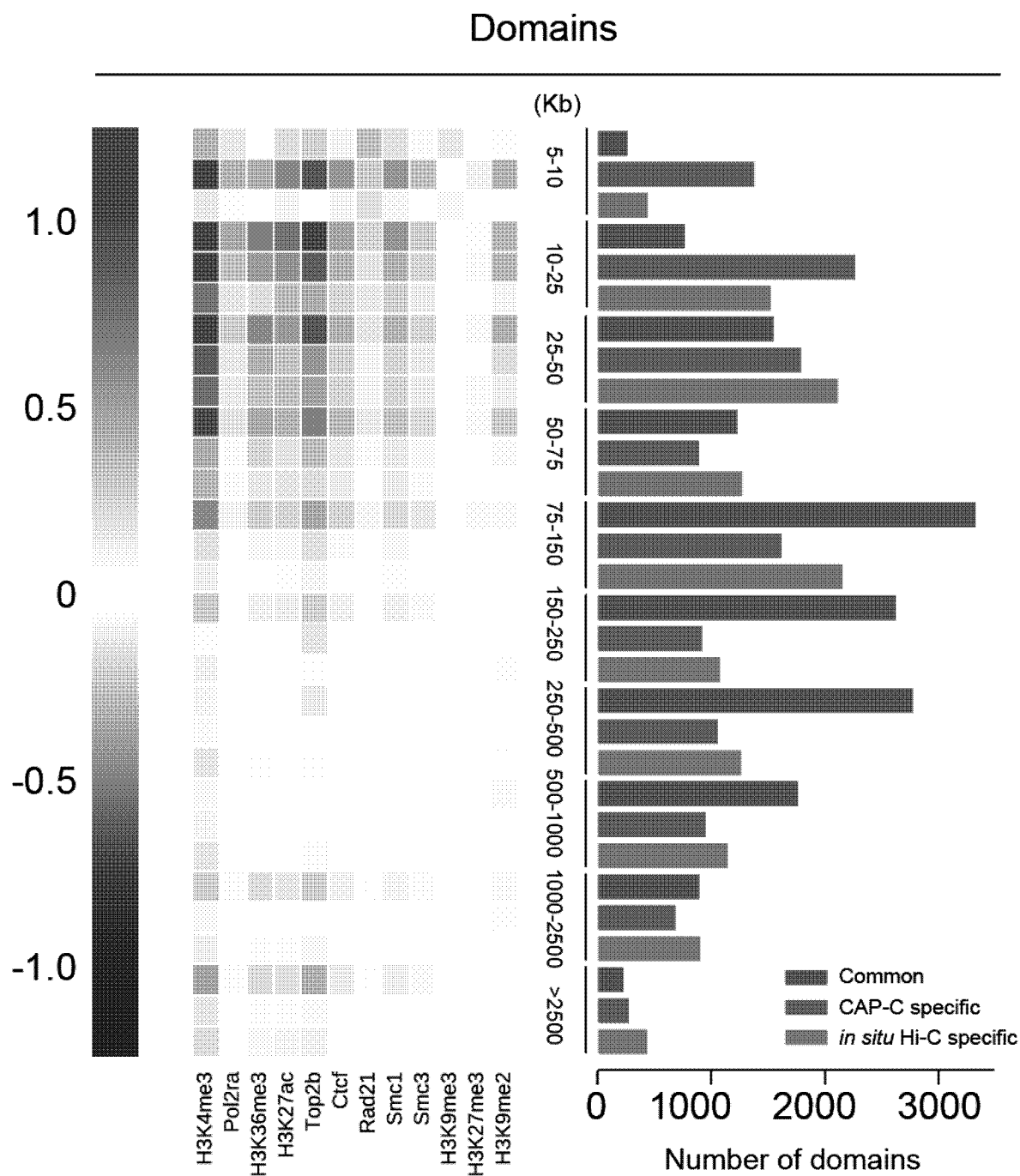
Figure 23B:
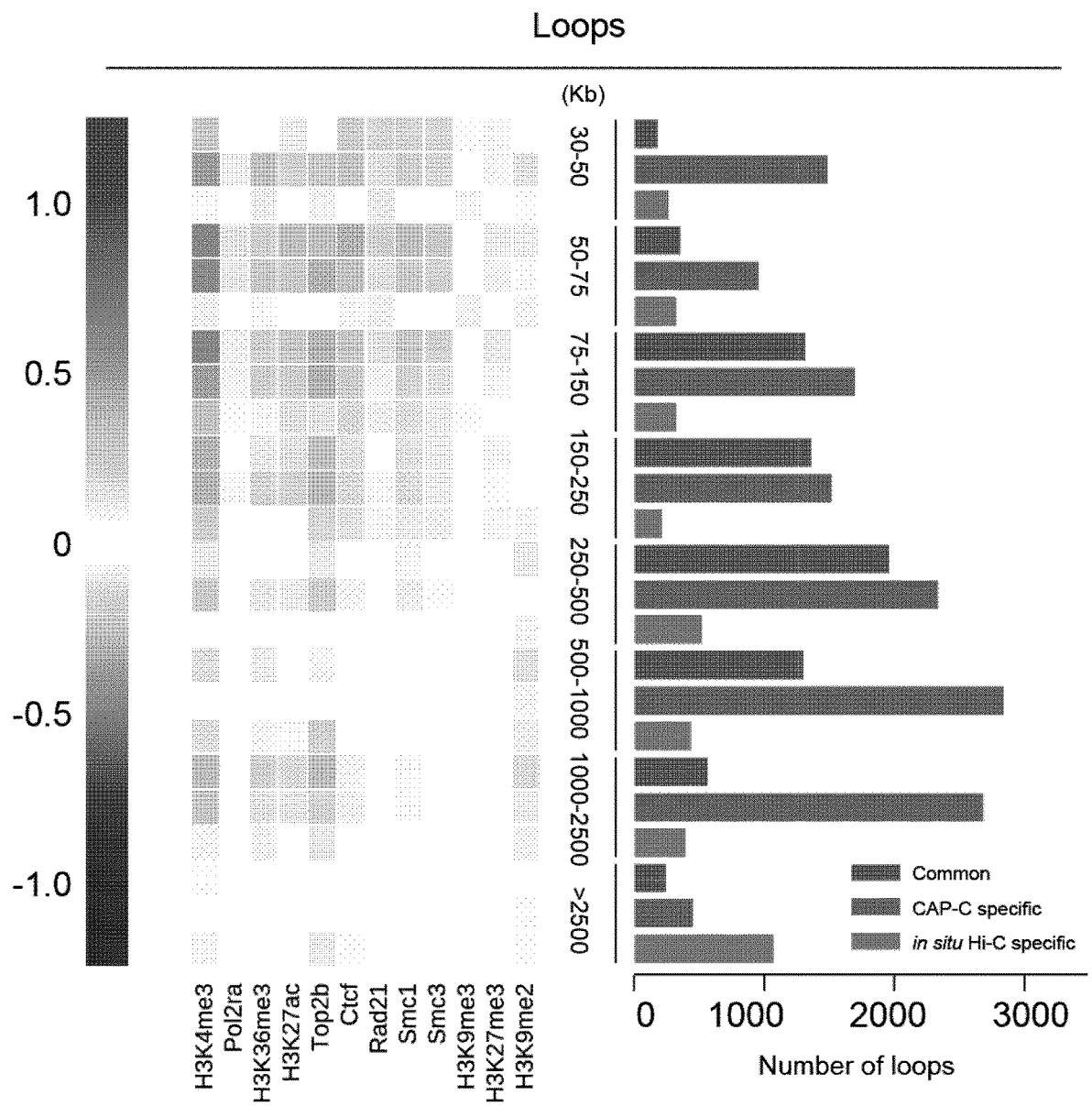

FIGS. 23A-B. CAP-C captures more functional and structural related loops and small domains. Domains are called by Arrowhead while loops are called by HiCCUPS using high resolution map with the same sequencing depth (CAP-C: 9.0 billion; in-situ Hi-C: 9.2 billion). Left: Domains are classified into 10 groups based on the size, CAP-C specific domains (shown as a bar) are 2-fold more than in-situ Hi-C domains (shown as a bar) at the length of 5-25 Kb. Overlap of domain boundaries with known proteins ChIP-Seq data indicates CAP-C specific domains correlates better with active histone marks, CTCF or cohesin. Right: CAP-C capture 2.5-fold more loops genome-wide. Overlap of loops with known proteins ChIP-Seq data indicates CAP-C specific loops (shown as a bar) correlates better with active histone marks, CTCF or cohesin compared to in-situ Hi-C specific loops (shown as a bar).

Figure 24:
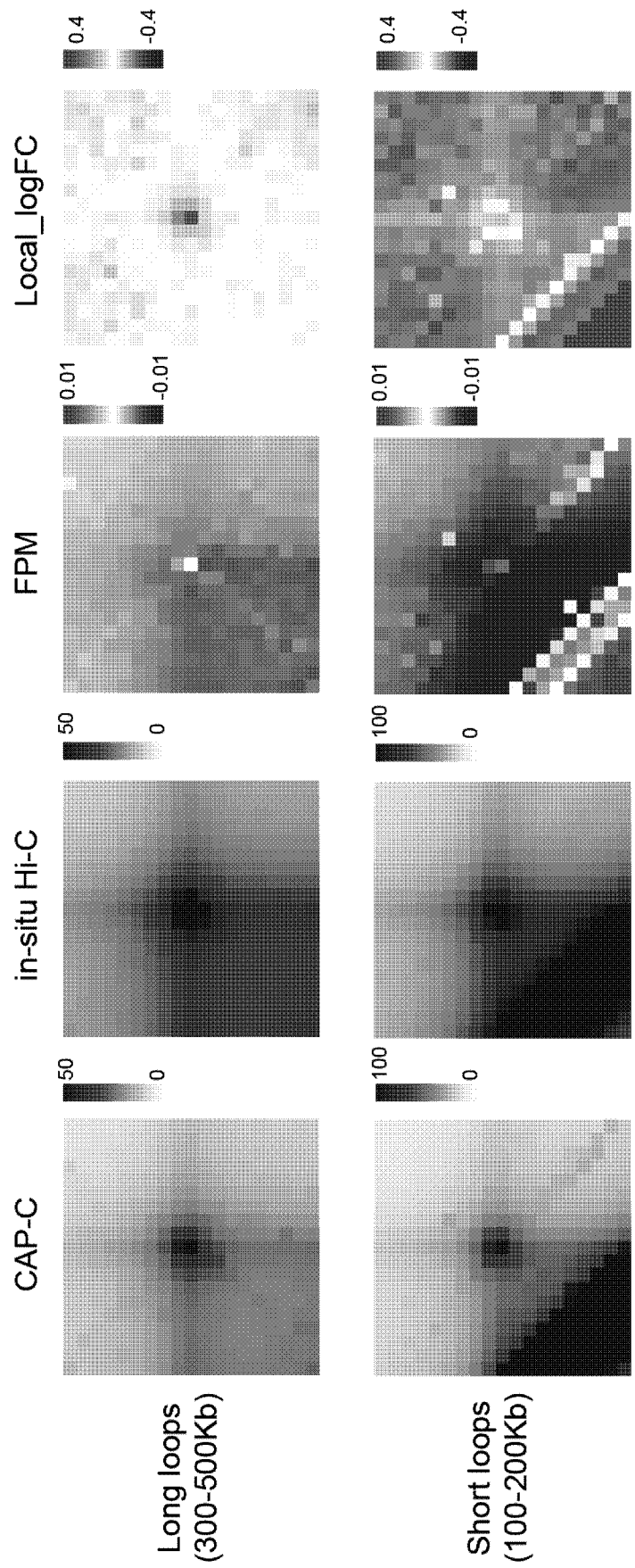
Figure 25A:
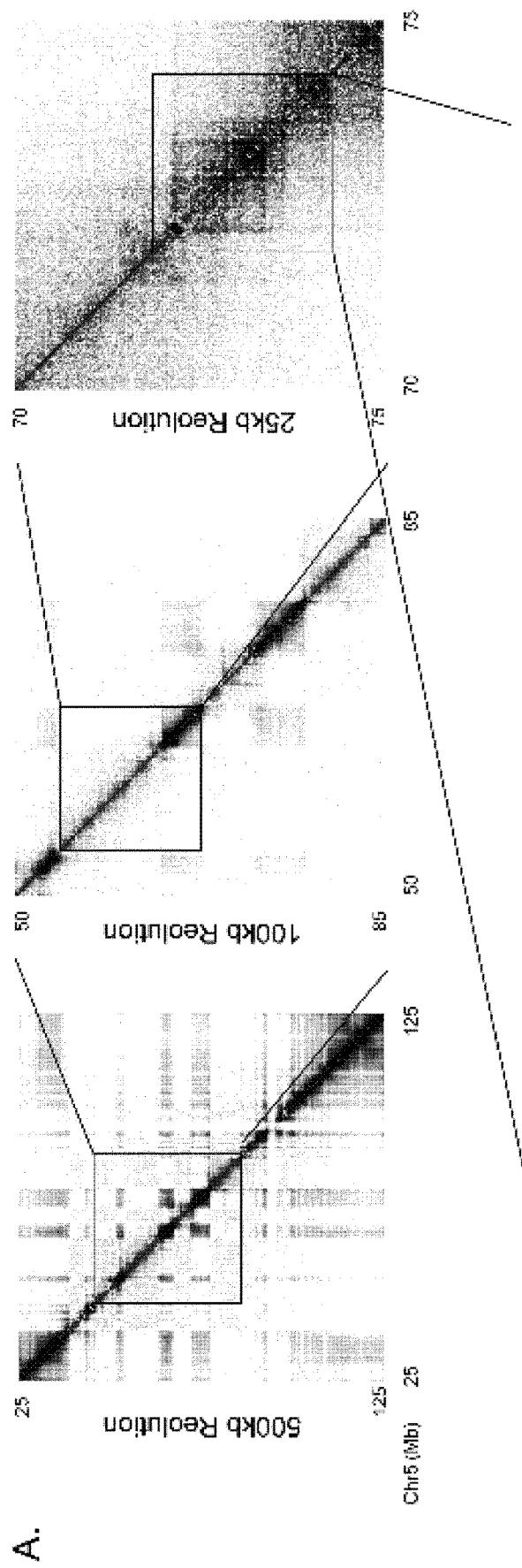
Figure 25B:
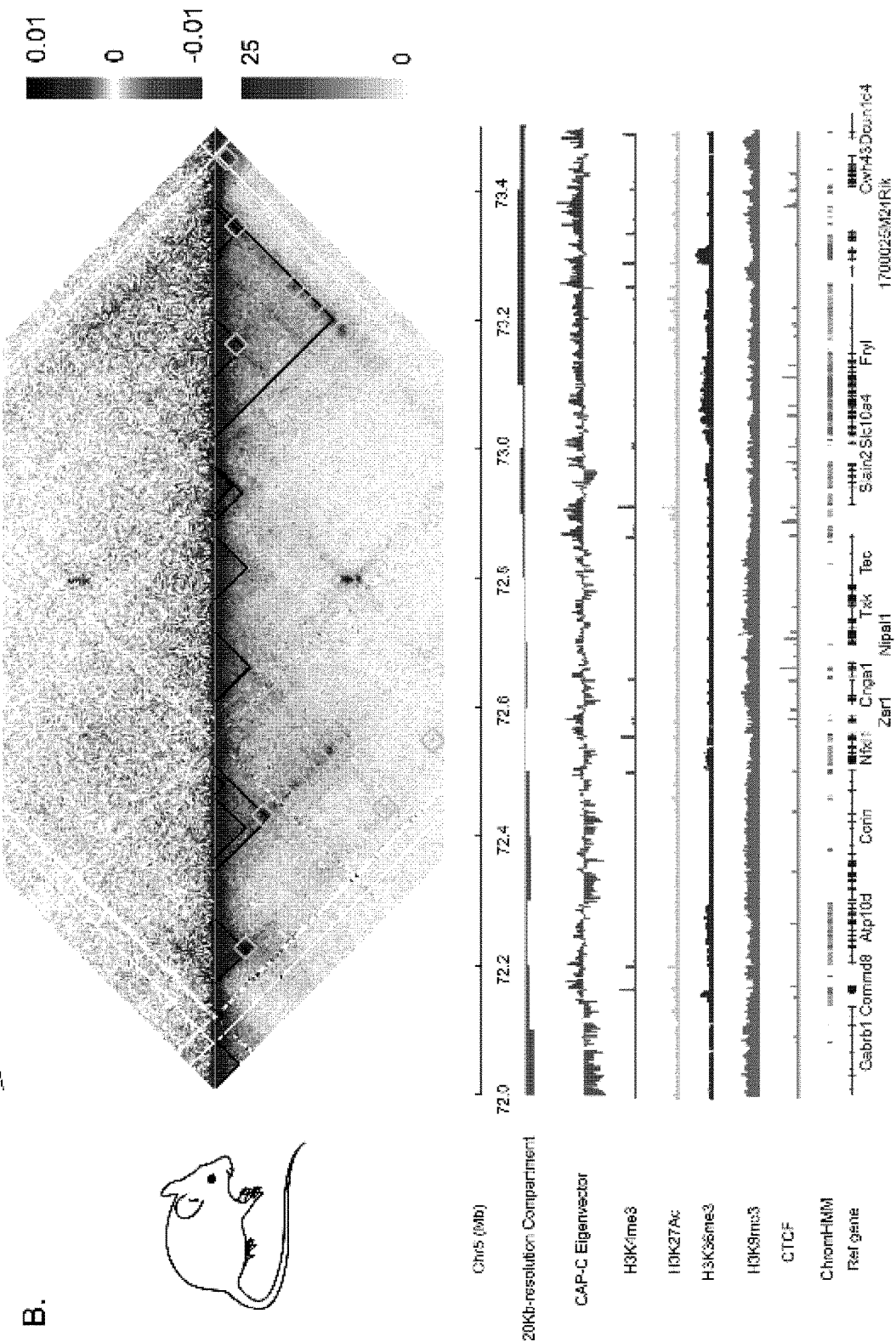
Figure 25C:
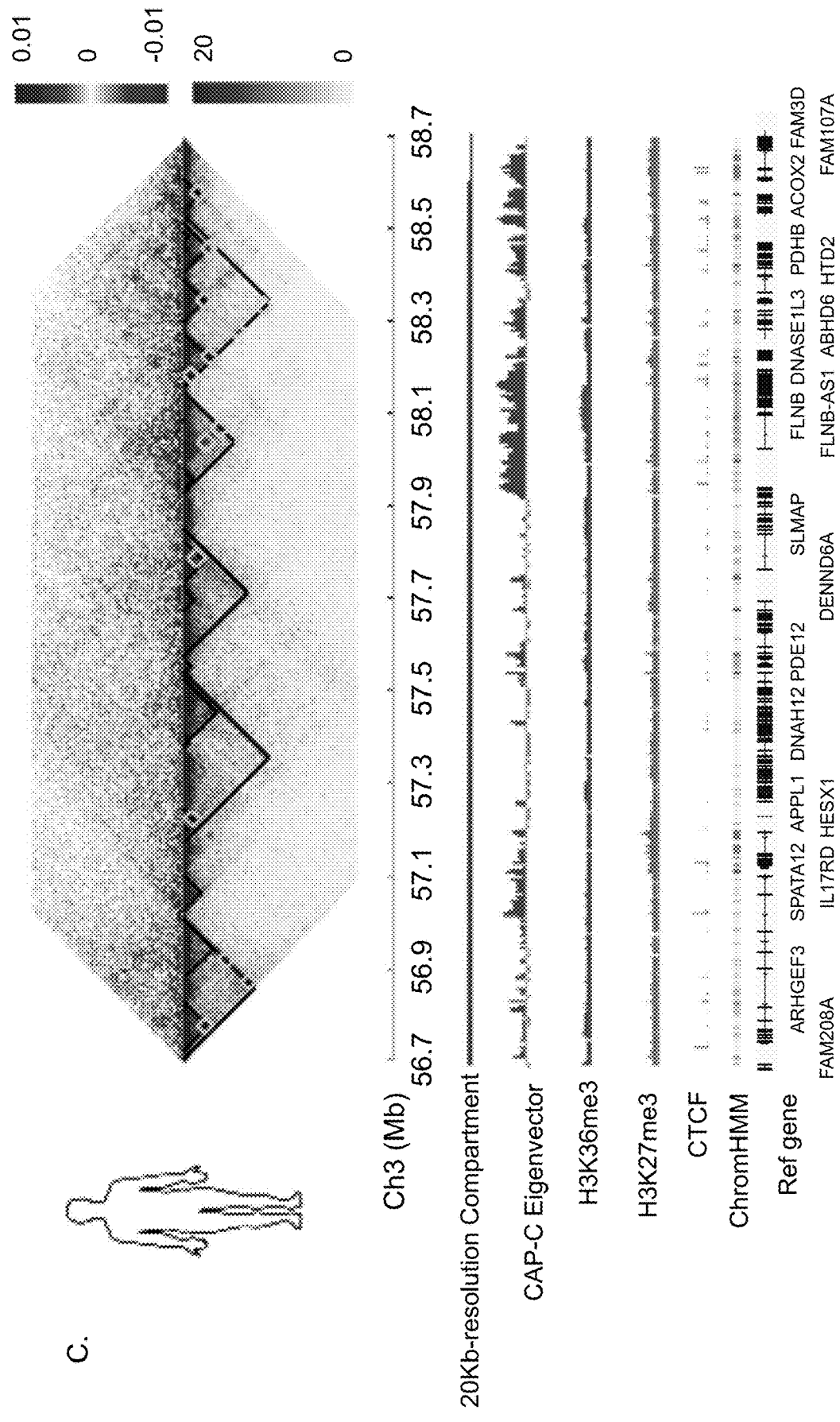
Figure 25D:
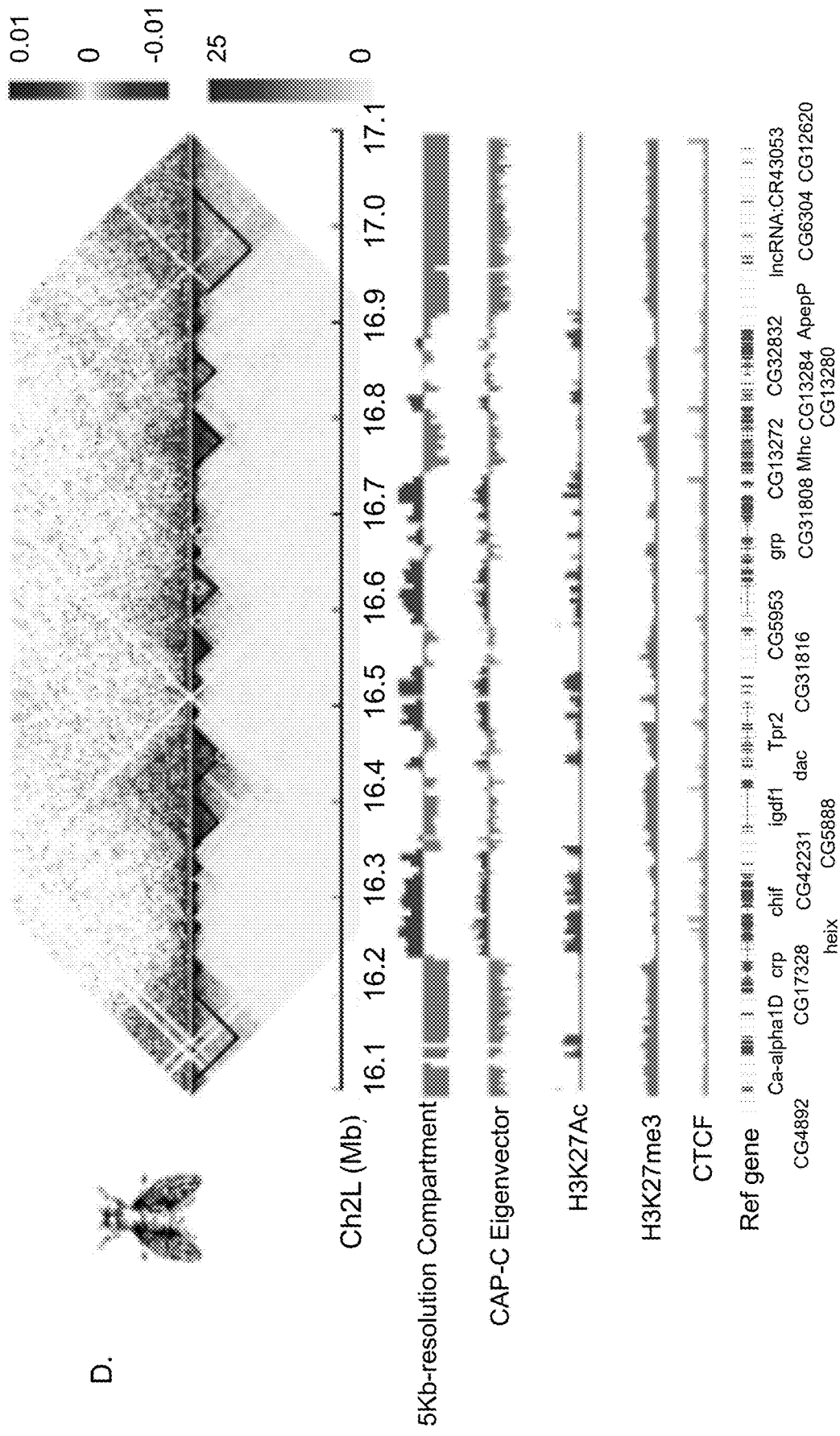

FIG. 24. CAP-C shows a higher signal to noise ratio around loop anchors over in-situ Hi-C. Meta-analysis of concordant peak calls was performed to explain why CAP-C shows a 3-fold increase in peak calls as well as an enrichment of peaks spanning short distances. When normalized for sequencing depth (FPM), the mean delta signal between the focal center of CAP-C and in-situ Hi-C maps is close to zero (column 3). However, normalizing the FPM value by the mean value of the local region, and comparing this local-normalized signal between maps (log FC) suggest a higher signal to background ratio around loop anchors in CAP-C than in-situ Hi-C (column 4). Peaks closer to the diagonal (bottom row), which are harder to call, also show higher enrichment when classified by the span of their genomic distance.

FIGS. 25A-D. Chromatin contacts detected by G5 and G7 dendrimers are enriched for compartment A whereas those detected by G3 dendrimers are enriched for compartment B. (A to D) The eigenvector with the highest eigenvalue (or a rescaled version commonly referred to as the proportion of explained variance ranges between 90 to 95%) calculated for a 3 by N*(N+1)/2 matrix (where N is the number of loci across a specified resolution) using principal component analysis yields a CAP-C map that shows a bifurcated separation that is similar to compartment intervals. Principal component loadings (bottom left arrow bars) suggest that G5 and G7 dendrimers contribute most to an open configuration while G3 dendrimer to a closed configuration. (A) In low-resolution maps, plaid-like patterns, usually associated with compartments, which are also associated with the enrichment of specific dendrimers, were observed. (B-D) The inventors examined a close-up (5 kb res) of the CAP-C map for mouse, human and *drosophila* to reveal a fine level of compartment detail. Arrowhead contact domains together with loops for each species are annotated in the bottom triangle and dendrimer maps are annotated on the upper triangle reveals that each domain adopts one type of compartment.

DETAILED DESCRIPTION OF THE INVENTION

CAP-C represents a new method for studying chromatin architecture, as well as other molecular complexes. CAP-C utilizes a multifunctional capture agent or scaffold (e.g., dendrimer) platform instead of DNA-bound proteins to crosslink DNA, achieving informative spatial chromatin organization at higher resolution than in situ Hi-C. The high resolution achieved with CAP-C is not completely dependent on the sequencing depth but stems from its ability to preserve abundant informative short-range (1-20 Kb) chromatin contacts.

CAP-C offers several distinct advantages over conventional 3C-based methods. For chromatin packed in a highly crowded environment, DNA-bound proteins block the accessibility of DNA motifs for efficient restriction digestion and subsequent ligation in conventional 3C, these proteins are stripped away in CAP-C before restriction enzyme digestion, thus exposing all potential restriction sites to favor ligation of proximal contacts at all length scales. Unlike conventional 3C, CAP-C can also reveal DNA-DNA interactions that are not mediated by protein complexes. The association of proximal DNA contacts within the same capture agent can facilitate derivation of loci-specific interactomes, by enrichment of DNA bait without ligation.

The CAP-C strategy is not limited to studying chromatin structure via proximity ligation and high throughput sequencing. Crosslinked DNA-capture agent complexes, which preserve intact chromatin structure, could be purified and coupled with other downstream methods such as electronic microscopy or fluorescent microscopy to directly visualize native chromatin structure at high resolution. In addition, the surface exposed amines can be functionalized with crosslinking groups for RNA and protein, allowing broad application of the strategy to study all potential interactions among large biomolecules.

A. Capture Agents

Capture agents or functionalized scaffolds are reagents that have a plurality of extensions or arms that can be independently functionalized with a functional group. The extensions or arms can be linkers (e.g., a polymeric chain). The capture agents have a particular size, reach, or distance between two functional groups. The functional groups have a chemical or physical characteristic for binding or capturing a target that is in the physical proximity of the capture agent. The physical distance between two targets determines the coincident interaction with a particular capture agent. The smaller the physical distance the smaller the capture agent.

In certain aspects a capture agent can have at least 2, 3, 4, 5, 6, 7, 8, 9, 10 or more functional groups. The functional groups can be various properties that can be utilized to capture 2, 3, 4, 5, 6, 7, 8, 9, 10 or targets as long as the target are compatible with the capture agent and in physical proximity. The functional groups can be or terminate in an activatable cross-linking moiety (cross-linking moiety). A cross-linking moiety can be coupled to an extension or arm of the capture agent with different arms being coupled to the same or different crosslinking moiety or functional group. Activatable cross-linking moieties can be activated by a variety of treatments and environmental conditions. In particular aspects the cross-linking moiety can be activated by light, temperature, pH. A capture agent can comprises 30, 40, or 50 to 60, 70, or 80% of the termini of an arm or linker are functionalized with a cross-linking moiety or other functional group. In certain aspects a capture agent can have 5 to 125 crosslinking moieties or functional groups. In particular aspects the capture agent has 10 to 50 crosslinking moieties.

One cross-linking moiety can be psoralen. Psoralen (7H-furo[3,2-g]chromen-7-one) is the parent compound in a family of natural products known as furocoumarins. It is structurally related to coumarin by the addition of a fused furan ring.

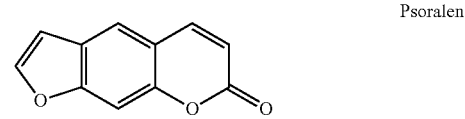 [SMILES: O=c1ccc2cc3ccoc3cc2o1]

Psoralen

In particular aspects the scaffold or capture agent is a dendrimer or a nanoparticle. In certain aspects the scaffold or capture agent has an effective diameter of about, at least about, or at most about 1, 50, 100, 150, 200, 250, 300, 350, 400, 450 to 500 nm. An effective diameter is the length between functional groups that is indicative of the physical distance between two targets that are capable of reacting or interacting with the capture agent. The capture need not be spherical or circular.

In certain aspects a functional group can be a protein cross-linker, such as diazarine. In other aspects a functional group can be a nucleic acid cross-linker, such as psoralen. A capture agent can have 1, 2, 3, 4, or more cross-linking functional groups. In certain aspects one cross-linking agent can be a nucleic acid crosslinking agent and a second cross-linking agent can be a polypeptide cross-linking agent. In another aspect one cross-linking agent can be a polypeptide crosslinking agent and a second cross-linking agent is a different polypeptide cross-linking agent. In still another aspect one cross-linking agent can be a nucleic acid cross-linking agent and a second cross-linking agent can be a different nucleic acid cross-linking agent. In particular embodiments the cross-linking moiety is psoralen.

Capture agents can further comprise a label or labeling moiety. The labeling moiety can be biotin, AVI tag, V5 tag, Myc tag, HA tag, NE tag, hexa histidine tag, calmodulin tag, polyglutamate tag, E tag, or Flag tag. In certain aspects the labeling moiety is biotin or AVI tag.

The term "dendrimer" was derived from its tree-like branching structure and refers to a hyper-branched polymer. A dendrimer for proximity capture comprises a core and a plurality of repeating units, wherein at least one activatable cross-linking moiety is coupled to a subpopulation of the repeating units. In certain one photoactivatable cross-linking moiety is coupled to a subpopulation of the repeating units. In certain embodiments, dendrimers, such as PAMAM dendrimers, allow precise control of the spherical polymer size, with different sized dendrimers serving as "molecular rulers" that fit chromatin conformations of various densities and potentially "measuring" the physical distances between two genomic loci. Different sized dendrimers offer an opportunity to discern open and closed chromatin at high resolution. Small dendrimers such as G3 favor tightly compacted, closed chromatin regions, whereas open chromatin regions are packed loosely and enrich for large dendrimers. Larger dendrimer platforms can be used to probe interactions at large scale to investigate potential communications between chromosome territories.

A dendrimer comprises a dendrimer core. In certain embodiments a dendrimer core can be propargylamine, ethylenediamine, triethanolamine, pentaerythritol, azido-propyl(alkyl)amine, hydroxyethyl(alkyl)amine, tetraphenyl methane, trimesoylchloride, diamino hexane, diaminobutane, cystamine, or propylenediamine. In particular aspects dendrimer core is ethylenediamine. The dendrimer further comprises a repeating unit or arms. In certain aspects the repeating unit is propargylamine, ethylenediamine, triethanolamine, pentaerythritol, propylamine, propyleneimine, azido-propyl(alkyl)amine, hydroxyethyl(alkyl)amine, tetraphenyl methane, trimesoylchloride, diamino hexane, diaminobutane, cystamine, propylenediamine, and lysine. In particular aspects the repeating unit is amidoamine. A dendrimer can have 1, 3, 7, 15, 31, 63, 127, 255, 511 or more repeating unit. In certain aspects the dendrimer has a diameter of about 2 to about 10 nm. It is specifically contemplated that one or more of the aspects discussed herein may be excluded from an embodiment described.

In certain aspects the capture agent is a nanoparticle. A nanoparticle can be a silicon nanoparticle, a silicon dioxide nanoparticle, metallic (e.g., gold) nanoparticle, or quantum dot having a predetermined size distribution.

B. Proximity Capture of Nucleic Acids

Chemical Platform Assisted Proximity Capture (CAP-C) is described herein. In certain aspects the methods use, for example, a psoralen-functionalized (or any other chemical functional groups for DNA, RNA, or protein crosslinking for various applications) capture agent (e.g., a dendrimer) to crosslink chromatin that is in proximity. Dendrimers are repetitively branched polymers with multiple amines on their surface, serving as a substitute for protein to covalently crosslink DNA that is in proximity, forming a stable dendrimer-DNA complex through photo induced cycloaddition between thymine on DNA strand and psoralen on dendrimers. In certain aspects a nanoparticle or similar agent presenting a plurality of arms for functionalization can be substituted for the dendrimer. The crosslinked DNA can be purified, making the subsequent restriction digestion and re-ligation much more efficient. The capture agent-DNA complexes are then purified and sheared by sonication. The ligated chimeric DNA fragments are pulled down and subjected to high-throughput sequencing. It is also contemplated that the methods can be coupled with Cryo-EM (Li et al., Nature methods 10(6):584-90, 2013) so the native chromatin structure can be preserved and observed by capture agent crosslinking with high resolution. Dendrimers are "grown" off a central core in an iterative manufacturing process, with each subsequent step representing a new "generation" of dendrimer. Increasing generations produce larger molecular diameters, while each generation of PAMAM dendrimer has defined size. In this way, different sizes of the dendrimers can serve as a "molecular probe" to measure the physical distance of certain genome loci, making it a powerful tool to study how chromosome folded in nature and re-establish the 3D model of chromatin structure. Moreover, packing and folding of the chromatin fiber would lead to co-localization of a given pair of loci, determined by other (nearby) specific long-range interactions or other constraints, or can be due to random (nonspecific) collisions in the crowded nucleus. Those "DNA-DNA" interactions present difficulties in the 3C type experiment, utilizing "protein-DNA" crosslinking. In addition, the restriction enzyme recognized motif are randomly shielded with histone or other DNA binding proteins. However, CAP-C helps to bridge two DNA elements directly, preserving those co-localizations mediated indirectly through protein binding, and bypass the incomplete digestion result from protein occupancy, leading to map the chromatin interactions with higher resolution.

The inventors validate this method by performing proximity ligation without addition of a capture agent (e.g., dendrimer) or without UV crosslinking. In this way, the dendrimer is not crosslinked to the proximal DNA strand. The inventors then performed ligation after protein digestion and subjects the ligated nucleic acids to high-throughput sequencing. The results show that without crosslinking, the long-ranged DNA interactions diminished as compared to Hi-C. While the dendrimer crosslinked samples showed similar pattern. The inventors then mapped the contacts to the MboI digested fragments and found that less than 7% can be mapped to different fragments in "no UV" and "no dendrimer" control, with large quantity of contacts (>50%) mapped to the same fragment. On the contrary, the dendrimer crosslinked library showed more than 50% distinct fragment ligation. This result demonstrated that only the chemical crosslinking can preserve the native chromatin interactions, thus validate the feasibility of this method for studying the chromatin conformation.

Moreover, psoralen can interact with structured double strand RNA, allowing this crosslinking strategy to be expanded to investigate all possible interactions among nucleic acids. By functionalizing the capture agent with a biotin handle in conjunction with crosslinking, the crosslinked RNA-dendrimer complexes can be purified, isolated, and subjected to high through-put sequencing. In this way, all possible RNA species that are spatially in proximity can be identified. Previous methods such as SPLASH and PARIS are limited by using "zero length" crosslinkers AMT, a derivative of psoralen. Such strategy can only crosslink regions of RNA strand that are reverse complement to each other. Here, by modification of the dendrimer surface with psoralen and using dendrimers of different sizes, one is able to probe more inter RNA interactions with longer distance as well as those previously identified intramolecular RNA structure. In addition, with the help of 3D RNA-FISH, the inventors could validate some of these interactions in vivo. Taking information collected using different sizes of dendrimers, it is possible to map spatially dependent RNA-interactome.

Recent studies have revealed that transcription is more prevalent than previously expected. Apart from protein-coding mRNAs, a number of long non-coding RNA (lncRNA) or other enhancer RNAs are known to be transcribed and play vital role in gene regulation as well as shaping chromatin higher order structure. Previous methods, including GRID-seq, ChIRP and CHART, relied heavily on small molecule crosslinker, providing resourceful yet limited information regarding chromatin-RNA interactome. Substituting with the chemical platform crosslinking strategy described herein, allows comprehensive localization of all or most potential chromatin-interacting RNAs in an unbiased fashion. This method includes first crosslinking DNA-RNA that are in proximity with an appropriately functionalized dendrimer (e.g., psoralen functionalized dendrimer), and removing the associated proteins. The purified complex can be further fragmented by restriction enzyme, and subsequently ligated by bivalent linker to RNA and initiating reverse transcription. After removal of excess linker, in situ DNA ligation can be performed. The ligation product can be subjected to pair end deep sequencing. Thus, the sequencing pairs could be aligned to different region of the genome to investigate chromatin-RNA interactome.

CAP-C with formaldehyde crosslinking. Cells are grown under appropriate culture conditions. Adherent cells can be detached by centrifugation and resuspended. The cells can be treated with formaldehyde. Cells can be isolated, lysed, and contacted with a dendrimer followed by photo crosslinking the nuclei. Photo crosslinked nuclei can be treated with an appropriate proteinase.

CAP-C without formaldehyde crosslinking. Cells are grown under appropriate conditions. Adherent cells can be detached by centrifugation and resuspended. Cells can be isolated, lysed, and contacted with a dendrimer followed by photo crosslinking the nuclei. Photo crosslinked nuclei can be treated with an appropriate proteinase.

After crosslinking with or without formaldehyde DNA can be extract and isolated. Isolated DNA can be treated with an endonuclease or an endo-exonuclease, e.g., MNase and the nuclease treated DNA isolated. DNA ends are repaired. Repaired DNA is treated with a biotin linker and excess of biotin linkers are removed. Biotinylated complexes are isolated and treated with a DNA ligase. To repair ends of sheared DNA and remove biotin from unligated ends, resuspend beads and treated with DNA ligase, DNA polymerase I (e.g., T4 DNA polymerase and/or Large (Klenow) Fragment. Treated DNA is further treated in a ligation reaction forming a library.

In certain aspects, nucleic acid cross-linkers include, but are not limited to psoralens, trioxsalen, methoxypsoralen, hydroxymethyl-4,5',8-trimethylpsoralen, alkylating agents such as nitrogen mustards, cis-platin, chloroethyl nitroso urea, mitomycin C, bifunctional aldehydes, and bifunctional quinone methides.

C. Proximity Capture of Polypeptides

Instead of designing a capture agent for nucleic acid, one could also modify capture agents with protein cross-linkers, such as diazarine. Most of protein-protein interactions are mediated by hydrophobic interactions and weak molecular bonds including ionic bond, van der Waals bond and hydrogen bond. Typical protein immunoprecipitation methods suffered from loss of binding target during the procedure because of the weak protein-protein interaction. Bivalent crosslinkers such DSG or derivatives to covalent crosslink the protein with its binding partners have been developed. However, such reactions require both substrates containing free amino group on its binding surface. Moreover, DSG is a highly reactive molecule and will gradually degraded in aqueous solution, restricting the application to study protein interactions ubiquitously. Diazarine, on the contrary, forms a radical upon UV irradiation. It could capture any proximal primary carbon nearby and form a covalent bond thus making it an appropriate reagent for protein crosslinking. Attaching it to the surface of a capture agent enables stabilizing those weak protein interactions. In this way, one can fish the pool of interacting or proximally located proteins via pulldown with antibodies specific to proteins of interest. The inventors could also incorporate any other cross-linkers such as DSG in our dendrimers to make it multivalent which will be much more efficient.

Despite modification of mono cross-linker, the dendrimer multiple available branches for functionalization with multiple cross-linkers. Here, the inventors could synthesize dendrimers with multiple psoralen and diazarine on the same dendrimer, which can crosslink with both nucleic acid and protein. In this way, it allows stability of the dynamic nucleic acid-interacting proteins with a dendrimer that covalently linked to the protein and its interacting DNA or RNA. After pulldown with specific antibodies, the nucleic acids are then purified and subjected to different library construction or other means of detection. These methods could be served as an improved version of current ChIP and ClIP with high signal to noise ratio. In addition, it renders the ability to investigate those proteins that have poor binding affinity to the nucleic acid with the help of different sizes of dendrimers. The conserved binding motifs are supposed to be shared among different sizes of dendrimers, and the confidence decrease as the dendrimer grows bigger. This not only allows identification of a specific protein binding region but also the distal locus that looped together.

Protein cross-linkers include, but are not limited to disuccinimidyl glutarate, disuccinimidyl suberate, disuccinimidyl tartrate, dimethyl adipimidate, dimethyl pimelimidate, dimethyl suberimidate, 1,5-difluoro-2,4-dinitrobenzene, N-maleimidopropionic acid hydrazide, 3-(2-pyridyldithio)propionyl hydrazide, bismaleimidoethane, diazarine, succinimidyl iodoacetate, N-maleimidoacet-oxysuccinimide ester, and succinimidyl 3-(2-pyridyldithio)propionate.

D. Chromatin Immunoprecipitation and Crosslinking Sequencing (ChIP-Seq and ClIP-Seq)

One imitation of chromatin immunoprecipitation sequencing (ChIP-seq) is that it requires large amounts of input material and yields 'averaged' profiles that are insensitive to cellular heterogeneity. This is a major shortcoming given that cell-to-cell variability is inherent to most tissues and cell populations. Several methods have attempted to improve current ChIP protocol and adapt to small amounts of starting materials. The inventors take advantage of the BirA enzyme, a biotin ligase that specifically transfers biotin to an AVI tag, and in vitro fused this protein with a selected antibody. The capture agents can be modified with psoralen or other functional groups in combination with an AVI tag. The cells are fixed in situ and the capture agent (e.g., dendrimer) introduced into the nucleus followed by activation of a cross-linker. A BirA/antibody fusion to target a protein of interest. After thoroughly washing away unbound antibody, biotin is supplied to initiate the transfer reaction. Since BirA only transfers biotin to proximal AVI tag, those capture agents that bind next to the target protein will be labeled with biotin. The protein is then digested and the DNA is sheared. Fragments that are specifically recognized by the biotin capture agent will be enriched and sequenced. This method can be sensitive enough to deal with low number of cells because of the high sensitivity and affinity between streptavidin and biotin compared to regular antibody antigen binding. This approach also offers a strategy to perform single-cell ChIP-seq, allowing barcoding of DNA from each cell along with pooling hundreds to thousands of cells together for pulldown and sequencing. The method can be adapted for single-cell ChIP-seq of a number of histone markers as well as other genomic features. With the same idea and effective crosslinking to RNA can perform similar methods for CLIP-seq or PAR-CLIP to study protein-RNA interactions.

In certain embodiments dendrimers carrying DNA (or RNA) crosslinkers are coupled to a specific antibody that recognizes a protein or histone marker of interest. The dendrimer can also be labeled or coupled to a tag or label, such as biotin. The cell is formaldehyde crosslinked, crosslinking DNA or RNA with proteins. The crosslinked cell lysate decorated with the antibodies coupled to the functional dendrimers, which are then subjected to a crosslinking activator. The antibody will recognize the protein in vitro and the dendrimers coupled to the antibody will crosslink to DNA or RNA bound by the protein (fixed by formaldehyde).

E. RNA Labeling Reagents

Certain embodiments are directed to RNA labeling reagents that can be used in conjunction with the methods described herein, particularly as a functional group attached to capture agent described herein. An RNA reagent can include azido-kethoxal and related kethoxal derivatives. In certain aspects the azido-kethoxal and it derivative are coupled to a functional tag. In certain aspects the RNA labeling reagent(s) have the chemical structure of Formula I

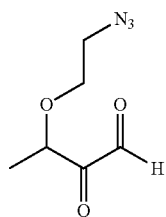

Formula II

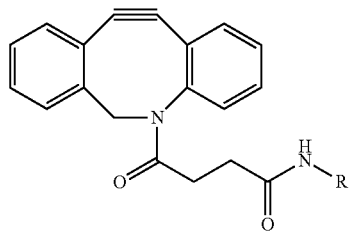

(R = Dendrimer)

Formula III

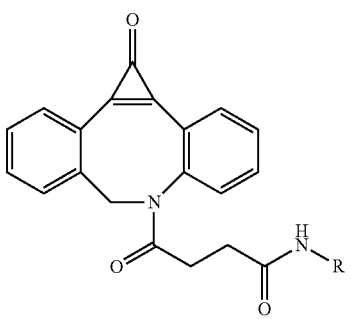

(R = Dendrimer)

The azide group can crosslink to the functional group of formula II present on the surface of a capture agent. In certain instances capture agents decorated with compounds of formula II are added at 4° C. or room temperature to cells with RNA labeled by formula I. The mixture is then incubated at higher temperature (37° C.) to initiate crosslinking. A compound of Formula II can also be generated upon photoactivation of formula III.

Kethoxal is known to efficiently label guanines in single-stranded RNA and DNA. Azido-kethoxal was designed for efficient labeling of ssRNA and ssDNA with an azido tag that can be crosslinked to formula II; formula II can be directly used, or can be generated through photo-activation of formula III.

Provided below is scheme 1 for the synthesis of azido-kethoxal.

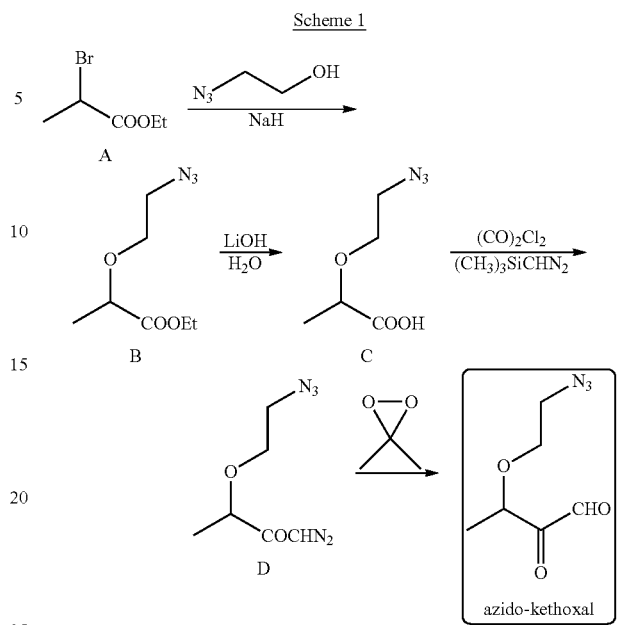

Scheme 1

A compound or Formula I can be synthesized by adding 6 g sodium hydride and 50 mL THF to a 250 mL flask and keeping the reaction at 0° C. for 15 min. 8.7 g 2-azidoethanol was dissolved in 20 mL THF and subsequently added to the reaction dropwise. The reaction mixture was stirred at 0° C. for 15 min and then warmed to room temperature for 20 min. 27.15 g compound A was added to the reaction dropwise at 0° C. after which the reaction was warmed to room temperature and stirred overnight before it was quenched by $H_2O$. The product was extracted from the mixture by diethyl ether and purified by column chromatography to yield compound B as a colorless liquid.

A compound of Formula II can be synthesized by adding 80 mL 1 M LiOH solution to 7.4 g compound B dissolved in 100 mL acetone. The reaction mixture was stirred at room temperature overnight and was subsequently quenched by adding HCl. The product was extracted from the mixture by diethyl ether and was purified by column chromatography to yield compound C as a colorless liquid.

A compound of Formula III can be synthesized by adding 1.59 g a compound of Formula II to 20 mL dichloromethane and 1.90 g oxalyl chloride was added dropwise. The reaction was then stirred at room temperature for 2 hr before the solvent was removed by vacuum. The residue was then dissolved in 50 mL acetonitrile and cooled to 0° C., to which trimethylsilyldiazomethane was added slowly. The reaction was continued at 0° C. for 1 h and slowly warmed to room temperature and stirred overnight. Solvent was then removed by vacuum and the product was isolated by column chromatography to yield compound D as a yellow oil.

Compound D was dissolved in acetone and 1.1 N fresh dimethyldioxirane was added in portions. The reaction was stirred at room temperature from 30 min and the solvent was removed by vacuum to yield azido-kethoxal as a yellow oil.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Chemical Platform Assisted Proximity Capture (Cap-C)

The inventors used CAP-C to analyze the mouse embryonic stem cell genome and uncovered two classes of chromatin domains, with one class anchored on Ctcf and cohesin binding sites while another class displayed plectoneme-like features previously only reported in prokaryotes and yeast. Further analyses revealed that chromatin domains could be arised from writhe-like structures generated through transcription-induced supercoiling. The discoveries of enrichment of condensing II at the boundaries of non-loop domain suggest that condensin loop extrusion contribute to generating non-loop domain. Despite the enrichment of such architecture protein, it was shown that transcription factors like YY1 could also be responsible for local enhancer-promoter contacts (Young et al., *Cell* 171(7), 1573-1588, 2017). These transcription activators or repressors could induce formation of local domains through. Thus, CAP-C revealed previously unappreciated chromatin domains at high resolution in mammalian cells, and can be modified to illuminate interactions among other biomolecules, including RNA and proteins.

A. Results

CAP-C: a crosslinking strategy to study chromatin architecture. To establish an approach that captures proximal chromatin contacts at all length scales, the inventors utilized a multifunctional dendrimers (PAMAM) that bear tens of crosslinking groups on the surface of polymer spheres with diameters ranging from 3-9 nm. PAMAM dendrimers are iteratively "grown" off a central core, with a new "generation" of dendrimer being synthesized at each subsequent step. Each generation of PAMAM dendrimer has a characteristic size and can be precisely tuned to control the number of surface amine groups ranging from 16-256 amines (Astruc et al., *Chemical Reviews* 110:1857-1959, 2010). The inventors used psoralen, which crosslinks to double-stranded DNA (dsDNA) upon UV irradiation, to functionalize approximately half of the surface amine branches on generation G3, G5 and G7 PAMAM dendrimers, with diameters of 3.6 nm, 5.4 nm, and 8.1 nm, respectively. The remaining amine branches were masked with acetyl groups, making them inert to cellular interactions (FIG. 6A). Psoralen-functionalized dendrimers will be referred to as dendrimers throughout the description. To confirm dendrimer functionality, different concentrations (2-25 µM) of G3 dendrimers were mixed with 10 µg genomic DNA extracted from mouse embryonic stem cells (mESCs). The inventors observed efficient crosslinking upon UV exposure (FIG. 6B). Thus, these nanometer probes can penetrate crowded chromatin environments and covalently crosslink dsDNAs, but not proteins, that are in proximity to the psoralen groups on the same dendrimer. The inventors refer to this approach as Chemical-crosslinking Assisted Proximity Capture (CAP-C).

Figure 1A:
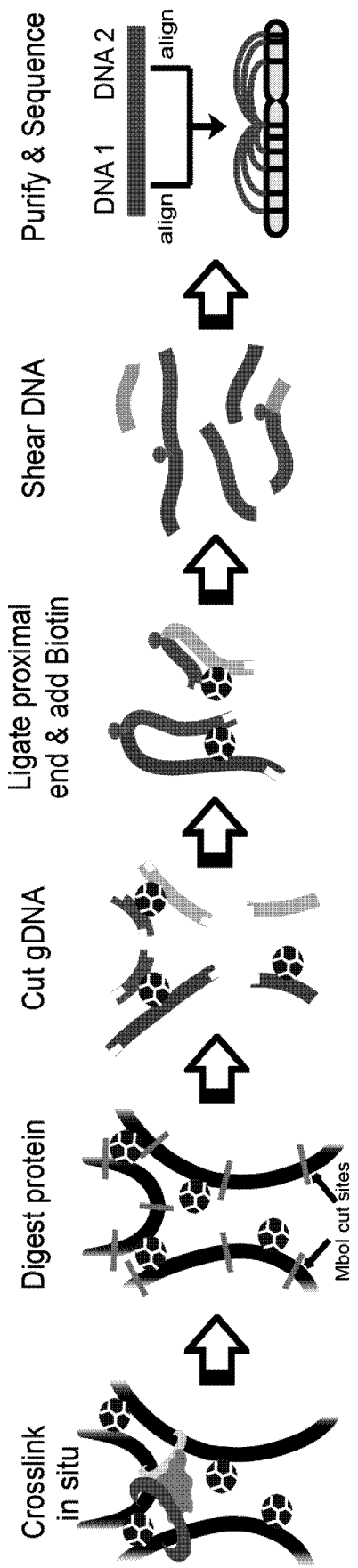
FIGS. 1A-F. CAP-C revealed higher resolution local chromatin structure compared to in-situ Hi-C at similar sequencing depths. (A) Mouse embryonic stem cells (mESs) are treated with formaldehyde to crosslink proteins with genomic DNA. Psoralen-modified PAMAM dendrimers (a capture agent) with fixed diameter (shown as balls) are diffused into nucleus. DNA in proximity are covalently crosslinked with dendrimers under UV irradiation. Proteins are digested with protease and dendrimer-DNA complexed are purified. The purified complexes, without DNA-bound proteins, are then subjected to MboI digestion and end-filling with biotin-bearing DNA, followed by proximal ligation, biotin capture and high throughput sequencing. (B) Relative contact frequency vs genomic distance curve shows CAP-C differentially enriched at short range (1-20 kb) chromatin contacts over in-situ Hi-C. The zoomed-in window shows approximately 2- to 3-fold enrichment. G3, G5, G7 represent CAP-C performed with psoralen functionalized PAMAM dendrimer generation 3, 5 and 7, respectively (with the diameters of 3.6, 5.4, and 8.1 nm). CAP-C merge represents the merging of data generated from G3, G5, and G7. (C and D) Domains are called by Arrowhead while loops are called by HiCCUPS using high resolution map with the same sequencing depth (CAP-C: 1.90 billion; in-situ Hi-C: 1.98 billion). Top left: CAP-C is able to capture more small-sized domains ranging from 5-40 kb in length. Top right: CAP-C had 2-fold more loops called genome-wide. Bottom: Overlap of domains called at different resolution and loops between the two methods. CAP-C could call more domains at high resolution (500 bp and 1 Kb). (E) CAP-C reproduces the same chromatin architecture identified by in-situ Hi-C. Top panel: 25 Kb resolution contact map of CAP-C (top right triangle) and in-situ Hi-C (bottom left triangle); bottom panel: CAP-C and in-situ Hi-C identified similar A, B compartments by PCA at 25 Kb resolution. (F) CAP-C reveals folding principle of local chromatin at high resolution. 70 Kb-long regions of CAP-C (top) and in-situ Hi-C (bottom) 1 kb resolution contact matrixes are shown corresponding to Chr4: 129.58-129.65 Mb. Histone modification and ChTP profiles are shown in the middle. Arrowhead detected 3 domains (Black triangle) in CAP-C enveloping Eif3i, Tmem234 and Txlna, respectively. Domain boundaries are highly enriched for active promoters, mediators and enhancers. No domains were detected for in-situ Hi-C at this resolution.
Figure 1B:
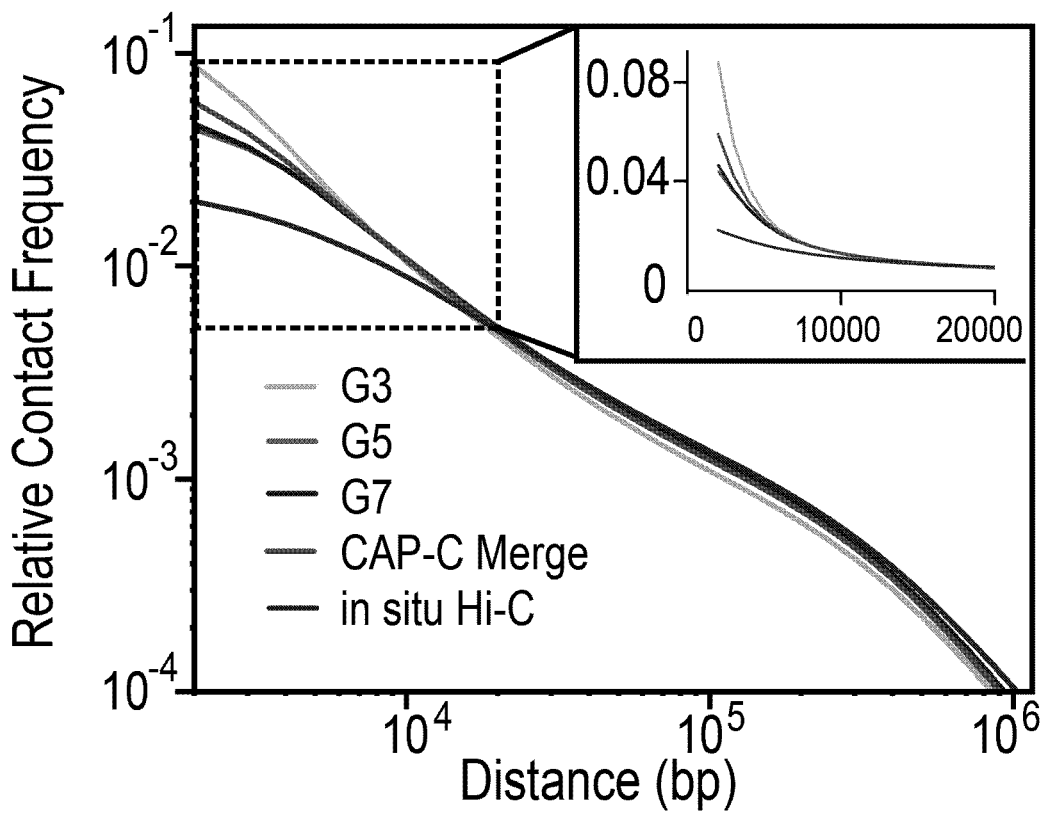

To investigate chromatin architecture using CAP-C, the inventors fix cells with formaldehyde to make sure the subsequent application of dendrimers does not perturb native chromosome conformation. The inventors then diffuse dendrimers into the cell nucleus and expose these cells to UV irradiation (FIG. 1A). The formaldehyde fixing is then reversed, and DNA-bound proteins are removed with protease to expose all DNA motifs, the dendrimer-DNA complexes are subsequently purified with ethanol precipitation. The purified dendrimer-DNA complexes are then subjected to MboI restriction digestion and end-filling with biotin-bearing DNA, followed by ligation under ultra-diluted solution, biotin capture and high-throughput sequencing (FIG. 1A). Dendrimers with a defined size were used for each CAP-C experiment.

The inventors conducted CAP-C using 10 µM G3 dendrimer with mouse embryonic stem cells (mESCs) and observed long-range chromatin contacts that required both the addition of dendrimer and UV irradiation (FIG. 7). Proteinase-K negative maps using G3 dendrimers showed a relative contact frequency vs distance plot that recapitulated in-situ Hi-C, with significantly fewer short-range interactions than G3 CAP-C maps (with proteinase-K digestion to expose most restriction sites). These data strongly suggest that protein removal promotes short-length proximal chromatin contact ligation (FIG. 8). To confirm that protein removal improves the accessibility of restriction enzymes, qPCR probes were designed to test several MboI sites. Overall, the inventors found that CAP-C yielded a higher digestion efficiency over in-situ Hi-C (FIG. 9).

Next, the inventors turned to compare CAP-C with in-situ Hi-C using mESCs. The inventors sequenced a total of 4.24 billion paired reads from six CAP-C libraries, consisting of primary and replicate libraries for each of the G3 (1.44 billion total reads), G5 (1.40 billion total reads) and G7 dendrimers (1.40 billion total reads), as well as a primary and replicate library for in-situ Hi-C (2.59 billion total reads). CAP-C datasets were processed employing a similar pipeline used for processing in-situ Hi-C libraries, followed by removal of PCR duplicates, uninformative reads, as well as reads with a low mapping quality that strongly indicate non-unique mapping (Table. 1). The inventors also performed strand orientation analysis and removed interactions below 1 Kb where read orientation is roughly equal to +/−1% (FIG. 9) (Jin et al., *Nature* 503, 290-94, 2013). The replicates for each experiment were then merged to yield a total of 732, 628, 804 and 2,093 million valid contact pairs for G3, G5, G7 and in-situ Hi-C libraries, respectively. Pearson's correlation coefficients between dendrimers were slightly lower than those between replicates of the experiments with same-sized dendrimers (FIG. 10), suggesting that dendrimers of different sizes may capture different features of chromatin organization. The inventors merged G3, G5 and G7 libraries and refer to this as the "merged CAP-C". Comparisons between primary and replicate libraries for both merged CAP-C and in-situ Hi-C showed that they exhibited high reproducibility at the 100 Kb (CAP-C: R=0.9990 and in-situ HiC: R=0.9991) and 25 Kb (CAP-C: R=0.9974 and in-situ HiC: R=0.9959) resolution (FIG. 10). Proportions of intra-chromosomal contacts were 62.1% for merged CAP-C, and 64.1% for in-situ Hi-C. To approximate the random ligation rate, the inventors compared trans-interactions between mitochondria and autosomes, which are physically separate prior to crosslinking. Here, the inventors found that even though CAP-C libraries showed 1.3-fold more mitochondria (cis+trans) interactions, there was an 8-fold enrichment of cis-interactions over in-situ Hi-C libraries (Fisher's Exact Test, P<0.0001) (Table. 2). Thus, CAP-C exhibits a lower random ligation rate than in-situ Hi-C.

TABLE 1

CAP-C Statistics

| No. listed as contact pairs | G3 | G5 | G7 | CAP-C | in-situ Hi-C |
|---|---|---|---|---|---|
| Raw | 1,445,625,597 | 1,404,085,797 | 1,404,787,973 | 4,254,499,367 | 2,591,791,329 |
| Aligned and Paired | 1,163,067,989 | 1,168,988,122 | 1,126,969,417 | 3,459,025,528 | 2,351,984,846 |
| Removal of PCR duplicates | 933,818,854 | 824,770,123 | 944,984,475 | 2,703,573,452 | 2,188,090,255 |
| Valid Pairs | 50.7% | 44.8% | 57.2% | 50.9% | 80.8% |
| Removal of unligated pairs QC Step | 732,893,486 | 628,770,646 | 804,592,946 | 2,166,257,078 | 2,093,692,590 |
| Removal of pairs <1 Kb Statistics (Valid as Denom.) | 638,816,625 | 543,095,316 | 726,331,665 | 1,908,243,606 | 1,977,866,798 |
| Intra | 445,964,733 | 376,168,868 | 522,183,654 | 1,344,317,255 | 1,342,445,880 |
| Inter | 286,928,753 | 252,601,778 | 282,409,292 | 821,939,823 | 751,246,710 |
| Intra/Inter (%) | 60.8% / 39.2% | 59.8% / 40.1% | 64.9% / 35.0% | 62.0% / 37.9% | 64.1% / 35.8% |
| Short (<20 Kb) | 513,132,022 | 420,611,868 | 487,804,616 | 1,421,548,506 | 1,089,305,644 |
| Long (>=20 Kb) | 219,761,464 | 208,158,778 | 316,788,330 | 744,708,572 | 1,004,386,946 |
| Short/Long (%) | 70.0%/ 30.0% | 66.8%/ 33.1% | 60.6%/ 39.4% | 65.6%/ 34.4% | 52.0% / 48.0% |
| MAPQ > 1 | 611,768,043 | 509,589,456 | 702,275,395 | 1,823,632,894 | 1,956,977,596 |
| MAPQ > 30 | 566,582,697 | 468,055,862 | 661,863,785 | 1,696,502,344 | 1,888,920,169 |

TABLE 2

Mitochondria reads

| chrM | CAP-C | in-situ Hi-C |
|---|---|---|
| Intra | 494,110 | 47,924 |
| Inter | 2,103,932 | 1,765,589 |
| Total | 2,598,042 | 1,813,513 |

TABLE 3

Primers designed to test MboI restriction sites

| Primer Name | Sequence |
|---|---|
| 1F | GATTTGCTCAGCAGATGGC (SEQ ID NO: 1) |
| 1R | GCAAATGCCCAGAGGTTC (SEQ ID NO: 2) |
| 2F | CTACCCAGAAACAGCAAGTG (SEQ ID NO: 3) |
| 2R | TTTCTGTGTTGCTATTCGGTA (SEQ ID NO: 4) |
| 3F | CATCAGATTAAGGGCGCCA (SEQ ID NO: 5) |
| 3R | ACGCAGTAGGAGACCGG (SEQ ID NO: 6) |
| 4F | GCTTTCCTCATGGAAATGC (SEQ ID NO: 7) |
| 4R | CAGGCACAGCCTCGT (SEQ ID NO: 8) |
| 5F | ACGTGGCTGAGGCTGA (SEQ ID NO: 9) |
| 5R | TCTCTGGCTCACTCACC (SEQ ID NO: 10) |
| 6F | TTCTCTCATCTGCACCGG (SEQ ID NO: 11) |
| 6R | CAGGCGGAAGTGACGT (SEQ ID NO: 12) |
| 7F | AGGACCATCTGTGCACGGAG (SEQ ID NO: 13) |
| 7R | GGTTACGCATGCAGAGCC (SEQ ID NO: 14) |
| 8F | CACCCCAAGGGCTTAGA (SEQ ID NO: 15) |
| 8R | AAGGATGCTCCACCACC (SEQ ID NO: 16) |
| 9F | CATAGACGAGTCATTGTTTCG (SEQ ID NO: 17) |
| 9R | GCCCTCTGGTGGAGACAT (SEQ ID NO: 18) |
| 10F | CCAGAGGCTGTGGCTTC (SEQ ID NO: 19) |
| 10R | CAAGAGACAGCTAAATCAGGGT (SEQ ID NO: 20) |
| 11F | CTTATCGACTGTTGCCATGG (SEQ ID NO: 21) |
| 11R | CTTAGCCTTGGTATCAACTGG (SEQ ID NO: 22) |
| 12F | GGGAGTAGAAAGAAGGCCC (SEQ ID NO: 23) |
| 12R | GGCATTTCACCTCACTGCA (SEQ ID NO: 24) |
| 13F | TCTATAAAGATGCCTCTGAGGT (SEQ ID NO: 25) |
| 13R | TCTGCTTCATTGAGAATTTACAG (SEQ ID NO: 26) |
| 14F | TATAGGTTGGCTCCAAGCTCT (SEQ ID NO: 27) |
| 14R | GATACCTGATTCAGATGGTGCA (SEQ ID NO: 28) |
| 15F | GACATCCTGCCTTCCCTG (SEQ ID NO: 29) |
| 15R | GTGGGTCAAGTTCTCAATGG (SEQ ID NO: 30) |

TABLE 3 -continued

Primers designed to test MboI restriction sites

| Primer Name | Sequence |
| --- | --- |
| 16F | TACTGACTCTGACACCAGATG (SEQ ID NO: 31) |
| 16R | CATGAGACTGACTTAAGCATCT (SEQ ID NO: 32) |

TABLE 4

Published Datasets

| Description | Reference | Availability |
| --- | --- | --- |
| H3K4me3 | Mouse ENCODE consortium | ENCODE |
| H3K9me3 | Mouse ENCODE consortium | ENCODE |
| H3K27ac | Mouse ENCODE consortium | ENCODE |
| H3K27me3 | Mouse ENCODE consortium | ENCODE |
| H3K36me3 | Mouse ENCODE consortium | ENCODE |
| Pol2ra | Mouse ENCODE consortium | ENCODE |
| H3K9me2 | Liu et al. | GSE54412 |
| Ctcf | Hansen et al. | GSE90994 |
| Rad21 | Hansen et al. | GSE90994 |
| Smc1 | Kagey et al. | GSE22557 |
| Smc3 | Kagey et al. | GSE22557 |
| Med1 | Kagey et al. | GSE22557 |
| Med12 | Kagey et al. | GSE22557 |
| PRO-seq | Engreitz et al. | GSE85798 |
| Smc3 ChIA-PET | Dowen et al. | GSE57913 |
| Smc3 HiChIP | Mumbach et al. | GSE80820 |
| ATAC-seq | Wu et al. | GSE66390 |
| TADs annotations | Dixon et al. | chromosome.sdsc.edu/mouse/hi-c/mESC.doma.tar.gz |
| ChromHMM states | Bogu et al. | github.com/gireeshkbogu/chromatin-states_chromHMM_mm9 |
| Replication Timing | Hiratani et al. | replicationdomain.com/data.php |

Figure 1C:
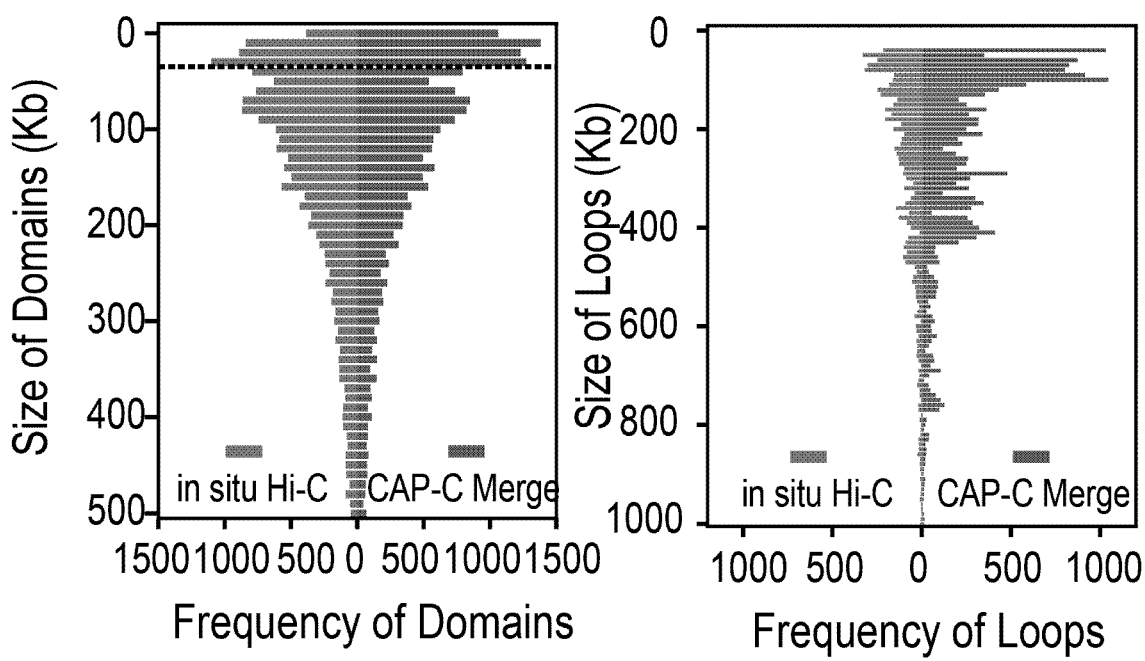
Figure 1D:
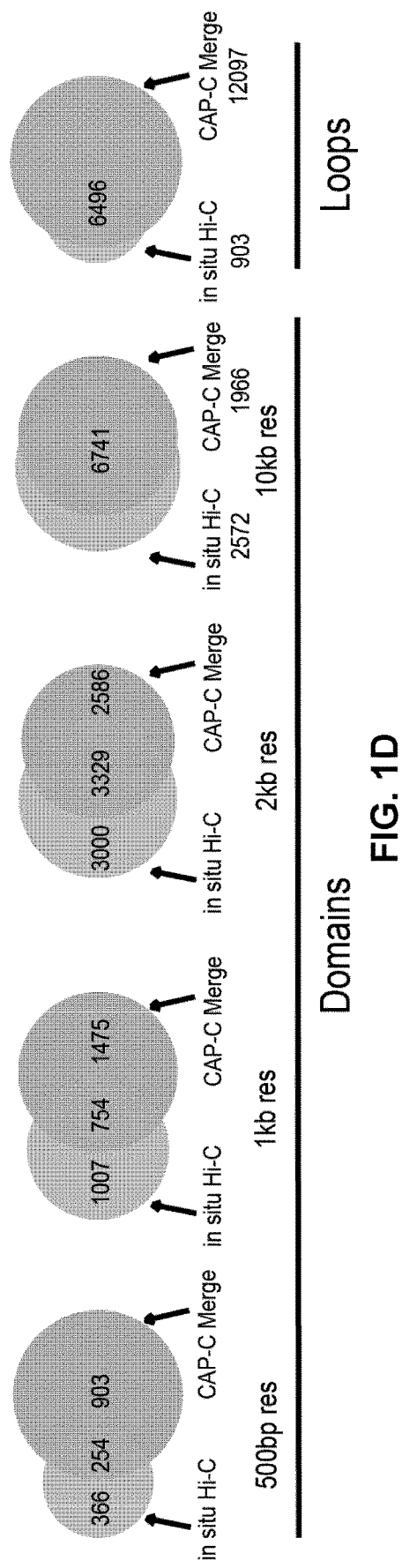
Figure 1E:
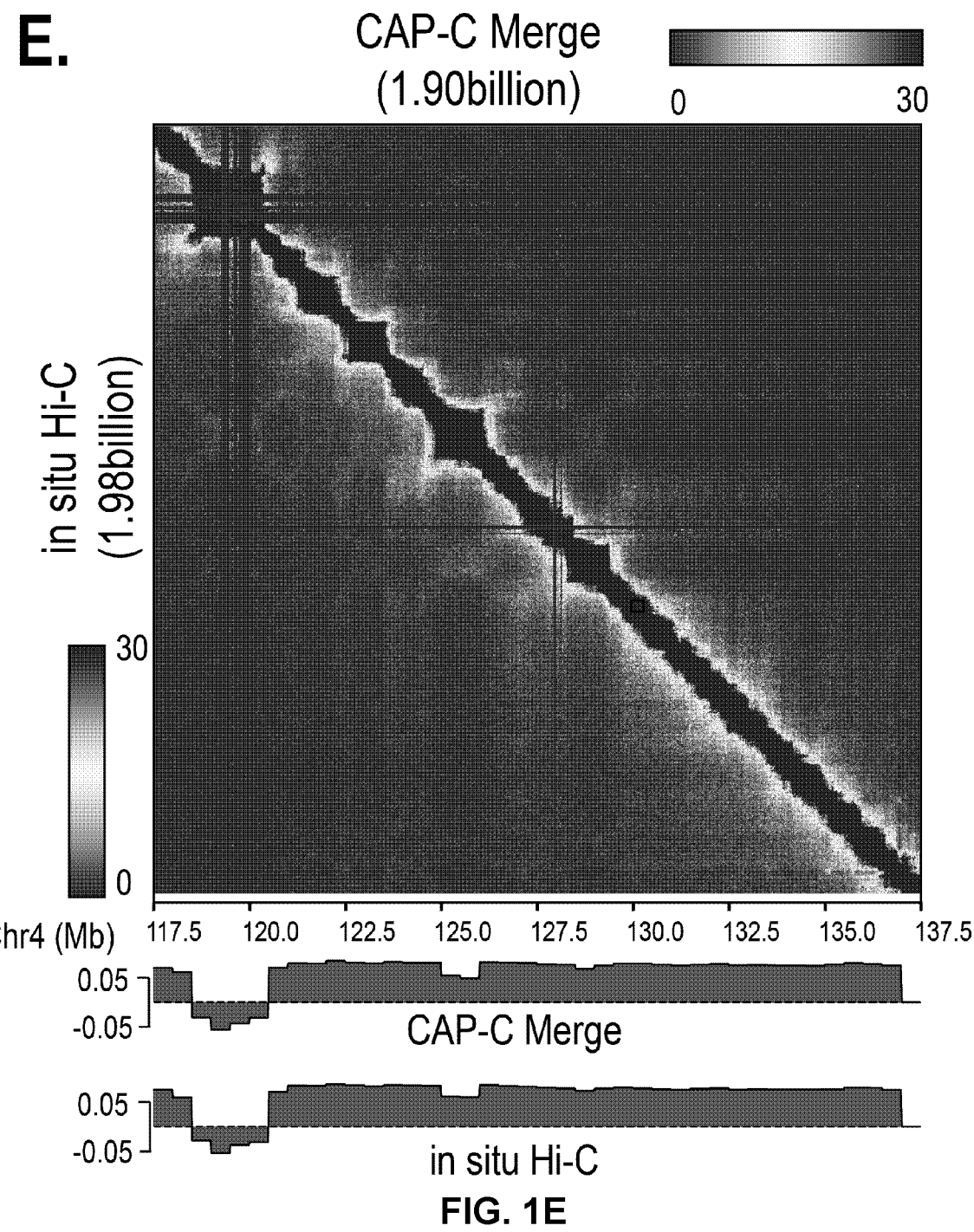

CAP-C revealed finer local chromatin structures than in-situ Hi-C. The inventors hypothesized that different sized dendrimer crosslinkers will capture distinct spatial relationships at different length scales. Indeed, the smallest dendrimer, G3, strongly crosslinked loci between 1 to 5 Kb in distance, whereas G5 and G7 dendrimers preferentially crosslinked loci with distances between 5 to 20 Kb. The total chromatin contacts between 1-20 Kb captured by merging all dendrimer data were 2-3 folds greater than for in-situ Hi-C (FIG. 11n). This gain in short-range interactions was offset by a relative reduction of long-range contacts after 1 Mb, however, contact maps plotted for a series of CAP-C resolutions showed similar chromatin features, such as compartments or TADs, as in-situ Hi-C (FIG. 1E).

Figure 1F:
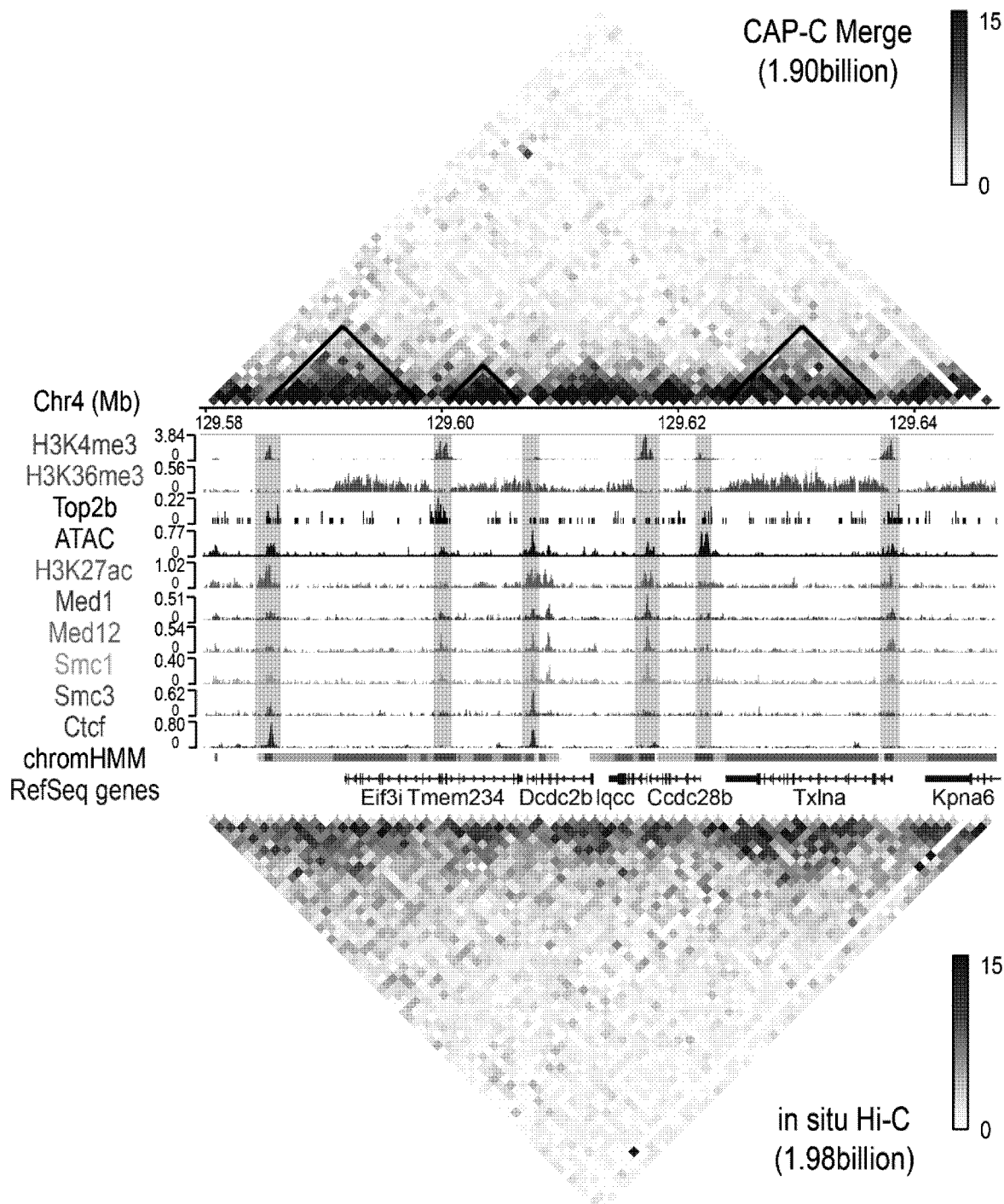

In contrast to higher-order chromatin structures that have been studied extensively by Hi-C, enrichment of short-range CAP-C contacts allowed us to better resolve new features of the genome at shorter length-scales. For comparison, contact maps of merged CAP-C and in-situ Hi-C datasets with similar depths (1.90 billion vs 1.98 billion) were plotted over a 70 Kb region (chr4:129.58-129.65 Mb) encompassing 6 different genes at 1 Kb resolution (FIG. 1F). At this resolution, CAP-C maps were clearer and sharper, enabling us to visually inspect promoters, enhancers and actively-transcribed genes when placed alongside a ChromHMM track (Ernst and Kellis, Nature Protocols 12, 2478, 2017). Many of the small triangles with enhanced contact frequency close to the diagonal (FIG. 1F) were observed in CAP-C, and were called as domains by using Arrowhead (Rao et al., Cell 159, 1665-1680, 2014) at 1 Kb resolution, which were not distinguishable as domains in in-situ Hi-C maps with a similar sequencing depth. Because contact maps consist of an ensemble of individual chromatin conformations across millions of cells, the inventors do not assume that the genome can be partitioned into non-overlapping intervals. Thus, the inventors called domains using Arrowhead at a series of resolutions (500 bp, 1 Kb, 2 Kb, 5 Kb and 10 Kb) and merged the call sets (nested and non-nested) into a unique but possibly overlapping set of domains. Identical domains were merged, and domains with similar boundaries were removed based on the Euclidean distance criteria of min (0.2*shortest-length, 50000). Compared to in-situ Hi-C maps, CAP-C maps called 1.5-fold more domains with sizes of 5 to 40 Kb, but 1.2-fold fewer domains with sizes greater than 40 Kb (FIG. 1C, left). Boundaries of these smaller-sized domains (5-40 Kb) called in CAP-C tend to strongly overlap with active promoters and enhancers. In contrast, the smaller-sized domains called in in-situ Hi-C tend to overlap with heterochromatin.

At similar sequencing depths, high-resolution peak calling using HiCCUPs yielded more peaks (2.5-fold) with merged CAP-C contact maps than with in-situ Hi-C libraries. Proportionally, there was a 1.4-fold enrichment of peaks from CAP-C that were less than 100 Kb in size than peaks from in-situ Hi-C (Fisher's Exact Test, P<0.0001) (FIG. 1C, right). 87.7% (6,496) and 61.9% (7,344) of in-situ Hi-C and HiChIP peaks (Mumbach et al., Nat. Methods 13, 919-922, 2016) were concordant with merged CAP-C, suggesting that peak calling was more sensitive in CAP-C than in-situ Hi-C. Meta-analyses performed on short (100-200 Kb) and long (300-500 Kb) concordant peaks between CAP-C and in-situ Hi-C suggested that even though depth-normalized signal values (FPM) at the foci were similar between maps, a faster decay in mean long-range contacts between the two anchors decreases the mean lower-left background values in CAP-C. This effect significantly increases the signal-to-noise ratio and consequently increases the number of peaks called at a constant threshold (FIG. 11). Indeed, contacts around loop anchors are expected to be low, as polymer models predict that long idealistic loops should not exhibit contacts anywhere except at the anchors where they meet (Fudenberg et al., Cell reports 15, 2038-49, 2016; Benedetti et al., Nucleic Acids Res. 42, 2848-55, 2014), suggesting that CAP-C identifies loops better than in-situ Hi-C. Further, 76.3% of unique Ctcf motifs were in the convergent orientation (FIG. 12), which is similar to results reported previously (Rao et al., Cell 159, 1665-80, 2014) and validates the reliability of peaks called in CAP-C.

Different sized dendrimers probe different chromatin compartments. Different sized dendrimers might also access and probe distinct regions of chromatin compaction. This would be revealed by dendrimer size-dependent enrichment of interactions in distinct regions. Using principal component analysis, the inventors determined the eigenvector with the highest eigenvalue using the pixel values of each G3, G5 and G7 contact maps and plotted a 2D map which the inventors named as "dendrimer map" based on the eigenvector values of the $1^{st}$ principal component. At multiple resolutions (500 Kb, 100 Kb, 10 Kb and 5 Kb), the $1^{st}$ principal component tended to explain 90-95% of the variance instead of 50% for random contact map. Most importantly, these "dendrimer maps" showed bifurcation similar to that of compartment intervals identified previously (Lieberman-Aiden et al., Science 326, 289-93, 2009) (FIG. 2, A to D). Statistical analysis of low resolution (100 Kb) maps also yielded similar insights (see Materials and Methods). In low resolution maps, the inventors observed differential separation along compartment intervals best represented by checkerboard patterns. Principal component loadings suggested that G5 and G7 dendrimers mostly detect interactions within open configuration chromatin, whereas G3 dendrimers identify more interactions within closed configuration. Thus, the inventors hypothesized that the "dendrimer map" the inventors produced could reflect A/B compartment identified by Hi-C; G5 and G7 dendrimers could capture more contacts within compartment A while G3 dendrimers identify more interactions within compartment B.

Figure 2D:
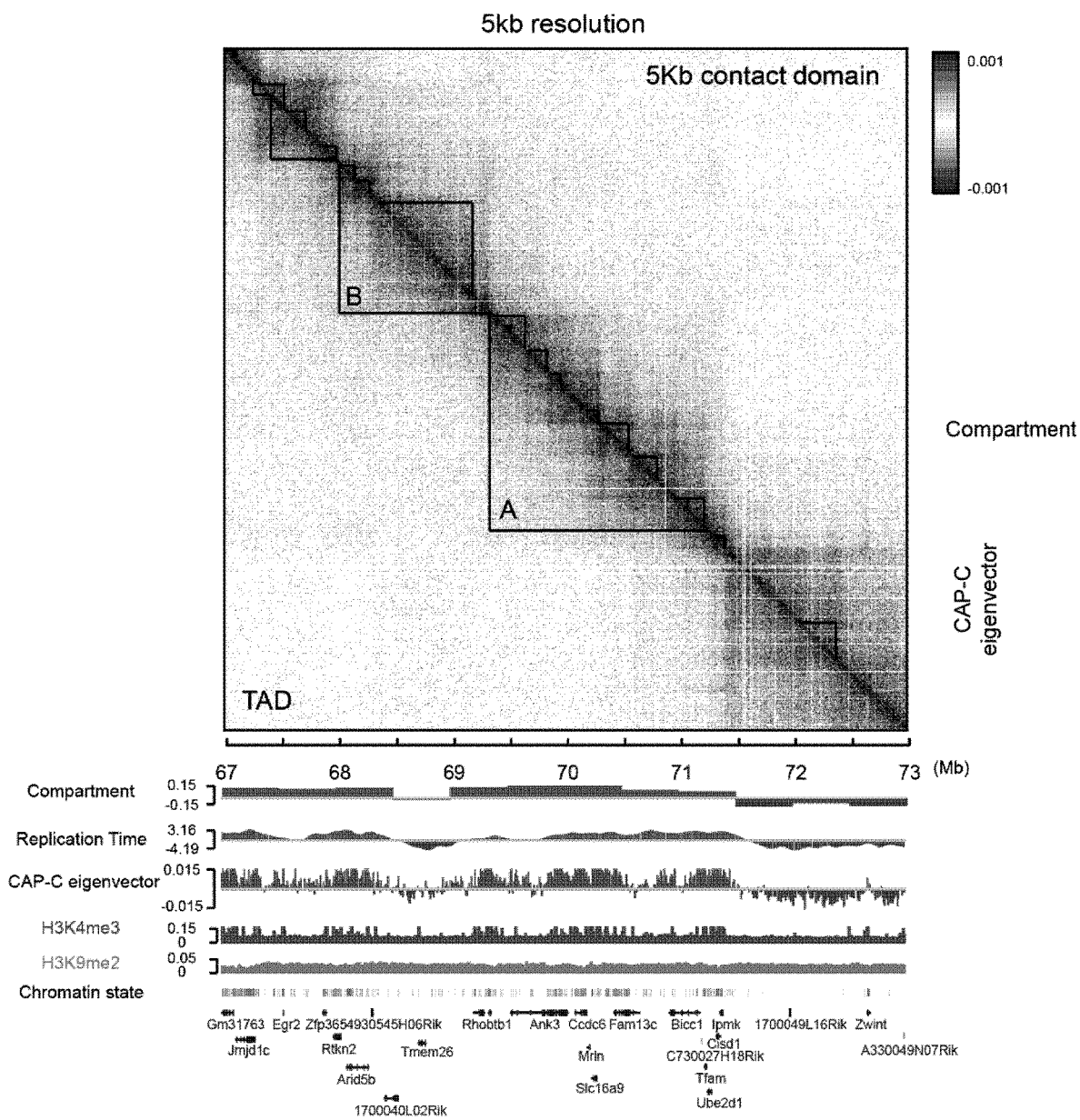
Figure 2E:
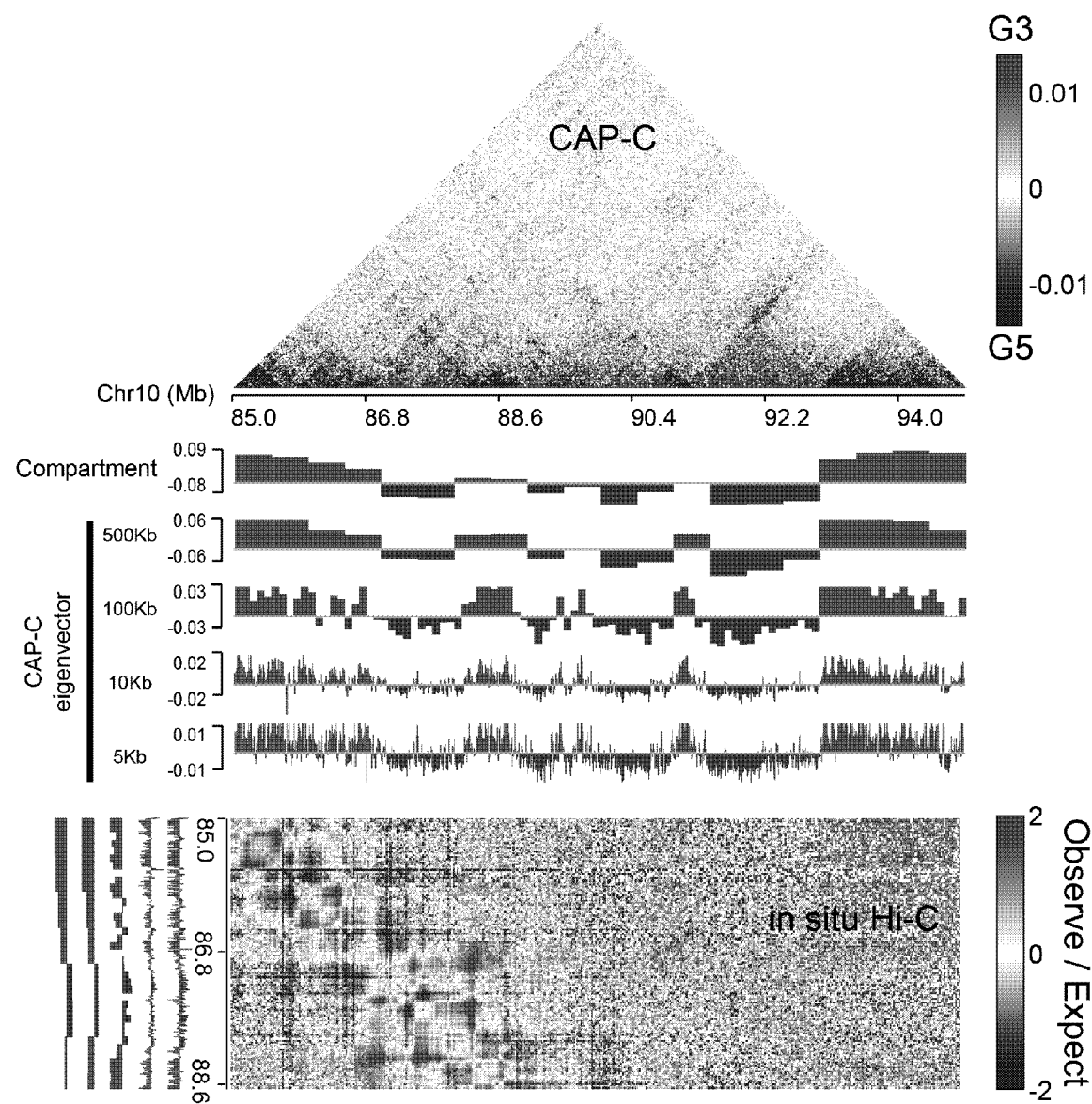

To validate above hypothesis, the inventors produced "CAP-C eigenvector" similar to the eigenvector constructed previously in determining compartments by performing principal component analysis on the row sums, instead of the pixels, of all three dendrimer contact maps, and arbitrarily assigned positive values to regions which are gene-rich. Indeed, our "CAP-C eigenvectors" showed good positive correlations with compartment intervals derived from the eigenvector analysis on in-situ Hi-C at 500 Kb resolution (Pearson's R=0.861), and replication timing data from RepliSeq experiments in mESC (Pearson's R=0.850) (Hiratani et al., PLoS Biol. 6, e245, 2008) as well as moderately negative correlation with H3K9me2 ChIP-Seq (Pearson's R=−0.329) (Liu et al., Genes Dev. 29, 379-93, 2015), a histone modification mark for constitutive heterochromatin in mESC (FIG. 2D, bottom tracks). Moreover, the inventors obtained "CAP-C eigenvectors" in a series of resolution and discovered smaller compartment intervals that are tens of kilobases in length, which were missed in the compartments calculated using the Pearson matrix of low resolution in-situ Hi-C maps (FIG. 2E). Given that G3 and G5 are sufficient to describe a distinction between compartment A and B, the inventors plotted a delta map (difference in FPM) between G3 and G5 and observed the co-localization of compartment intervals with similar types (A/B) compared with 25 Kb resolution O/E maps of in-situ Hi-C, further proving that "CAP-C eigenvector" values are reflective of compartments.

The inventors next inspected the "dendrimer maps" at the 5 Kb resolution to reveal additional compartment details that are missed in previous low resolution Hi-C experiments (FIG. 2D). When associating with chromatin states, the inventors observed heterochromatin with negative CAP-C eigenvalue interspersed between gene-rich A compartments while smaller active open chromatin region with positive CAP-C eigenvalue were embedded in compartment B intervals. Such features were not detected in low-resolution Hi-C maps, indicating that CAP-C captures finer details of chromatin conformation. Moreover, overlapping mESC TAD annotations (FIG. 2D, bottom left matrix) and high-resolution (5 Kb) contact domains (FIG. 2D, upper right matrix) revealed a complex relationship between compartments and domains. The smaller compartment intervals revealed in CAP-C is further supported by recent studies using a variety of experimental techniques and newer computational methods.

In summary, the above analyses confirmed that smaller G3 dendrimers preferentially crosslink tightly packed heterochromatin in B compartments, whereas the larger G5 and G7 dendrimers tend to capture chromatin contacts in the open and gene-rich compartments (FIG. 13). Thus, different sized dendrimers enrich in different regions of the genome. These fixed-size probes could be used as nanometer-scale molecular rulers to infer physical distances among different genomic loci.

Two types of chromatin domains with different boundary properties. Given that our dendrimer maps showed high correlation between transcription and genome segregation, the inventors investigated how transcription affects the formation of the contact domains the inventors discovered. Recent studies using biophysical models have proposed different mechanisms to explain the self-associating and insulating properties of chromosomal domains in prokaryotes as well as in mammals. In model organisms such as C. crescentus and S. pombe, which lack Ctcf, polymer models attribute transcription-induced supercoiling as the force responsible for conformational changes in the form of writhes termed plectonemes. Boundaries of these domains, generically termed chromosomal interacting domains (CIDs), span the transcriptional start sites of active genes. On the contrary, the detection of TADs enriched with Ctcf at its boundaries in low-resolution maps, followed by the identification of Ctcf-cohesin-mediated loops and loop-domains in high-resolution maps, suggested that loop extrusion might be responsible for chromatin organization in mammals. However, the loop extrusion model may not explain the self-association property in large TADs unless supercoiling is taken into account. Hence, it is not entirely clear whether chromatin loop domains form in mammals exclusively via the loop-extrusion model, or whether multiple mechanisms underlie loop domain formation. To further complicate matters, only 30% of our high-resolution contact domains show loops at the corners of loop-domains and 65% of the same contact domains overlap Ctcf (+/−10 kB), implying that not all Ctcf-enriched boundaries form loops. In our high-resolution maps, the inventors noticed that a substantial proportion of contact domains called at high resolution revealed boundaries starting close to the promoters of short active protein-coding genes, which either terminate at their own transcription end sites (TSS), or halfway through the gene body of another gene (FIG. 1F).

The boundaries of domains starting at active promoter regions have been previously characterized in S. cerevisiae and recently observed in mESCs. The associations of CAP-C loops with histone modifications and transcription factor features around their anchor points suggest that the increased loops captured in CAP-C are not artifacts but functionally similar with loops identified in in-situ Hi-C (FIG. 3, H and I). In this instance, the inventors merged contact domains called at high-resolution (500 bp, 1 Kb, 2 Kb) into a unique set, and classified the contact domains into loop and non-loop domains, based on whether they are associated with Ctcf-mediated loops. Segregating and plotting the distributions of the number of protein-coding genes per domain and size of domains showed striking contrast between these two "arbitrary" types of domains. Non-loop domains are overwhelmingly shorter, and possess at most one protein coding gene, whereas loop domains are longer and contain 1 or more protein-coding genes (FIG. 3, C and D).

Figure 3A:
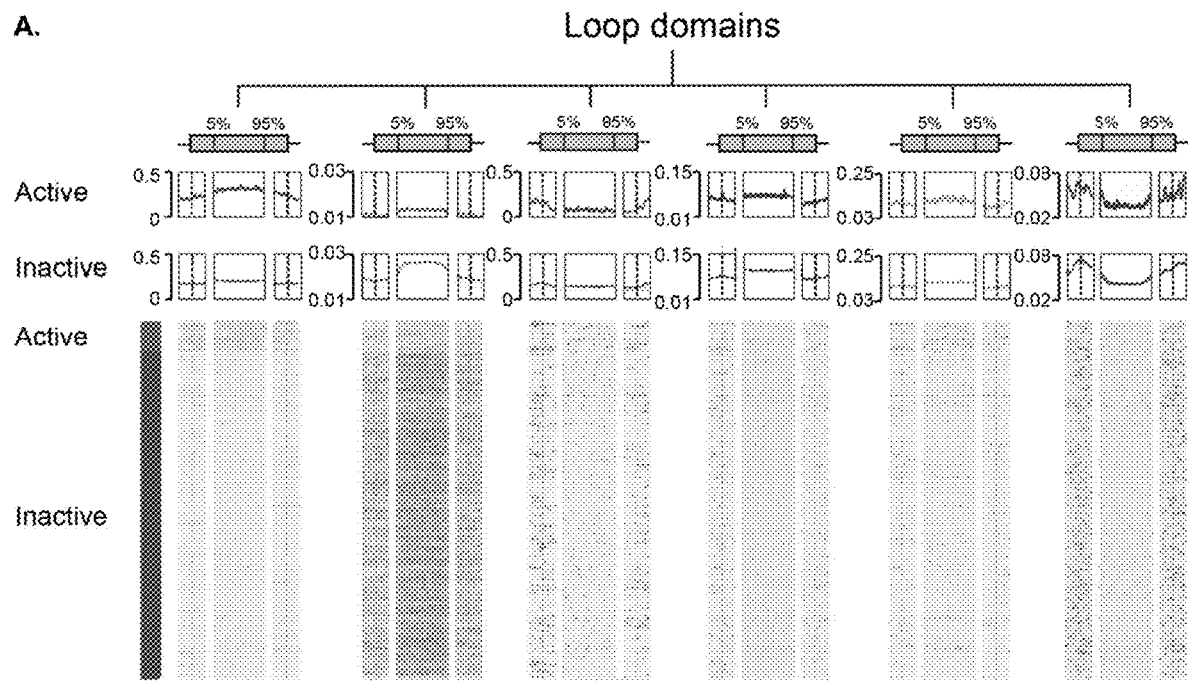
FIGS. 3A-I. Loop and non-loop domains show different boundary properties. (A and B) Meta-domain analysis shows two independent mechanisms responsible for domain formation. Segregating domains (called using high-resolution maps) into loop and non-loop domains indicate that boundaries of non-loop domains are enriched in RNA-polymerase binding as well as promoter and enhancer status while loop domains are enriched in CTCF binding. (C and D) Comparison of length distribution between loop domains and non-loop domains shows that non-loop domains are generally shorter and encompass a single protein-coding gene or not (i.e., domains spanning promoter-enhancer boundaries) while loop domains are longer and have one or more protein-coding genes per domains. (E) Plectoneme-free region causes strong separation and leads to domain formation. Pairs of protein-coding genes were classified by transcription directions oriented in divergent, tandem and convergent manner. Top panels show interaction counts for the three classes. Bottom panels show the same data expressed as the log 2 ratio of observed interactions divided by expected interactions for a given genomic distance. Boundaries were strongest at divergent pairs. (F and G) By classifying promoters based on chromHMM states and associating them with both CAP-C eigenvector and DI calculated at 2 Kb resolution, it was observed that the presence of RNA polymerase at the transcription start site and its increasing levels of elongation is strongly associated with openness and the strength of boundaries. (H and I) CAP-C captures more loops which are not functionally different from in-situ Hi-C. (H) Loops are classified by using histone modification and transcription factor features based on their upstream (L) and downstream (R) anchors around a +/−5 Kb region. (I) Based on these states, the bar chart revealed that the proportion of different classes of loops are similar between CAP-C and in-situ HiC.
Figure 3B:
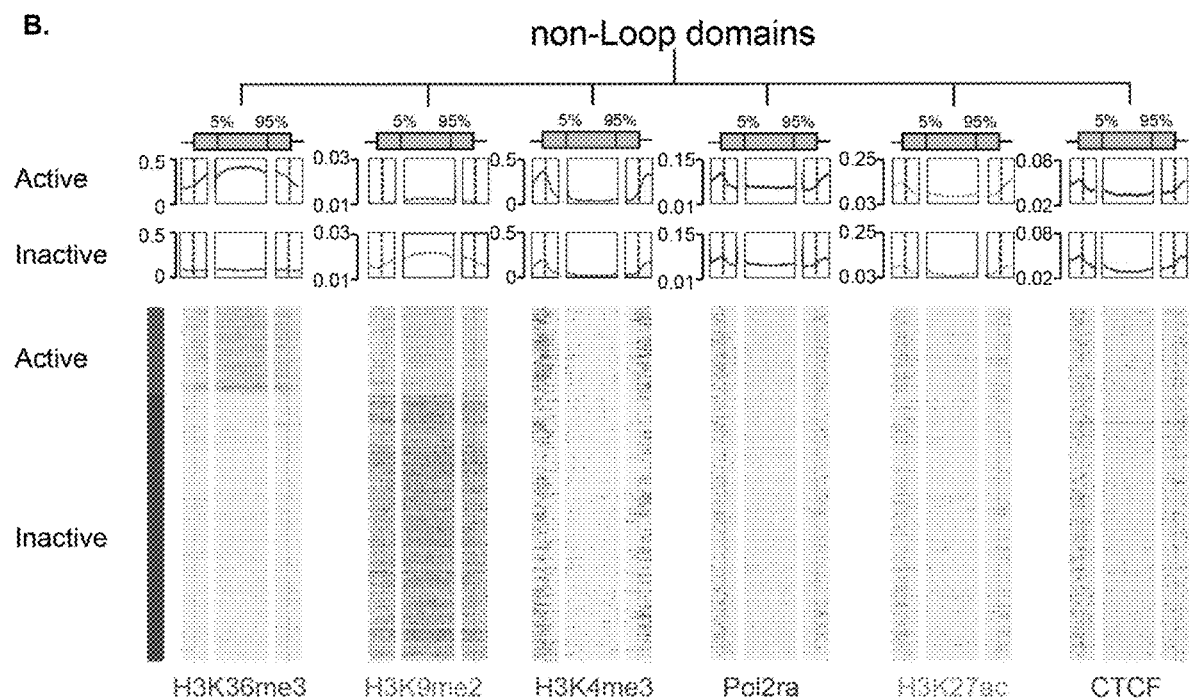
Figure 3C:
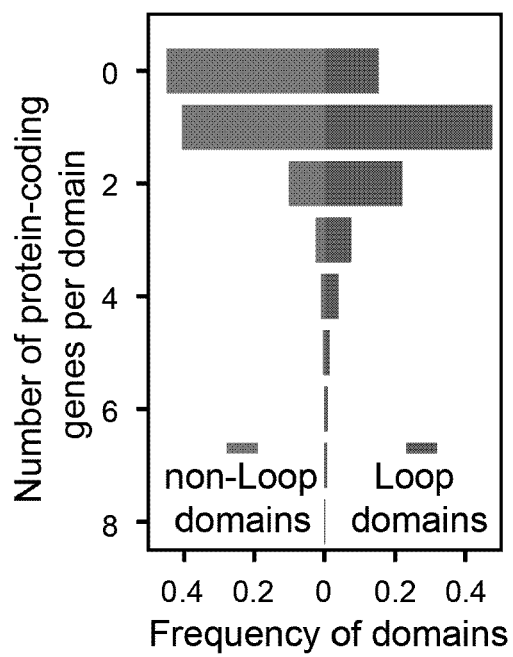
Figure 3D:
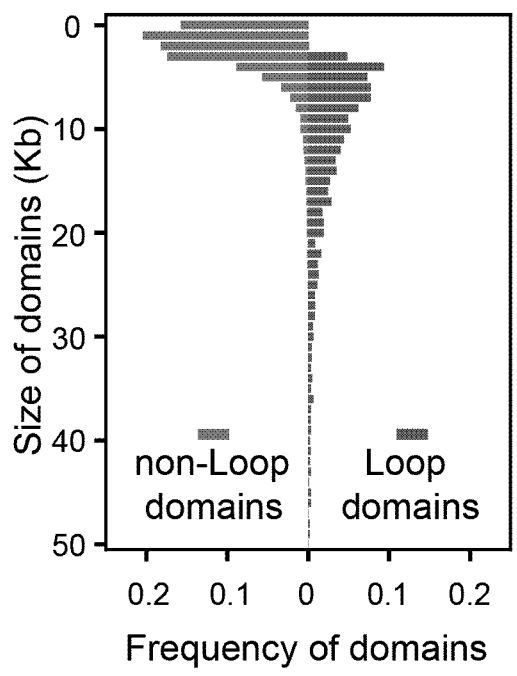
Figure 3E:
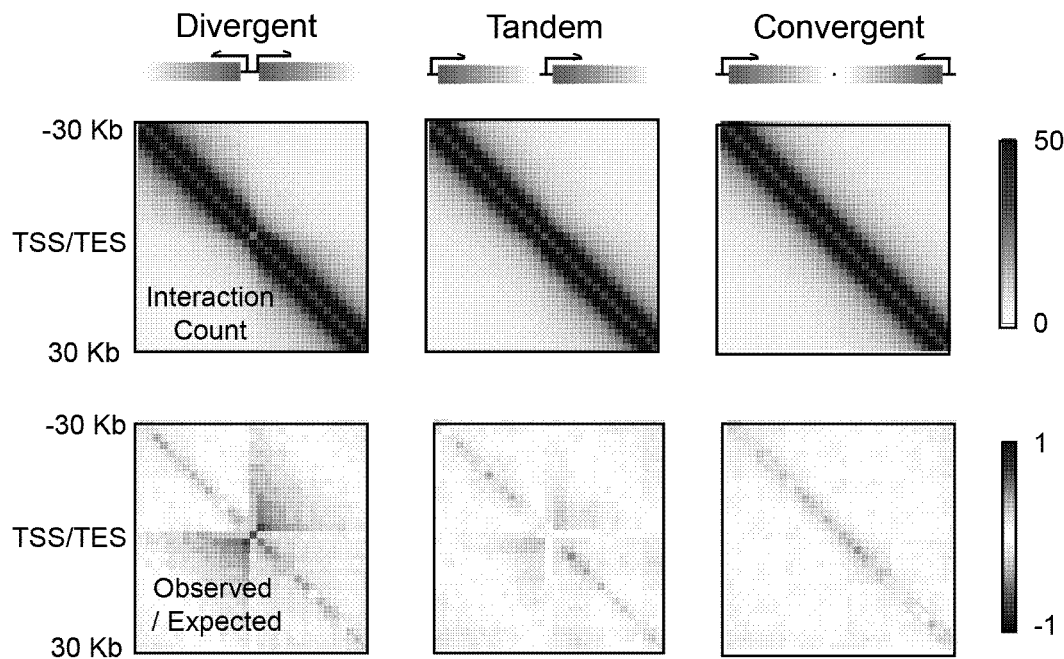
Figure 3F:
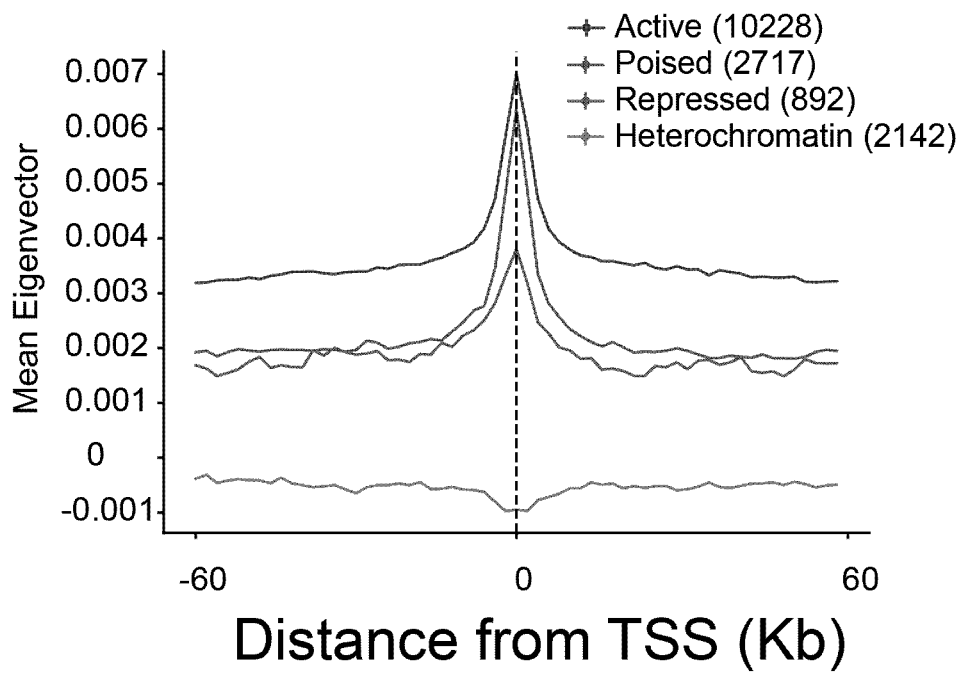
Figure 3G:
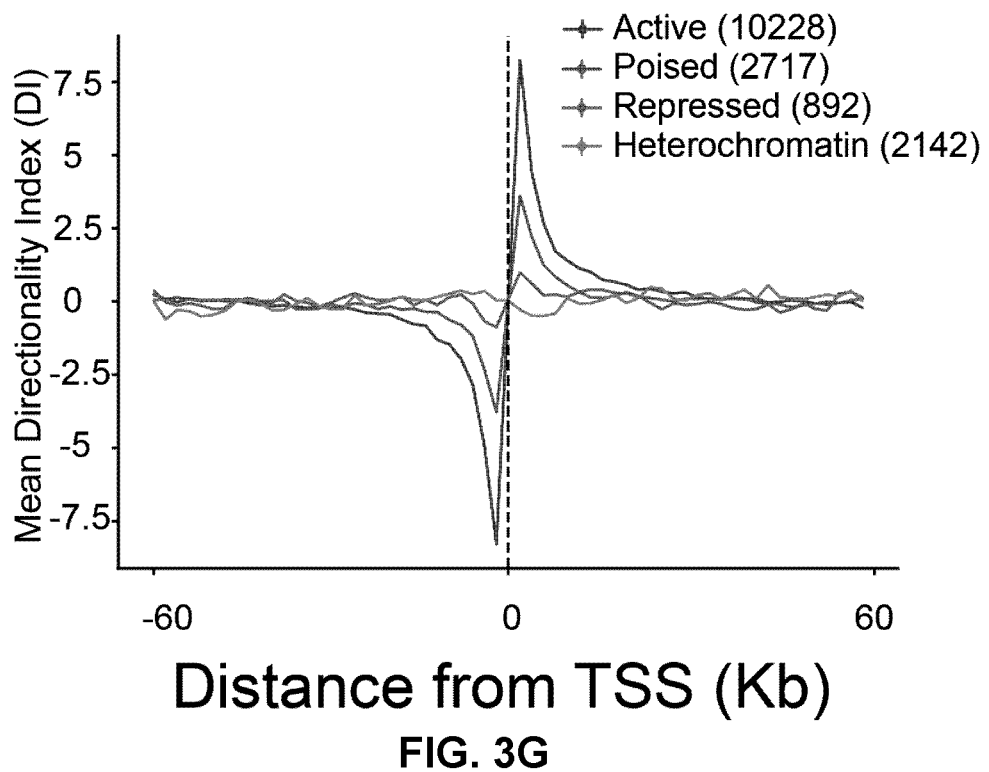
Figure 3H:
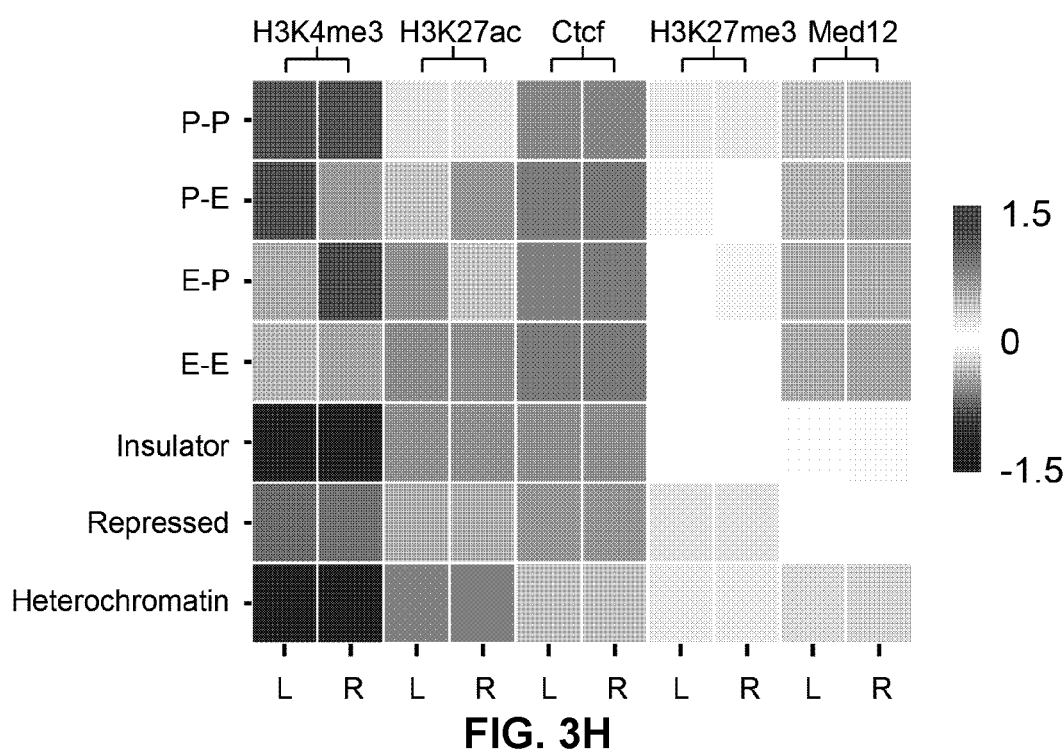
Figure 3I:
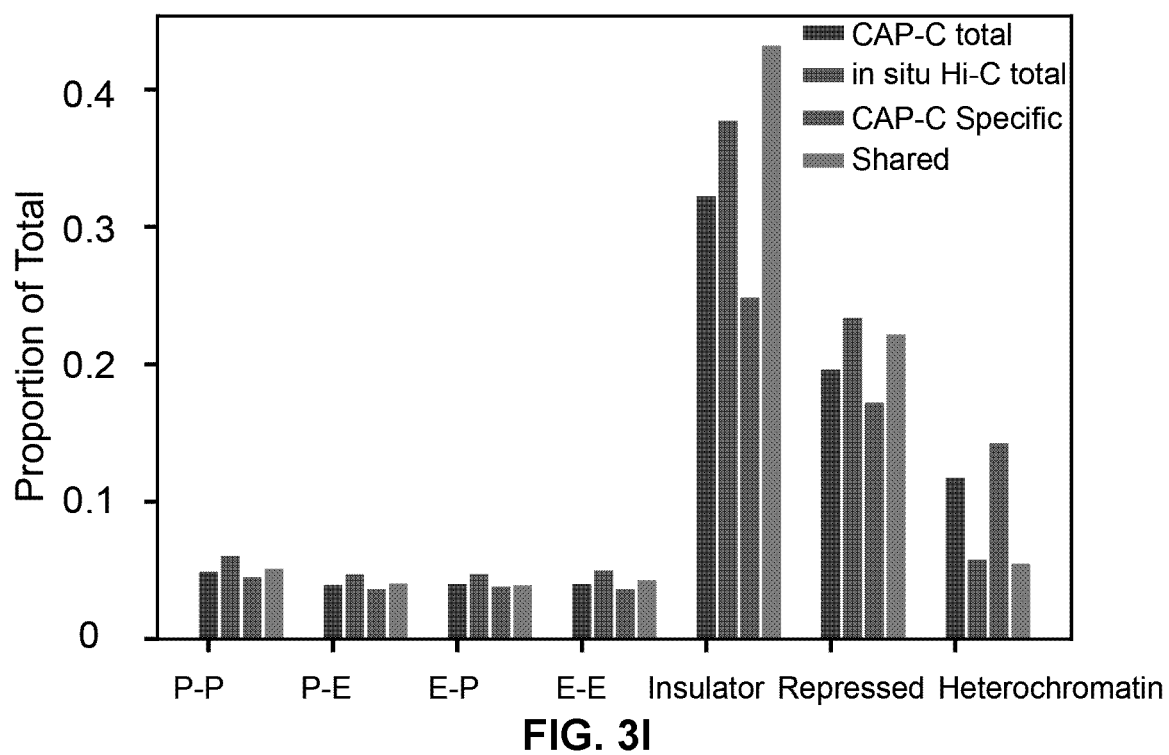

To study the possible mechanisms separating the two types of domains, the inventors next overlapped domain boundaries and domain bodies with a series of histone modification marks. To account for the long-tailed size distribution of some of these domains, and the relatively smaller peaks generally associated with histone modification marks and transcription factors, the inventors extracted only signals +/−2 Kb around the boundary, and signals from 5-95% around the domain body. As expected, loop domains showed stronger Ctcf and cohesin signals than non-loop domains at their boundaries. However, some of the non-loop domain boundaries are also enriched with Ctcf and cohesin binding, suggesting that not all Ctcf- and cohesion-enriched domain boundaries form loops. Conversely, non-loop domains exhibit stronger H3K4me3, H3K27ac, PolII and Top2b signals than loop domains at their boundaries (FIG. 3, A and B, FIG. 14). The inventors calculated a 2.2-fold enrichment of active promoter marks in non-loop domains compared to loop domains (Fisher's Exact Test; P<0.0001). Using K-means clustering, the inventors classified domains by the presence of H3K36me3, an epigenetic mark for transcription elongation, in domain bodies. Non-loop domains with low H3K36me3 signals still contain a 3.2-fold and 2.7-fold enrichment of H3K4me3 and PolII signals over loop domains with no H3K36me3 signals, respectively (Fisher's Exact Test, both P<0.0001). The inventors then asked whether the strength of domain boundaries correlate with the level of transcription. Indeed, using chromatin states information, the inventors were able to classify TSS into four transcriptional elongation states and observed that boundaries of actively transcribed genes were highly open when plotted with mean CAP-C eigenvector values (FIG. 3F), and were located at the center of domain boundaries when viewed alongside mean directionality index (DI) values (FIG. 3G). In addition, TSS marked by poised promoters of bivalent states (PRC2-repression+PolII-H3K4me3 active promoter) and PRC2-repressed regions showed decreased levels of domain boundary formation, suggesting that transcription elongation might be associated with chromatin structure.

As loop domains were proposed to form via Ctcf-cohesin loop extrusion, the above observation led us to hypothesize that non-loop domains might be established through transcription-induced supercoiling, similar to the formation of CIDs in S. cerevisiae and C. crescentus. The twin-supercoiling domain model could predict how waves of supercoiling that propagate through diffusional pathways react when encountering each other; they either enforce or cancel each other based on the propagation direction. Consistent with this model, our mouse CAP-C maps showed similar domain formation based on the orientation of gene pairs previously shown in S. cerevisiae (FIG. 3E). Moreover, the inventors observed that topoisomerase Top2b, which reduces torsional stress generated during transcription elongation, was highly associated with active promoters. Peaks called in our mESC Top2b ChIP-seq experiments showed a 2.6-fold enrichment of peaks overlapping at least 1 non-loop domain boundary versus that of loop domain boundary (Fisher's Exact Test. P-value<0.0001) (FIG. 14). The enrichment of PolII and Top2b binding on non-loop domain boundaries suggests that such chromatin domains could be formed by the action of supercoiling of duplex DNA during transcription elongation.

Figure 4A:
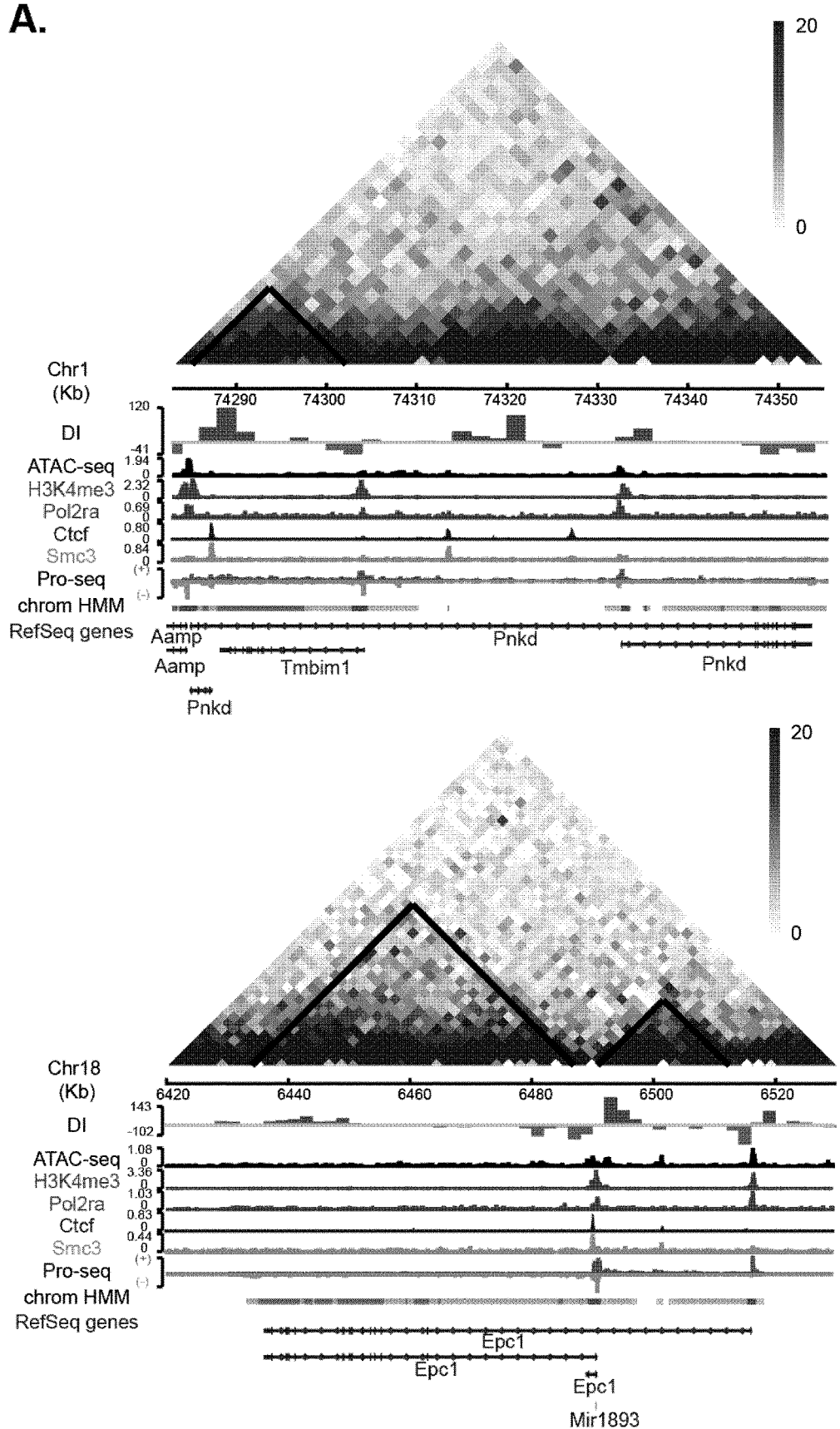
FIGS. 4A-C. Active multiple promoters are involved in contact domain boundary formation. (A) Genes are segregated into different contact domains with active promoter on the boundary. Two examples of CAP-C contact matrix (at 1 KB resolution) are shown corresponding to Chr1: 74.28-74.35 Mb (Left) and Chr18: 6.42-6.53 Mb (Right). Black line depicts the domains called by Arrowhead. Direction index, histone modification and ChIP profiles are listed below each matrix. Entire Pnkd and Epc1 are separated into two domains by active promoter of Tmbim1 and Epc1 respectively. The boundaries are less correlated to Ctcf and cohesin binding. (B and C) Active alternative promoters are highly associated with strong domain boundaries. (B) Genes with alternative promoters were selected and classified into 4 different types based on the transcription state of their first and second promoters. Numbers of each type are shown inside the corresponding brackets. PolII ChTP profiles, Pro-Seq and Direction index around each promoter are shown below. (C) Interaction counts and the log 2 ratio of observed interactions divided by expected interactions for a given genomic distance are shown side by side for each type.
Figure 4B:
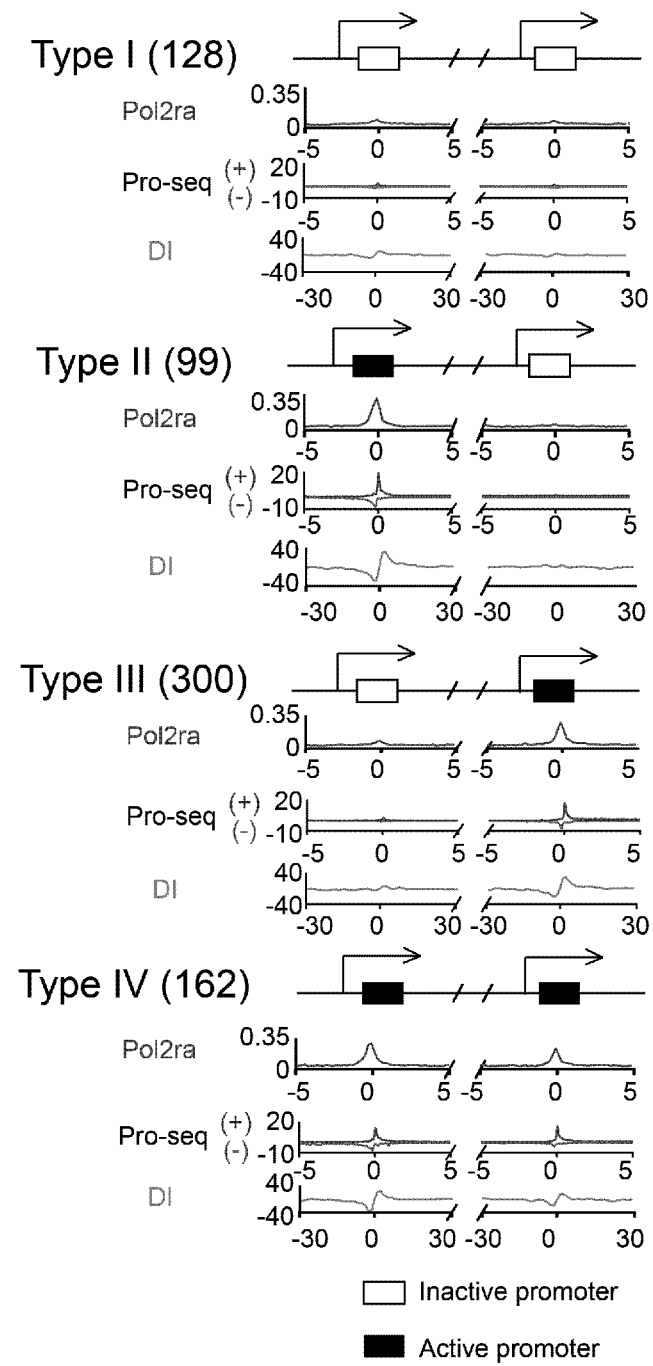
Figure 4C:
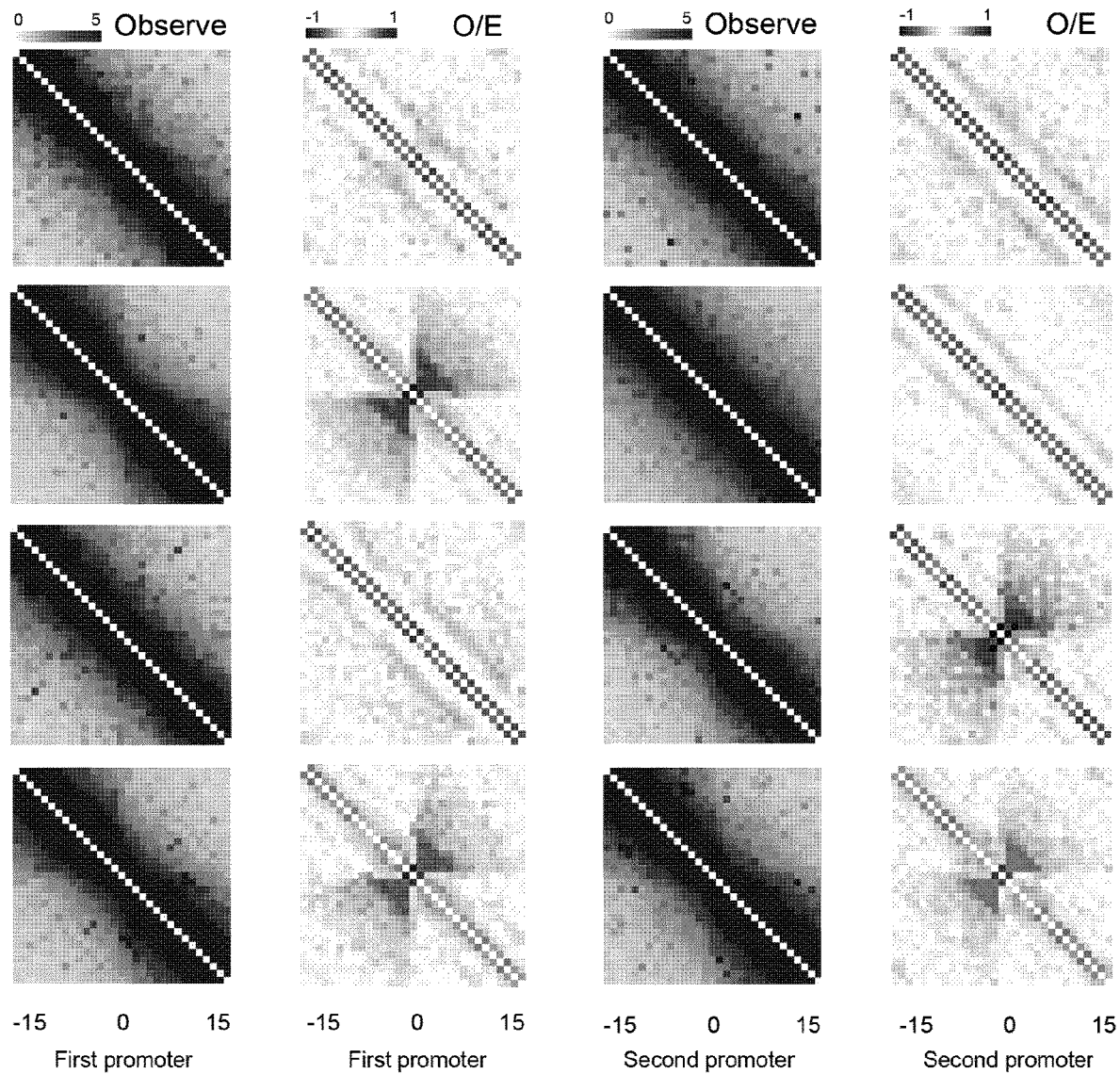

Effects of supercoiling on the structure of genes with multiple active promoters. Alternative promoter usage is a common mechanism for generating transcript complexity. Unlike alternative splicing, alternative promoter usage generates diversity across multiple cell-types by selectively positioning the pre-initiation complex at different transcription start sites (TSS) before elongation. As distances between alternative promoters can range from only tens to thousands of base pairs, these features can now be discernable by our high-resolution contact maps with enriched short-range interactions. Because multiple active promoters that occur in a single gene are in the tandem direction, the inventors predict from the twin-domain-supercoiling model an attenuation of boundaries as positive and negative supercoils cancel each other at the active downstream promoter; this is analogous to the mean O/E contact map of gene pairs that are arranged in a tandem fashion (FIG. 3E). From the high-resolution CAP-C contact matrix, the inventors observed that downstream promoters can cause insulation. Moreover, the domain boundaries correlated strongly with active promoters inside the gene body, and were not well associated with Ctcf or cohein binding (FIG. 4A). Encouraged by this observation, the inventors developed a scheme to select genes with multiple active alternative promoters (H3K4me3) and classified them into 4 possible combinations (FIG. 4B). As expected, the inventors not only observed strong domain boundaries at all active alternative promoter sites, but also observed that promoters downstream of type IV genes showed weaker boundaries in the O/E contact map and reduced directionality index values, even as they are bound by PolII, and showed evidence of divergent transcription (FIG. 4C). Therefore, the inventors propose that negative supercoiling as well as the cancellation of positive and negative supercoils at the domain boundaries causes DNA to be in an unwound (low twists) or relaxed state, fulfilling the requirement of insulation, while conformational changes resulting from both positive and negative supercoiling as writhes fulfill the self-associating property.

Inhibition of transcription reduces supercoiling and leads to global loss of chromatin contacts. Chromatin topology highly associates with supercoiling, and supercoiling domains have been proposed and identified. These supercoiling domains were shown to partially overlap with TADs. Motivated by a relationship between transcription-induced supercoiling and domain organization, the inventors next examined whether transcription inhibition affects chromatin architecture. The inventors explored two different transcription elongation inhibitors, flavopiridol and α-amanitin. Reduced levels and rates of supercoiling have been observed upon transcription inhibition. Thus, the inventors performed time-series CAP-C experiments using G5 dendrimers to crosslink mESC samples treated with 2 µM flavopiridol for 1 h and 6 h, as well as samples treated with 4 µg/ml of α-amanitin for 6 h and 12 h, respectively.

Figure 5A:
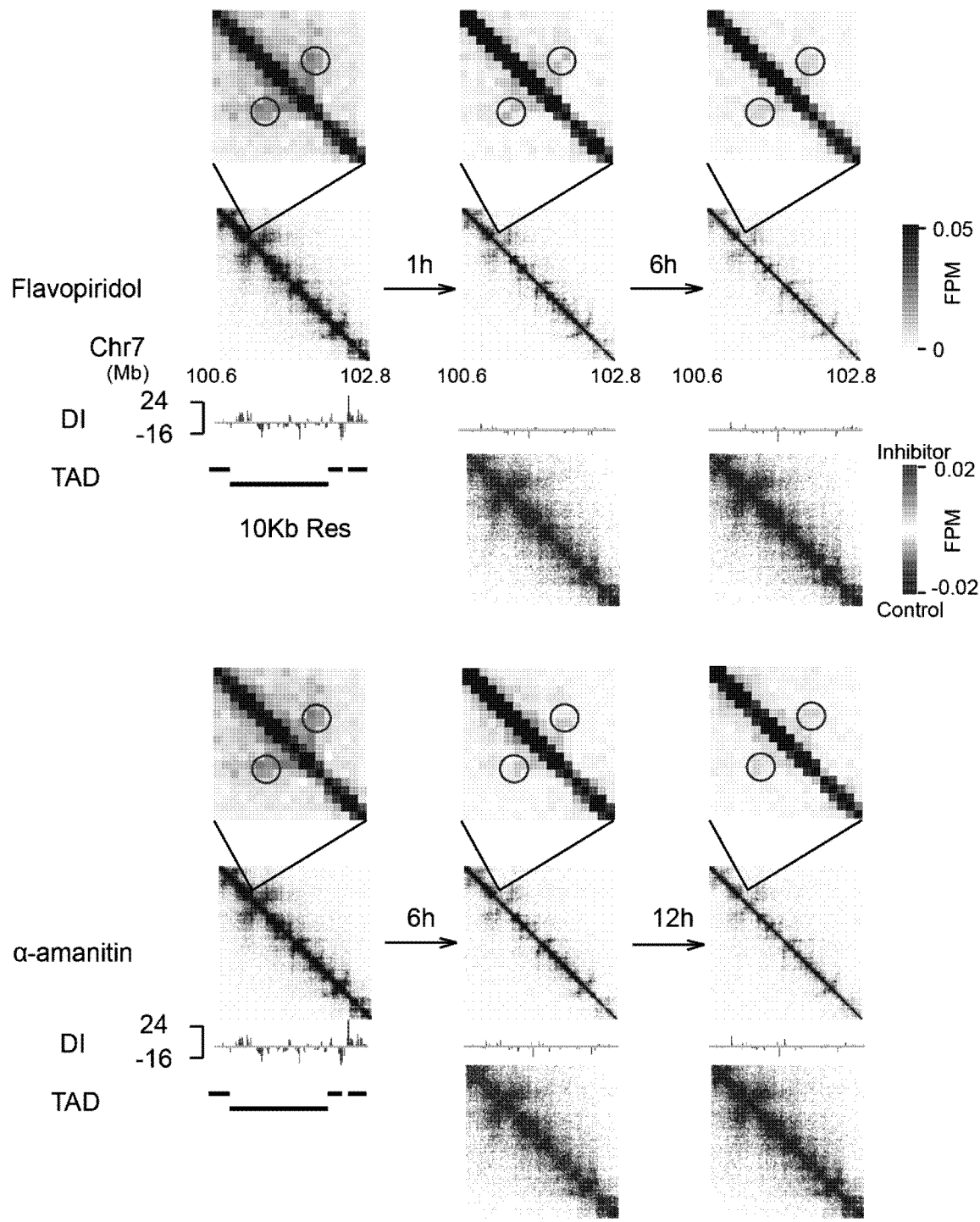
FIGS. 5A-E. Inhibiting transcription causes widespread loss of domains and attenuates loops. (A) 10 kb resolution contact matrix shows a profound decrease in contacts after treatment of 2 µM flavopiridol for 1 h and 6 h as well as 4
Figure 5B:
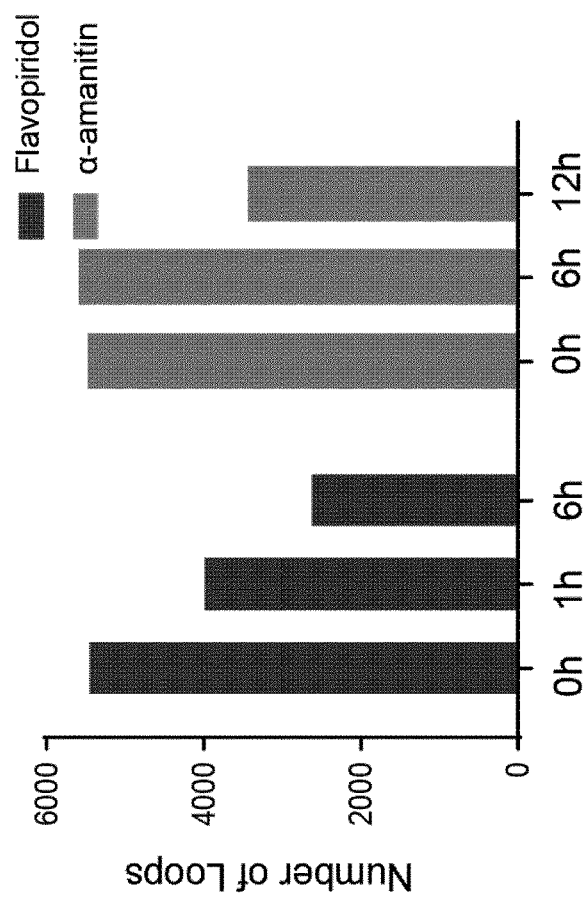
Figure 5C:
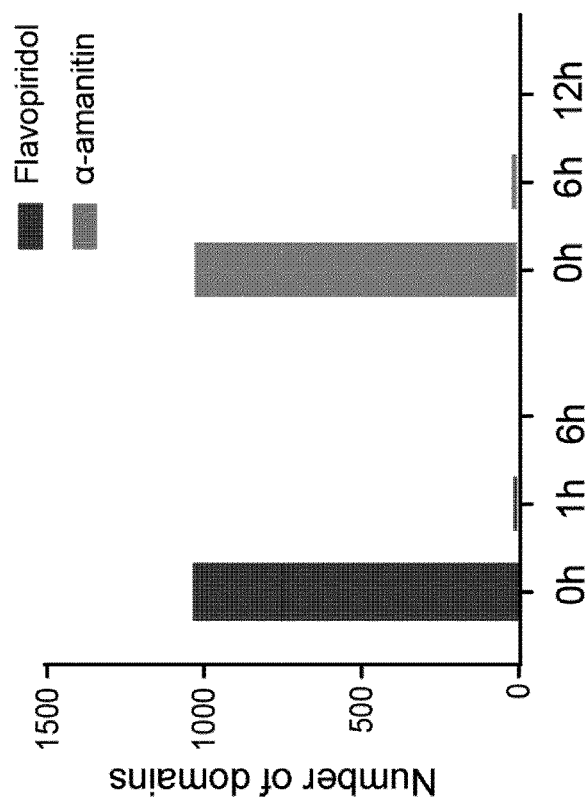
Figure 5C:
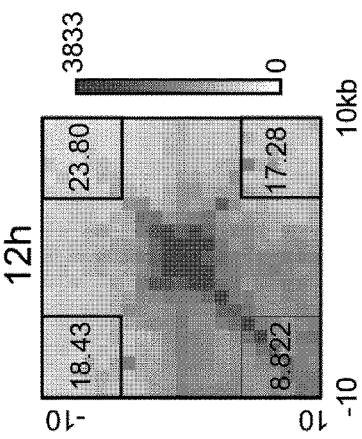
Figure 5C:
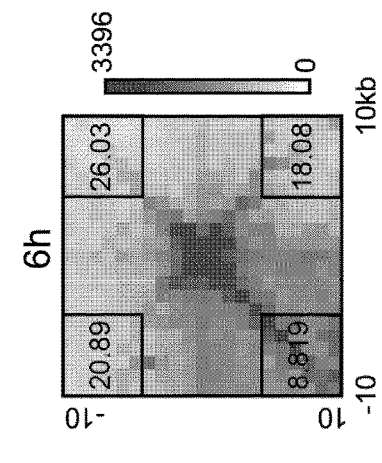
Figure 5C:
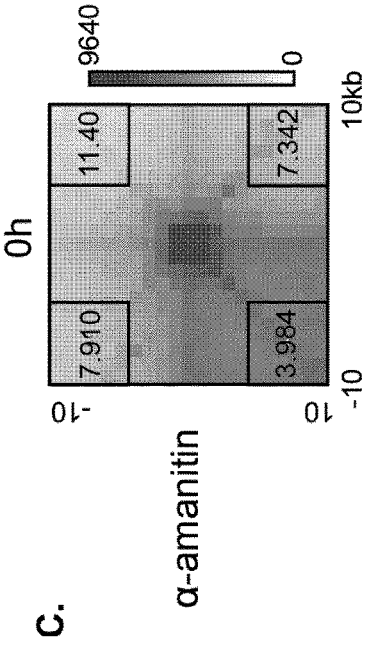
Figure 5D:
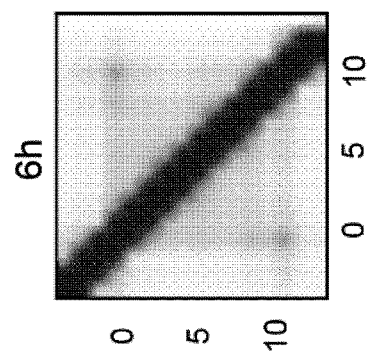
Figure 5D:
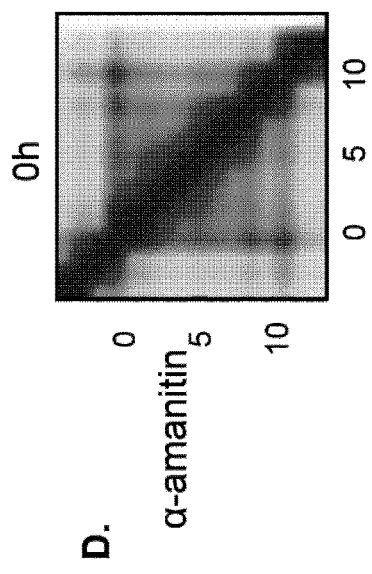
Figure 5E:
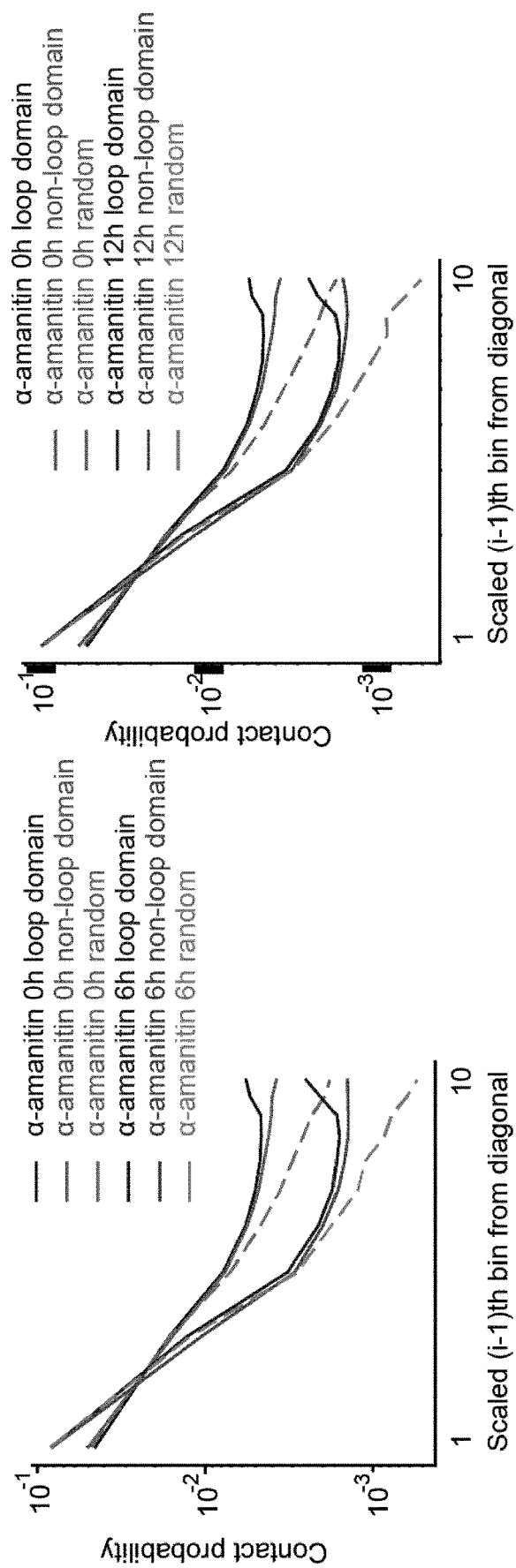

No significant differences were observed between the compartments of G5-control and inhibitor-treated G5 samples, indicating that transcription is not required to maintain compartments, and that compartmentalization may have been established much earlier during early development (FIG. 16). As expected, all 4 inhibitor-treated samples showed a profound loss in long-range interactions greater than 10 Kb in genomic-distance (FIG. 17). CAP-C contact maps also displayed an extensive loss of contacts within domains for all inhibitor-treated samples. Directionality index values used to gauge domain boundaries were extensively decreased (FIG. 5A, FIG. 18), whereas the number of domains called using Arrowhead was significantly reduced (FIG. 5B). However, despite the disappearance of domains, more than half of peaks originally called in the control sample remained (FIG. 5B) after the second-time point (6 hr and 12 hr treatments for flavopiridol and α-amanitin, respectively). The signals of these peaks were, however, weakly attenuated (FIG. 5A). Because these inhibitor-treated and G5-control samples are low-resolution contact maps, the inventors applied Aggregate Peak Analysis (APA) of the peaks called in the deep sequenced CAP-C dataset. A superimposed image of all signals overlapping the peak set showed enrichment of the foci in both G5-control and the inhibitor-treated samples (FIG. 5C, FIG. 19). The inventors plotted the mean contact maps of 103-263 loop-domains (median length: 170 Kb) shared between the control and inhibitor-treated samples by rescaling them into 10 bins (i.e. contact domains in G5-control overlapping loops that are shared between control and inhibitor-treated samples). Contact maps of these loop-domains showed the presence of loops at the corner of the assigned domain boundaries in the inhibitor-treated samples (FIG. 5D). The inventors also quantified these maps into a contact probability vs distance-scaled bins line-plot for all loop domains, non-loop domains and randomly permutated domains. As expected, the inventors observed a general decrease in contact probability between distance-scaled bins 2-7 for both the loop domains and non-loop domains when comparing G5-control and α-amanitin treated sample (the same trends were also seen for flavopiridol-treated samples). Increasing contact frequencies identified at corners of inhibitor-treated loop-domains (bins 8-10) indicate the presence as well as attenuation of peaks from G5-control (FIG. 5E). This is in stark contrast to the absence of such an increase in non-loop domains and randomly permutated domain boundaries.

Therefore, the inventors conclude that domain formations are dependent on transcription-induced supercoiling. Blocking transcription elongation abrogated both loop and non-loop domains; however, loops were attenuated but largely retained. These observations support the critical role of transcription-induced supercoiling in the formation of non-loop domains, but also suggest that transcription-induced supercoiling and loop extrusion likely work synergistically to shape the overall chromatin architecture as the formation of loop domains also appear to be dependent on transcription. Taken together, the inventors propose that positive and negative supercoiling generated during transcription elongation are responsible for the intra-domain contact interactions observed in our experiments.

Probing the openness of transcription starting sites (TSS) by biotinylated psoralen functionalized dendrimers. Different sized dendrimers were functionalized with biotin and psoralen. Each capture experiment was conducted by crosslinking chromatin with one certain sized dendrimer, proteins were removed by proteinase K and the dendrimer-DNA complex was purified by streptavidin pulldown. Enriched DNA fragments were added with Illumina adapters and subjected to high-throughput sequencing. Transcription starting sites (TSS) of wild type cells were first classified by their transcription strength using Pro-seq data into 10 percentiles. $90^{th}$ percentile shows the highest nascent gene expression while the $0^{th}$ percentile exhibits the lowest. Then, the counts were normalized by sequencing depth (FPM) and plotted+/−2 Kb around each types of TSS (FIG. 20). Intriguingly, it was found that aside from dendrimer G1, all other 3 dendrimers showed slight enrichment at TSS. More significant enrichment was observed if the TSS showed higher nascent gene expression. G1 on the contrary, showed a depleted binding preference at TSS, especially for TSS with higher nascent gene expression. Next, the cells were treated with polII inhibitor, flavopiridol, for 1 hour and repeated the experiment. Surprisingly it was discovered that G5 and G7 dendrimers showed less enrichment around TSS compared to G1 and G3. Active TSS were shown to be more open in the wild type. With less polII binding at TSS upon transcription inhibition, the TSS will become relatively more closed compared to wild type. These results suggest that different sized dendrimers are able to probe the openness conformation around TSS.

Example 2

Modified CAP-C

To test the feasibility of a modified embodiment of CAP-C, mouse embryonic stem cells (mESCs) were fixed with formaldehyde. The azide and psoralen functionalized dendrimers were then diffused into the cell nucleus and expose these cells to 365 nm UV irradiation for 30 min. The formaldehyde fixing is then reversed, and DNA-bound proteins are digested with protease to expose all DNA motifs, the dendrimer-DNA complexes are subsequently purified with ethanol precipitation. The purified dendrimer-DNA complexes are then subjected to MNase digestion followed by end polishing and A tailing. Excess enzymes were purified away with phenol chloroform extraction. Bi-functional linkers containing DBCO and biotin were then attached to dendrimer through "Click chemistry". Excess bridge linkers were purified away by size selection with Ampure-XP beads. The DNA-dendrimer complex is then ultra-diluted in ligation buffer and proximal end is joint together via bridge linker by overnight ligation. The ligated products were then pulled out with streptavidin beads followed by library construction and next generation sequencing. A fixation-free version of CAP-C was developed without the need for crosslinking cells with formaldehyde. The azide and psoralen functionalized dendrimers were cross-linked with native chromatin under 365 nm UV irradiation for 30 min with the rest of the procedures remain the same. (FIG. 21)

Some Advantages of CAP-C over in-situ Hi-C: First, the use of micrococcal nuclease (MNase) or a similar enzyme in CAP-C leads to fragmentation of genome into evenly smaller pieces compared to restriction enzymes. Relative frequency of chromatin contacts of short range (below 10 Kb) captured by CAP-C showed 30% increase compared to in situ Hi-C. Enrichment of short-range CAP-C contacts allowed better resolution of new features of the genome at shorter length-scales. In contrast to the highest mESC chromatin contact matrix, CAP-C map at high resolution is clearer and sharper. Many of the small triangles with enhanced contact frequency close to the diagonal were observed in CAP-C, and were called as domains by using Arrowhead at 500 bp, which were not distinguishable as domains in in-situ Hi-C maps with a similar sequencing depth. (FIG. 22) Compared to in-situ Hi-C maps, CAP-C maps called 2.0-fold more domains with sizes of 5 to 25 Kb, but 1.2-fold fewer domains with sizes greater than 40 Kb. Boundaries of CAP-C specific domains in 5 to 25 Kb length features in better correlation with active histone marks as well as known architecture proteins such as CTCF and cohesin. While for domains with sizes greater than 40 Kb, they exhibit similar or slightly higher correlation compared to in-situ Hi-C specific domain boundaries. This allows the application of CAP-C to identify more structural and functional related domains at high-resolution. (FIG. 23, left)

Secondly, with the help of bridge linker, CAP-C is able to filter out genomic contacts that are randomly joint together to achieve low background on the contact matrix compared to in-situ Hi-C. Meta-analyses performed on short (100-200 Kb) and long (300-500 Kb) concordant peaks around loop anchors between CAP-C and in-situ Hi-C suggested that even though depth-normalized signal values (FPM) at the foci were similar between maps, a faster decay in mean long-range contacts between the two anchors decreases the mean lower-left background values in CAP-C. (FIG. 24) This effect significantly increases the signal-to-noise ratio around loop anchors and consequently increases up to 2.5-fold more loops called at a constant threshold for CAP-C. In addition, it was observed that the more loops called in CAP-C specific have higher correlation with active histone marks as well as CTCF or cohesin, suggesting that CAP-C identifies loops better than in-situ Hi-C at all length-scale. (FIG. 23, right)

Third, different sizes of dendrimer crosslinkers used in CAP-C are able to access and probe distinct regions of chromatin compaction as a result of dendrimer size-dependent enrichment of interactions in differential regions. Using principal component analysis, it was determined that the eigenvector with the highest eigenvalue using the pixel values of each G3, G5 and G7 contact maps and plotted a 2D map which we named as "dendrimer map" based on the eigenvector values of the 1st principal component. Most importantly, these "dendrimer maps" showed plaid-like pattern similar to that of A/B compartment intervals identified previously in Hi-C, with small dendrimer G3 enriched regions showed high correlation with B compartment while large dendrimer G5 and G7 favored regions correlate better with A compartment. Compartment B is highly associated with heterochromatin and showed high correlation with inactive histone mark H3K27me3 while compartment A is positively related to open chromatin and active histone mark H3K36me3. It is reasonable to explain such observation as small dendrimer will access to the close chromatin conformation while large dendrimers are better fit for open chromatin conformation. Moreover, "CAP-C eigenvectors" were obtained in a series of resolution for different species and discovered smaller compartment intervals that are kilobases in length, suggesting that genomes are partitioned into A/B compartments at an ultra-small scale and such folding principles are shared among species. (FIG. 25)

Detailed Examples of CAP-C Protocols:

CAP-C with formaldehyde crosslinking. Grow five million cells under recommended culture conditions. Detach adherent cells by centrifugation at 300×G for 5 min. Resuspend cells in fresh medium at 1 million cells per 1 ml medium. Add 16% formaldehyde solution to a final concentration of 1%, v/v. Incubate at r.t. for 5 min on rotating rocker. Add 2.5 M glycine solution to a final concentration of 0.2 M to quench the reaction. Incubate at r.t. for 5 min on rotating rocker. Centrifuge for 5 min at 300×G at 4° C. Discard supernatant. Resuspend cells in 1 ml of cold 1× PBS and spin for 5 min at 300×G at 4° C. Discard supernatant and flash-freeze cell pellets in liquid nitrogen (can be stored in −80° C. for up to a year). Combine 250 μl of ice-cold lysis buffer (10 mM Tris-HCl, pH 8.0, 10 mM NaCl, 0.2% Igepal CA630) with 50 μl of protease inhibitors (Sigma, P8340). Add to formaldehyde fixed pellet of cells. Incubate cell suspension on ice for 20 min. Centrifuge at 2500×G for 5 min. Discard the supernatant. Wash pelleted nuclei once with 500 μl of ice-cold Hi-C lysis buffer. Centrifuge and discard the supernatant. Resuspend the cell pellet in 1 ml 50 μM dendrimer in methanol. Incubate at 4° C. on a rocker with rotation. Photo crosslink the nuclei by irradiating under 365 nm UV for 30 min. Centrifuge for 5 min at 2500×G at 4° C. Discard supernatant. Wash pelleted nuclei twice with 500 μl of ice-cold Hi-C lysis buffer. Centrifuge and discard the supernatant. Resuspend the pellet in proteinase K buffer (420 μl Hi-C lysis buffer, 50 μl 10% SDS, 30 μl 20 mg/ml proteinase K) Incubate at 65° C. for O/N on a thermomixer at 800 rpm.

CAP-C without formaldehyde crosslinking. Grow five million cells under recommended culture conditions. Detach adherent cells by centrifugation at 300×G for 5 min. Combine 250 μl of ice-cold nucleus lysis buffer (10 mM Tris, pH 7.5, 10 mM NaCl, 3 mM MgCl$_2$, 0.5% NP-40, 0.15 mM spermine, 0.5 mM spermidine) with 50 μl of protease inhibitors (Sigma, P8340). Add to pellet of cells. Incubate cell suspension on ice for 5 min. Centrifuge at 500×G for 5 min. Discard the supernatant. Wash pelleted nuclei once with 500 μl of resuspension buffer (10 mM Tris-HCl pH 7.4, 15 mM NaCl, 60 mM KCl, 0.15 mM spermine, 0.5 mM spermidine). Centrifuge at 500×G for 5 min and discard the supernatant. Resuspend the cell pellet in 1 ml 50 μM dendrimer in methanol. Incubate at 4° C. on a rocker with rotation for 10 min. Photo crosslink the nuclei by irradiating under 365 nm UV for 30 min. Centrifuge for 5 min at 2500×G at 4° C. Discard supernatant. Wash pelleted nuclei twice with 500 μl of resuspension buffer. Centrifuge and discard the supernatant. Resuspend the pellet in proteinase K buffer (420 μl Hi-C resuspension buffer, 50 μl 10% SDS, 30 μl 20 mg/ml proteinase K) Incubate at 65° C. for O/N on a thermomixer at 800 rpm.

Extract the DNA with 500 μl phenol:chloroform. Centrifuge at max for 10 min at r.t. Transfer the upper layer to a new tube. Add 800 μl EtOH and 50 μl 3 M NaOAc (pH 5.5). Incubate at −80° C. for 1 h. Centrifuge at max for 15 min at 4° C. Discard the supernatant. Wash the pellet twice with 500 μl 70% EtOH. Centrifuge at max for 5 min at 4° C. Discard the supernatant.

Resuspend the DNA pellet in 100 μl MNase digestion buffer (10 mM Tris-HCl pH 7.4, 15 mM NaCl, 60 mM KCl, 1 mM CaCl$_2$), 0.15 mM spermine, 0.5 mM spermidine). Add 1 unit of MNase and incubate at 37° C. for 5 min then stop the reaction by adding 150 μl of Stop Buffer. (20 mM EDTA, 20 mM EGTA, 0.4% SDS) Incubate the mixture at 65° C. for 30 min. Purify DNA with ethanol precipitation by adding 800 μl EtOH and 50 1 3 M NaOAc (pH 5.5). Incubate at −80° C. for 1 h. Centrifuge at max for 15 min at 4° C. Discard the supernatant. Wash the pellet twice with 500 μl 70% EtOH. Centrifuge at max for 5 min at 4° C. Discard the supernatant. Resuspend the DNA pellet in 100 μl H$_2$O.

Repair DNA ends and add "A" using the KAPA Hyper plus kit by adding the following mix: 100 μl of above DNA-Dendrimer complex; 28 μl of ER&AT buffer mix; 12 μl of ER&AT enzyme mix.

Incubate at 20° C. for 30 min then 65° C. for 30 min. Purify DNA with ethanol precipitation by adding 500 μl EtOH and 20 μl 3 M NaOAc (pH 5.5). Incubate at −80° C. for 1 h. Centrifuge at max for 15 min at 4° C. Discard the supernatant. Wash the pellet twice with 500 μl 70% EtOH. Centrifuge at max for 5 min at 4° C. Discard the supernatant. Resuspend the DNA pellet in 100 μl H2O. Add 2 μl of 100 μM biotin linker and incubate at 37° C. for 2 h on a thermomixer at 800 rpm. Excess of biotin linkers are removed by XP beads size selection. DNA is eluted with 100 μl of H$_2$O.

Prepare for biotin pull-down by washing 20 μl of 10 mg/ml Dynabeads MyOne Streptavidin C1 beads (Life technologies) with 400 μl of 1× Tween Washing Buffer (1× TWB: 5 mM Tris-HCl (pH 7.5); 0.5 mM EDTA; 1 M NaCl; 0.05% Tween 20). Separate on a magnet and discard the solution. Resuspend the beads in 100 μl of 2× Binding Buffer (2× BB: 10 mM Tris-HCl (pH 7.5); 1 mM EDTA; 2 M NaCl) and add to the reaction. Incubate at room temperature for 15 min with rotation to bind biotinylated DNA to the streptavidin beads. Separate on a magnet and discard the solution. Wash the beads by adding 600 μl of 1× TWB and transferring the mixture to a new tube. Heat the tubes on a Thermomixer at 55° C. for 2 min with mixing. Reclaim the beads using a magnet. Discard supernatant. Repeat wash.

Ligate the proximal DNA on the same dendrimer by adding the following mix: 4 ml of water; 500 μl of 10× NEB T4 DNA ligase buffer (NEB, B0202); 1 ml of above DNA-Dendrimer complexes; and 20 μl of 400 U/μl T4 DNA Ligase (NEB, M0202). Incubate at 16° C. for overnight on a rotating rocker. Separate on a magnet and discard the solution.

Wash the Streptavidin C1 beads by adding 600 μl of 1× TWB and transferring the mixture to a new tube. Heat the tubes on a Thermomixer at 55° C. for 2 min with mixing. Reclaim the beads using a magnet. Discard supernatant. Repeat wash. Perform all the following steps in low-bind tubes. Resuspend beads in 100 ul 1× NEB T4 DNA ligase buffer (NEB, B0202) and transfer to a new tube. Reclaim beads and discard the buffer. To repair ends of sheared DNA and remove biotin from unligated ends, resuspend beads in 100 μl of master mix: 88 μl of 1× NEB T4 DNA ligase buffer with 10 mM ATP S33, 2 μl of 25 mM dNTP mix, 5 μl of 10 U/μl NEB T4 PNK (NEB, M0201), 4 μl of 3 U/μl NEB T4 DNA polymerase I (NEB, M0203), 1 μl of 5 U/μl NEB DNA polymerase I, Large (Klenow) Fragment (NEB, M0210) Incubate at room temperature for 30 min. Separate on a magnet and discard the solution. Wash the beads by adding 600 μl of 1× TWB and transferring the mixture to a new tube. Heat the tubes on a Thermomixer at 55° C. for 2 min with mixing. Reclaim the beads using a magnet. Discard supernatant. Repeat wash. Resuspend beads in 100 μl 1× NEBuffer 2 and transfer to a new tube. Reclaim beads and discard the buffer. Resuspend beads in 100 μl of dATP attachment master mix: 90 μl of 1× NEBuffer 2, 5 μl of 10 mM dATP, 5 μl of 5 U/μl NEB Klenow exo minus (NEB, M0212). Incubate at 37° C. for 30 min. Separate on a magnet and discard the solution. Wash the beads by adding 600 μl of 1× TWB and transferring the mixture to a new tube. Heat the tubes on a Thermomixer at 55° C. for 2 min with mixing. Reclaim the beads using a magnet. Discard supernatant. Repeat wash. Resuspend beads in 100 μl 1× Quick ligation reaction buffer (NEB, B6058) and transfer to a new tube. Reclaim beads and discard the buffer. Resuspend in 50 μl of 1× NEB Quick ligation reaction buffer. Add 2 μl of NEB DNA Quick ligase (NEB, M2200). Add 3 μl of Illumina indexed adapter. (Nextflex) Record the sample-index combination. Mix thoroughly. Incubate at room temperature for 15 min. Separate on a magnet and discard the solution. Wash the beads by adding 600 μl of 1× TWB and transferring the mixture to a new tube. Heat the tubes on a Thermomixer at 55° C. for 2 min with mixing. Reclaim the beads using a magnet. Remove supernatant. Repeat wash. Wash 3 times with 100 μl water. Reclaim the beads with 50 μl water. Incubate at 98° C. for 10 min to elute the DNA from the beads. Transfer the supernatant to an 8-well PCR tube. PCR amplify 7-12 cycles with following conditions: 98° C. 30 s; 98° C. 15 s; 60° C. 30 s; 72° C. 30 s; Repeat 12 cycles; 72° C. 1 min.

Purify the libraries with 0.9× Ampure beads. Elute with 30 μl water. Check the ligation efficiency by aliquot 8 μl DNA libraries and adding 1 μl 10× CutSmart buffer, 1 μl BspdI. Incubate at 37° C. for 1 h. Run a 2% agarose gel with digested libraries and original libraries side by side. A clear shift-down to small size should be observed with EcoRV digested libraries.

---

The invention claimed is:

1. A chromatin mapping method comprising:
   (a) contacting a chromatin target structure comprising nucleic acids and histones with a functionalized dendrimer comprising cross-linking moieties to form a chromatin/dendrimer mixture;
   (b) exposing the chromatin/dendrimer mixture to an activator to activate the cross-linking moieties of the functionalized dendrimer and, thereby forming a cross-linked chromatin/dendrimer complex;
   (c) isolating the cross-linked chromatin/dendrimer complex; and
   (d) identifying genomic loci from the isolated chromatin/dendrimer complex.

2. The method of claim 1, wherein the functionalized dendrimer has a diameter of 1 to 100 nm.

3. The method of claim 1, wherein the chromatin target structure is *in situ*.

4. The method of claim 1, wherein the chromatin target structure is in a cell.

5. The method of claim 4, further comprising fixing the cell prior to contacting the cell with the functionalized dendrimer.

6. The method of claim 5, wherein the cell is fixed with formaldehyde.

7. The method of claim 5, further comprising unfixing the cell after formation of the chromatin/dendrimer complex.

8. The method of claim 1, wherein the activator is light.

9. The method of claim 8, wherein the light is ultraviolet light.

10. The method of claim 8, wherein the light has a wavelength of about 350 to 375 nm.

11. The method of claim 1, wherein isolating the cross-linked chromatin/dendrimer complex comprises exposing the cross-linked chromatin/dendrimer complex to a proteinase or a nuclease, forming a treated chromatin/dendrimer complex.

12. The method of claim 1, wherein isolating the cross-linked chromatin/dendrimer complex comprises fragmenting the cross-linked chromatin/dendrimer complex and conducting proximal ligation of resulting fragments.

13. The method of claim 12, wherein fragmenting the cross-linked chromatin/dendrimer complex comprises endonuclease or exonuclease digestion.

14. The method of claim 1, wherein isolating the cross-linked chromatin/dendrimer complex comprises contacting the cross-linked chromatin/dendrimer complex with an affinity agent that specifically binds a component or portion of the cross-linked chromatin/dendrimer complex.

15. The method of claim 14, wherein the affinity agent is a nucleic acid probe.

16. The method of claim 1, wherein identifying the genomic loci comprises sequencing a nucleic acid associated with the isolated crosslinked chromatin/dendrimer complex.

17. A method comprising:
(a) contacting a chromatin structure with a functionalized dendrimer comprising activatable cross-linking moieties to form a chromatin structure/dendrimer mixture, wherein the dendrimer is also coupled to an avidity tag;
(b) exposing the chromatin structure/dendrimer mixture to an activator to activate the cross-linking moieties of the dendrimer and form a cross-linked chromatin structure/dendrimer complex;
(c) contacting the cross-linked chromatin structure/dendrimer with an affinity agent that binds a chromatin associated protein, wherein the affinity agent is coupled to an avidity tag modification agent, wherein the avidity tag modification agent, when brought in proximity to an avidity tag, modifies the avidity tag forming an isolatable cross-linked chromatin/dendrimer complex;
(d) isolating the cross-linked chromatin structure/dendrimer complex via the avidity tag; and
(e) identifying portions of nucleic acid associated with the cross-linked chromatin structure/dendrimer complex isolated in (d).

18. A method comprising:
(a) contacting a target in proximity to a RNA with a functionalized dendrimer comprising activatable cross-linking moieties to form a target/dendrimer mixture, wherein the target is a RNA-binding target or protein target, wherein the functionalized dendrimer is also coupled to an avidity tag;
(b) exposing the target/dendrimer mixture to an activator to activate the cross-linking moieties of the functionalized dendrimer and form a cross-linked target/dendrimer complex;
(c) contacting the cross-linked target/dendrimer complex with an affinity agent that binds a RNA-binding protein or protein target in proximity to the RNA, wherein the affinity agent is coupled to an avidity tag modification agent, wherein the avidity tag modification agent, when brought in proximity to an avidity tag, modifies the avidity tag forming an isolatable cross-linked target/dendrimer complex;
(d) isolating the cross-linked target/scaffold complex via the avidity tag; and
(e) identifying portions of the RNA that is associated with the cross-linked target/dendrimer complex isolated in (d).

19. The method of claim 1, wherein the dendrimer is a PAMAM dendrimer.

20. The method of claim 1, wherein the functionalized dendrimer is a psoralen functionalized dendrimer.

21. The method of claim 1, wherein the functionalized dendrimer has a diameter of less than 10 nm.

22. The method of claim 1, wherein the functionalized dendrimer has a diameter of less than 5 nm.

23. The method of claim 1, wherein the chromatin structure is contacted with an additional functionalized scaffold having a diameter that is different than the functionalized dendrimer.

24. The method of claim 23, wherein a biological sample comprising the chromatin structure is first divided into a first and second portion, wherein the first portion is contacted with the functionalized dendrimer and the second portion is contacted with the additional functionalized scaffold.

25. The method of claim 1, wherein the chromatin structure is contacted with at least three distinct functionalized scaffolds with each scaffold having a different diameter as compared to the other functionalized scaffolds, wherein at least one functionalized scaffold is a functionalized dendrimer.

* * * * *

SEQUENCE LISTING

```
<160> NUMBER OF SEQ ID NOS: 34

<210> SEQ ID NO 1
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 1
gatttgctca gcagatggc                                             19

<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 2
gcaaatgccc agaggttc                                              18

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
ctacccagaa acagcaagtg                                            20

<210> SEQ ID NO 4
```

```
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
tttctgtgtt gctattcggt a                                           21

<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 5
catcagatta agggcgcca                                              19

<210> SEQ ID NO 6
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 6
acgcagtagg agaccgg                                                17

<210> SEQ ID NO 7
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 7
gctttcctca tggaaatgc                                              19

<210> SEQ ID NO 8
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 8
caggcacagc ctcgt                                                  15

<210> SEQ ID NO 9
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 9
acgtggctga ggctga                                                 16

<210> SEQ ID NO 10
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 10
```

```
tctctggctc actcacc                                                  17

<210> SEQ ID NO 11
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 11
ttctctcatc tgcaccgg                                                 18

<210> SEQ ID NO 12
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 12
caggcggaag tgacgt                                                   16

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
aggaccatct gtgcacggag                                               20

<210> SEQ ID NO 14
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 14
ggttacgcat gcagagcc                                                 18

<210> SEQ ID NO 15
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 15
caccccaagg gcttaga                                                  17

<210> SEQ ID NO 16
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 16
aaggatgctc caccacc                                                  17

<210> SEQ ID NO 17
<211> LENGTH: 21
<212> TYPE: DNA
```

```
<213> ORGANISM: Artificial Sequence
<220> FEATURE:
<223> OTHER INFORMATION: synthetic oligonucleotide

<400> SEQUENCE: 17
catagacgag tcattgtttc g                                             21

<210> SEQ ID NO 18
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 18
gccctctggt ggagacat                                                 18

<210> SEQ ID NO 19
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 19
ccagaggctg tggcttc                                                  17

<210> SEQ ID NO 20
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 20
caagagacag ctaaatcagg gt                                            22

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
cttatcgact gttgccatgg                                               20

<210> SEQ ID NO 22
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 22
cttagccttg gtatcaactg g                                             21

<210> SEQ ID NO 23
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 23
gggagtagaa agaaggccc                                                19
```

<210> SEQ ID NO 24
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 24
ggcatttcac ctcactgca                                               19

<210> SEQ ID NO 25
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 25
tctataaaga tgcctctgag gt                                           22

<210> SEQ ID NO 26
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 26
tctgcttcat tgagaattta cag                                          23

<210> SEQ ID NO 27
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
tataggttgg ctccaagctc t                                            21

<210> SEQ ID NO 28
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 28
gatacctgat tcagatggtg ca                                           22

<210> SEQ ID NO 29
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 29
gacatcctgc cttccctg                                                18

<210> SEQ ID NO 30
<211> LENGTH: 20
<212> TYPE: DNA
<213> ORGANISM: Artificial Sequence
<220> FEATURE:

```
<223> OTHER INFORMATION: synthetic oligonucleotide

<400> SEQUENCE: 30
gtgggtcaag ttctcaatgg                                                     20

<210> SEQ ID NO 31
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 31
tactgactct gacaccagat g                                                   21

<210> SEQ ID NO 32
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 32
catgagactg acttaagcat ct                                                  22

<210> SEQ ID NO 33
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 33
cgcgatatct tatctgact                                                      19

<210> SEQ ID NO 34
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 34
gtcagataag atatcgcgt                                                      19
```